(12) United States Patent
Hanley-Bowdoin et al.

(10) Patent No.: US 9,102,705 B2
(45) Date of Patent: Aug. 11, 2015

(54) PEPTIDE APTAMERS THAT BIND TO THE REP PROTEINS OF SSDNA VIRUSES

(75) Inventors: Linda Hanley-Bowdoin, Raleigh, NC (US); Luisa Lopez-Ochoa, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 455 days.

(21) Appl. No.: 13/437,688

(22) Filed: Apr. 2, 2012

(65) Prior Publication Data

US 2012/0220519 A1 Aug. 30, 2012

Related U.S. Application Data

(62) Division of application No. 11/995,973, filed as application No. PCT/US2006/030941 on Aug. 4, 2006, now Pat. No. 8,168,748.

(60) Provisional application No. 60/705,426, filed on Aug. 4, 2005.

(51) Int. Cl.
| | |
|---|---|
| C07K 7/08 | (2006.01) |
| C07K 7/06 | (2006.01) |
| A61K 38/04 | (2006.01) |
| C07K 14/00 | (2006.01) |
| C12Q 1/00 | (2006.01) |
| A61K 38/00 | (2006.01) |

(52) U.S. Cl.
CPC ... *C07K 7/08* (2013.01); *C07K 7/06* (2013.01); *C07K 14/00* (2013.01); *A61K 38/00* (2013.01); *A61K 38/04* (2013.01); *C12Q 1/008* (2013.01)

(58) Field of Classification Search
None
See application file for complete search history.

(56) References Cited

U.S. PATENT DOCUMENTS

| 6,800,793 B2 | 10/2004 | Hanley-Bowdoin et al. | |
|---|---|---|---|
| 2002/0138867 A1* | 9/2002 | Hanley-Bowdoin et al. . | 800/278 |
| 2004/0216190 A1* | 10/2004 | Kovalic | 800/289 |

FOREIGN PATENT DOCUMENTS

| WO | WO 97/39110 A1 | 10/1997 |
|---|---|---|
| WO | WO 97/42315 A1 | 11/1997 |
| WO | WO 97/42316 A1 | 11/1997 |
| WO | WO 2004/065557 * | 8/2004 |
| WO | WO 2004/065557 A2 | 8/2004 |

OTHER PUBLICATIONS

Gibbs and Weiller (1999) PNAS 96: 8022-8027.*
LaVallie et al (1993) Nat. Biotechnol. 11, 187-193.*
Notification Concerning Transmittal of International Preliminary Report on Patentability for corresponding PCT application No. PCT/US2006/030941, mailed Jul. 17, 2008.
Notification of Transmittal of the International Search Report and the Written Opinion of the International Searching Authority, or the Declaration for corresponding PCT application No. PCT/US2006/030941, mailed Sep. 24, 2007.
First Office Action corresponding to Indian Application No. 754/DELNP/2008 issued Jun. 27, 2013.

* cited by examiner

*Primary Examiner* — David T Fox
*Assistant Examiner* — Steven Bernacki
(74) *Attorney, Agent, or Firm* — Myers Bigel Sibley & Sajovec, P.A.

(57) ABSTRACT

Polypeptides and fusion proteins that bind to eukaryotic viruses, in particular, eukaryotic single-stranded DNA (ssDNA) viruses are provided. The polypeptides and fusion proteins bind to the replication initiation proteins (Rep) of ssDNA viruses and optionally inhibit viral replication and/or viral infection. The virus can be a plant pathogen or animal pathogen. Consensus sequences used to identify polypeptides that bind to eukaryotic viruses are also provided.

26 Claims, 11 Drawing Sheets

Motif 24 (g/s)CXLCXl

Motif 24    Interfering

```
SEQ ID NO:25 (1)  -------CRTRGCgCHLCRmLSQFTGG--------------------------
SEQ ID NO:27 (1)  -RDPQLGQVAQTWgCRLCLlE--------------------------------
SEQ ID NO:82 (1)  ---------GRGgCMLCDvDGSSAWLHTEGRLTGPITSQQCLSFQYLGNGEFIDG
SEQ ID NO:36 (1)  AKDVERGAGGKIKaCELCRl---------------------------------
SEQ ID NO:76 (1)  ---SSSPVPYSGGtCNLCsmRMW------------------------------
SEQ ID NO:17 (1)  ------------NECLiCHmLGIREFGLSA-----------------------
SEQ ID NO:81 (1)  ------------RsCVLCAyGSRTFNGSYLLF---------------------
```

Motif 24    Non Interfering

```
SEQ ID NO:16 (1)  --------------GFRAPGLSPTRPSCLiCSTL------------
SEQ ID NO:23 (1)  -------------------VPQPLNCDLCVLMGGASSSR-----
SEQ ID NO:24 (1)  ----------------RRDYRKFFALNCQLCRLTVT---------
SEQ ID NO:37 (1)  --------------VETFKARARQTPSCDLCPKT-----------
SEQ ID NO:40 (1)  ------------------RYRVSAGPLCSLCSlWGSVG-------
SEQ ID NO:59 (1)  -------------------VLGRLGGAGGCSLCDQLEAL-------
SEQ ID NO:61 (1)  -----------------RHESALHKSCELCYCPWKVC-------
SEQ ID NO:84 (1)  LVMGWRSEVSSLQGKTGTGGGPTLRKCQLCRGSRYTLKYYPC--
SEQ ID NO:87 (1)  -----------------------RRCMLCTSDKPGGDQGALNM
SEQ ID NO:85 (1)  ------------------------RPGCPfCTSWRCG--------
SEQ ID NO:93 (1)  --------------TPSVTWLAEWCSCVfCRDAS-----------
```

FIG. 9

Motif 1

```
SEQ ID NO:60   (1)  ----------IWInPNGLWWTKVG1NPYAV
SEQ ID NO:29   (1)  --------LQYSWNLYSVASfKTRRvSS---
SEQ ID NO:77   (1)  ----------EWEdPQYAGWELFSiSDLVH
SEQ ID NO:102  (1)  ----------AWDsESLATWASVMPWPYPT
SEQ ID NO:79   (1)  --------RAGWHeRVRQWWAIECtLEV--
SEQ ID NO:31   (1)  CYMEVEGRPRRWAdSFFvAW----------
```

Motif 4

```
SEQ ID NO:17   (1)  -----NeCLiCHMLGIREFGlSA
SEQ ID NO:25   (1)  CRTRGCgCHlCRMLSQFTGG---
SEQ ID NO:57   (1)  --ASLIgVGiASMHGMQTDGiY-
SEQ ID NO:38   (1)  --TELWWADfAKMHMEGGKGmC-
SEQ ID NO:55   (1)  -RERGGdDYRRMMHPGAASGP--
SEQ ID NO:66   (1)  RSYGGGeIPSVTMHCWIHCd---
```

Motif 20

```
SEQ ID NO:23   (1)  VPQPLNCDLCVLmGGASsSR-----------
SEQ ID NO:59   (1)  --------VLGRlGGAGGCSLCDQLEAl----
SEQ ID NO:89   (1)  ----------GmsGRIPEPDDWVVLFiTGC--
SEQ ID NO:53   (1)  ----------RlGGGRPKLWHFSPNLmAGF--
SEQ ID NO:47   (1)  --------------GGRQtEPSlTLLADlTLLLS
SEQ ID NO:99   (1)  ----CLDNLCWElGGGFPVILiHC---------
SEQ ID NO:66   (1)  --------RSYGGGEIPSVTmHCWIHCD----
SEQ ID NO:55   (1)  ---------RERGGDYRRMmHPGAASGP---
```

Motif 25

```
SEQ ID NO:29   (1)  --------LQysWNLYSvasfKTRRVSS---
SEQ ID NO:94   (1)  ---------SwWWANNSlCREWEFAC-----
SEQ ID NO:88   (1)  LWGGGTAWDFfvWGEDSaC------------
SEQ ID NO:100  (1)  --HVHGSCPSmgWSSNSWCsVF---------
SEQ ID NO:102  (1)  ----------aWDSESlatWASVMPWPYPT
SEQ ID NO:77   (1)  ---EWEDPQYagwELFSisdLVH
```

FIG. 10

Motif 27

```
SEQ ID NO:29   (1)  --------LQYswNLYSVASFKTRRVSS--
SEQ ID NO:27   (1)  ---------RdPQLgQVAqTWGCRLCLLE
SEQ ID NO:57   (1)  ---------AslIGvGiASMHGMQTDGIY
SEQ ID NO:90   (1)  GGTNALLQKVFfGEvGVASM---------
SEQ ID NO:64   (1)  ------SCDEafDAaSVASELFCQPY---
SEQ ID NO:95   (1)  ------WNMLafGGaLVASGLLRGWE---
SEQ ID NO:102  (1)  --------AWDsESLaTWASVMPWPYPT--
```

Motif 28

```
SEQ ID NO:70   (1)  ------VYEWgDVlCGGSMAIQWGL---
SEQ ID NO:74   (1)  -----RDAEWQDVlGRARAVHLRGR---
SEQ ID NO:102  (1)  AWDSESLATWaSVmPWPYPT--------
SEQ ID NO:69   (1)  ----------TWgLVcTGTGWGLLDTVVRA
SEQ ID NO:60   (1)  IWINPNGLWWtKVGLNPYAV--------
```

FIG. 10 (CONT'D.)

PEPTIDE APTAMERS THAT BIND TO THE REP PROTEINS OF SSDNA VIRUSES

RELATED APPLICATION DATA

The present application is a divisional of U.S. patent application Ser. No. 11/995,973 filed Jun. 23, 2008, now U.S. Pat. No. 8,168,748 (now allowed), which is a 35 U.S.C. §371 national phase application of PCT Application No. PCT/US2006/030941, filed Aug. 4, 2006, which claims the benefit of U.S. provisional application Ser. No. 60/705,426, filed Aug. 4, 2005, the disclosures of which are incorporated herein by reference in their entireties.

STATEMENT REGARDING ELECTRONIC FILING OF A SEQUENCE LISTING

A Sequence Listing in ASCII text format, submitted under 37 C.F.R. §1.821, entitled 5051-726DV_ST25.txt, 65,735 bytes in size, generated on Jan. 28, 2015 and filed via EFS-Web, is provided in lieu of a paper copy. This Sequence Listing is hereby incorporated by reference into the specification for its disclosures.

FIELD OF THE INVENTION

The present invention relates to products and methods for detecting viral infections and inhibiting viral replication and products resulting therefrom.

BACKGROUND OF THE INVENTION

Single-stranded DNA (ssDNA) viruses cause severe disease problems in plants and animals (Moffat (1999) *Science* 286:1835). Geminiviruses and nanoviruses infect many important crops worldwide, such as cassava, bean, pepper, tomato, sugar beet, cotton and maize (Brown and Bird (1992) *Plant Disease* 7:220-225; Czosnek and Laterrot (1997) *Arch. Virol.* 142:1391-1406; Lotrakul, et al. (1998) *Plant Dis.* 82:1253-1257; Zhou, et al. (1997) *J. Gen. Virol.* 78:2101-2111; Mansoor, et al. (1999) *Virology* 259:190-199; Polston, et al. (1999) *Plant Dis.* 83:984-988). Circoviruses cause significant disease losses among livestock and poultry (Allan, et al. (1998) *J. Vet. Diagn. Invest.* 10:3-10; Bassami, et al. (1998) *Virology* 249:453-9; Nayar, et al. (1999) *Can. Vet. J.* 40:277-8). A human circovirus in Hepatitis C patients has also been identified (Miyata, et al. (1999) *J. Virol.* 73:3582-3586; Mushahwar, et al. (1999) *Proc. Natl. Acad. Sci. USA.* 96:3177-3182). Even though these viruses have diverse host ranges and cause different diseases, they are highly related to each other.

Geminiviruses, nanoviruses, and circoviruses amplify their circular ssDNA genomes via a rolling circle mechanism through the combined action of a single viral protein, Rep, and the host DNA replication machinery (Laufs, et al. (1995) *Biochimie* 77:765-773; Mankertz, et al. (1997) *J. Virol.* 71:2562-2566; Katul, et al. (1998) *J. Gen. Virol.* 79:3101-3109; Mankertz, et al. (1998) *J. Gen. Virol.* 79:381-384; Hanley-Bowdoin, et al. (1999) *Crit. Rev. Plant Sci.* 18:71-106). Rep initiates plus-strand DNA synthesis by cleaving the viral origin within a hairpin structure at an invariant sequence, acts as a DNA ligase to terminate rolling circle replication, and hydrolyzes ATP. Because of the functional conservation, Rep proteins from all three ssDNA virus families are highly homologous.

The Geminiviridae family is classified into four genera based on genome structure, insect vector and type of host (Rybicki 1994; Briddon, Bedford et al. 1996). The four genera infect a broad range of plants and cause significant crop losses worldwide (Brown and Bird 1992; Brown 1994; Rybicki and Pietersen 1999; Morales and Anderson 2001; Mansoor, Briddon et al. 2003). All geminiviruses are characterized by twin icosahedral capsids (Zhang, Olson et al. 2001; Bottcher, Unseld et al. 2004) and single-stranded DNA (ssDNA) genomes that replicate through double-stranded DNA (dsDNA) intermediates (Hanley-Bowdoin, Settlage et al. 1999).

Geminiviruses replicate their small, circular DNA genomes using a combination of rolling circle and recombination-mediated replication (Gutierrez 1999; Jeske, Lutgemeier et al. 2001). They encode the proteins required for initiation of replication, Geminivirus Replication Initiation Protein (Rep), and depend on host polymerases for DNA synthesis (Gutierrez 2000; Hanley-Bowdoin, Settlage et al. 2004). Much of our knowledge of geminivirus replication comes from studies of TGMV, a typical begomovirus with a bipartite genome. Two of the seven proteins encoded by TGMV are involved in viral replication. AL1 is required for viral replication (Elmer, Brand et al. 1988; Hanley-Bowdoin, Elmer et al. 1990), whereas AL3 is an accessory factor that enhances viral DNA accumulation (Sunter, Hartitz et al. 1990). The AL1 protein shows conservation across all four genera. Different nomenclatures have been used to designate AL1, which is also known as Rep, AC1 or C1. As used herein, the Rep designation is employed because it is applicable to all geminiviruses.

Rep is a multifunctional protein that mediates both virus-specific recognition of its cognate origin (Fontes, Eagle et al. 1994) and transcriptional repression (Eagle, Orozco et al. 1994; Eagle and Hanley-Bowdoin 1997). Rep initiates and terminates (+) strand DNA synthesis within a conserved hairpin motif (Heyraud-Nitschke, Schumacher et al. 1995; Laufs, Traut et al. 1995; Orozco and Hanley-Bowdoin 1996). It also induces the accumulation of host replication factors in infected cells (Nagar, Pedersen et al. 1995). Rep binds to dsDNA at a repeated sequence in the origin (Fontes, Eagle et al. 1994; Fontes, Gladfelter et al. 1994), cleaves and ligates DNA within an invariant sequence of a hairpin loop (Laufs, Jupin et al. 1995; Orozco and Hanley-Bowdoin 1996), and is thought to unwind viral DNA in an ATP-dependent manner (Gorbalenya and Koonin 1993; Pant, Gupta et al. 2001). Rep interacts with itself and AL3 (Settlage, Miller et al. 1996). It binds to several host factors involved in DNA transactions, including the replicative clamp PCNA (Castillo, Collinet et al. 2003), the clamp loader RFC (Luque, Sanz-Burgos et al. 2002), histone H3 and a mitotic kinesin (Kong and Hanley-Bowdoin 2002). Rep also interacts with host regulatory factors, including the retinoblastoma protein (pRBR) which modulates the a cell cycle and differentiation (Xie, Suarezlopez et al. 1995; Grafi, Burnett et al. 1996; Ach, Durfee et al. 1997), a novel protein kinase (GRIK) associated with leaf development (Kong and Hanley-Bowdoin 2002), and Ubc9—a component of the sumoylation pathway (Castillo, Kong et al. 2004).

The functional domains of Rep have been mapped by deletion and mutational studies (FIG. 1). The N-terminal half of Rep contains overlapping domains for DNA cleavage/ligation, DNA binding, and protein interactions (Orozco, Miller et al. 1997; Orozco and Hanley-Bowdoin 1998). NMR spectroscopy revealed that the overlapping DNA binding/cleavage domains contain a β-sheet cluster that resemble other nucleic acid binding proteins (Campos-Olivas, Louis et al. 2002). The characterized Rep protein interactions fall into two classes—proteins that bind between amino acids 101-

180 (Kong, Orozco et al. 2000; Settlage, Miller et al. 2001) and those that bind between amino acids 134-180. (Orozco, Kong et al. 2000; Kong and Hanley-Bowdoin 2002). The putative DNA helicase domain is in the C-terminus (Gorbalenya and Koonin 1993; Pant, Gupta et al. 2001).

Rep contains several conserved amino acid and structural motifs (FIG. 1). Motifs I, II and III are characteristic of rolling circle initiators (Ilyina and Koonin 1992; Koonin and Ilyina 1992). Motif I (FLTY) is a determinant of dsDNA binding specificity (Chatterji, Chatterji et al. 2000; Arguello-Astorga and Ruiz-Medrano 2001). Motif II (HLH) is a metal binding site that may impact protein conformation and/or catalysis. Motif III (YxxKD/E) is the catalytic site for DNA cleavage with the hydroxyl group of the Y residue forming a covalent bond with the 5' end of the cleaved DNA strand (Laufs, Traut et al. 1995). The aromatic ring of the Y residue plays a role in dsDNA binding (Orozco and Hanley-Bowdoin 1998). The three motifs are exposed and in close proximity on the β-sheet surface in the Rep N-terminus (Campos-Olivas, Louis et al. 2002). Other conserved motifs include a sequence of near identity and unknown function immediately C-terminal of Motif III (Kong, Orozco et al. 2000), a helix-loop-helix motif that mediates pRBR binding (Arguello-Astorga, Lopez-Ochoa et al. 2004), and a NTP binding consensus (Walker, Saraste et al. 1982).

A variety of strategies have been applied to geminivirus resistance, including conventional breeding and transgenic approaches. Conventional breeding has been confounded by the limited sources of natural resistance, the multigenic nature of the resistance traits, and the time required for a breeding program (Miklas, Johnson et al. 1996; Pessoni, Zimmermann et al. 1997; Velez, Bassett et al. 1998; Welz, Schechert at al. 1998; Kyetere, Ming et al. 1999). TYLCV resistance genes have been introgressed from a wild *Lycopersicon* species (Pilowsky and Cohen 1990; Lapidot, Friedmann et al. 1997; Friedmann, Lapidot et al. 1998; Vidaysky and Czosnk 1998). This resistance is often unsatisfactory due to linkage with poor fruit quality, complex inheritance patterns, and the difficulty of transfer to commercial cultivars. Most conventional resistances collapse under early or severe infection pressure (Lapidot and Friedmann 2002). There is also evidence that host resistance genes are not equally effective against different geminiviruses (Pernet, Hoisington et al. 1999; Pernet, Hoisington et al. 1999), and many host genes only confer tolerance (Gilreath, Shuler at al. 2001; Lapidot, Friedmann et al. 2001; Gomez, Pinon et al. 2004). Tolerant plants, which support viral replication—albeit at lower levels, can serve as reservoirs for mutant and recombinant viruses that have the potential to overcome resistance.

Several transgenic strategies based on pathogen-derived resistance have also been tested. There is one report of transgenic tomatoes that contain a mutant begomovirus coat protein gene and display tolerance (Kunik, Salomon et al. 1994), but this result has not been reproduced by other researchers using wild type viral sequences (Azzam, Diaz et al. 1996; Sinisterra, Polston et al. 1999). Instead, expression of geminivirus sequences frequently results in the production of functional proteins that typically complement defective viruses or cause symptoms (Hanley-Bowdoin, Elmer et al. 1989; Hayes and Buck 1989; Hanley-Bowdoin, Elmer et al. 1990; Pascal, Goodlove et al. 1993; Latham, Saunders et al. 1997; Krake, Rezaian et al. 1998; Guevara-Gonzalez, Ramos at al. 1999; Hou, Sanders at al. 2000:Sunter, 2001 #7731). The reduced sensitivity to pathogen-derived resistance may reflect the lack of an RNA genomic form and the ability of geminiviruses to modulate host gene silencing (Ratcliff, Harrison et al. 1997; Voinnet, Pinto et al. 1999; Covey and AlKaff 2000; Noris, Lucioli et al. 2004; Vanitharani, Chellappan et al. 2004). Antisense RNA and defective-interfering replicon strategies have also been of limited success (Stanley, Fischmuth et al. 1990; Day, Bejarano et al. 1991; Frischmuth and Stanley 1994; Aragao, Ribeiro et al. 1998; Asad, Haris et al. 2003). Recent reports suggested that RNAi constructs can confer strong resistance, but this strategy is limited to homologous (or very closely related) geminiviruses (Pooggin, Shivaprasad et al. 2003; Pooggin and Hohn 2004). Transgenic plants that inducibly express dianthin upon geminivirus infection also display resistance (Hong, Saunders et al. 1996), but the safety of a toxic ribosome-inactivating protein has not been established. Expression of mutant begomovirus movement proteins in transgenic plants also resulted in resistance, but the phenotype is variable possibly because of the ability of the mutant proteins to confer symptoms in the absence of infection (Pascal, Goodbye et al. 1993; Duan, Powell et al. 1997; Duan, Powell et al. 1997; Hou, Sanders et al. 2000).

Unlike the strategies described above, Rep mutants have proven effective at interfering with geminivirus replication in cultured cells. Mutations in Motif III, the ATP binding site and the oligomerization domain (FIG. 1) interfere with virus replication in transient assays (Hanson and Maxwell 1999; Orozco, Kong et al. 2000; Chatterji, Beachy et al. 2001). However, plants that stably produce the Rep protein display de-velopmental defects (Brunetti, Tavazza et al. 1997; Brunetti, Tavazza et al. 2001), and expression is selected against during meiosis. The pRBR protein is required for gametogenesis (Ebel, Mariconti et al. 2004), suggesting that the Rep expression problem reflects its interaction with pRBR. Recent experiments showed that inclusion of a pRBR binding mutation in an interfering Rep transgene results in stable expression through at least 3 generations. Because Rep is highly specific for its cognate viral origin (Fontes, Gladfelter et al. 1994; Chatterji, Chatterji et al. 2000), the same plants were designed to also express a mutant AL3 in an effort to the broaden resistance. (AL3 functions in virus-nonspecific manner to enhance viral accumulation (Santer, Stenger et al. 1994; Sung and Coutts 1995)). The plants coexpressing the mutant Rep and AL3 proteins are immune to infection by the homologous virus through at least three generations. It is not yet known if they are resistant to unrelated begomoviruses. In contrast, other studies showed that infection with a homologous virus can lead to Rep transgene silencing. It is desirable to develop alternative resistance strategies.

Peptide aptamers resemble single chain antibodies, but because of their in vivo selection, are more likely to be stably expressed and correctly folded and to interact with their targets in an intracellular context (Crawford, Woodman et al. 2003). If an aptamer binds to residues critical for function, it can inactivate its target and interfere with cellular processes. For example, an aptamer that binds to the active site of the cell cycle regulator, cdk2, was isolated by screening a combinatorial peptide library in yeast dihybrid assays (Colas, Cohen et al. 1996). The aptamer blocks cdk2/cyclin E kinase activity in vitro and, when expressed in vivo, retards cell division (Cohen, Colas et al. 1998). An aptamer that interacts with the dimerization domain of cell cycle-associated transcription factor, E2F, also interferes with cell cycle progression in animal cells (Fabbrizio, LeCam et al. 1999). Aptamers have also been expressed in flies to study the specific roles of cdk1 and cdk2 during *Drosophila* organogenesis (Kolonin and Finley 1998). They have been used to distinguish between and selectively inactivate allelic variants of Ras and to inhibit Rho GTP exchange factors (Schmidt, Diriong et al. 2002; Xu and Luo 2002; Kurtz, Esposito et al. 2003) as well as interfere with the EGF signaling pathway, by binding to the downstream transcription factor Stat3 (Buerger, Nagel-Wolfrum et al. 2003; Nagel-Wolfrum, Buerger et al. 2004).

Peptide aptamers are especially well suited for targeting noncellular factors like viral proteins. An aptamer that binds to the hepatitis B virus core protein and inhibits viral capsid formation and replication has strong antiviral activity in liver cells (Butz, Denk et al. 2001). Aptamers that target the E6 or E7 proteins of human papillomavirus and block their anti-apoptotic activities result in specific elimination of HPV-positive cancer cells (Butz, Denk et al. 2000; Nauenburg, Zwerschke et al. 2001).

The present inventors have found that expression of aptamers that target essential, conserved Rep motifs can interfere with viral replication and confer broad resistance against geminivirus infection.

SUMMARY OF THE INVENTION

Single-stranded DNA (ssDNA) viruses cause severe disease problems in plants and animals. Geminiviruses and nanoviruses infect many important plant crops worldwide, whereas circoviruses cause significant disease losses among livestock and poultry. Even though these viruses have diverse host ranges and cause different diseases, their replication initiation proteins (Rep) are highly related to each other. The present invention can be used to develop a broad-based resistance strategy directed to eukaryotic viruses, in particular, eukaryotic ssDNA viruses.

A first aspect of the invention provides a polypeptide comprising, consisting essentially of or consisting of an amino acid sequence selected from the group consisting of: (a) the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO: 137, SEQ ID NO:138, SEQ ID NO:139, SEQ ID NO:140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:169, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, or any combination thereof;

A further aspect of the invention provides a fusion protein comprising the foregoing polypeptides.

Additional aspects of the invention provide an isolated nucleic acid comprising a nucleotide sequence encoding a polypeptide of the invention.

A further aspect of the present invention provides a vector or a cell comprising an isolated nucleic acid comprising a nucleotide sequence encoding the polypeptide comprising an amino acid sequence as recited above.

Further aspects of the present invention provide a transgenic plant comprising transformed plant cells, the transformed plant cells comprising the isolated nucleic, acids of the invention. A plurality of transgenic plants, such as a crop of transgenic plants, comprising the transformed plant cells described herein is also provided.

A further aspect of the invention provides a transgenic plant having increased resistance to a geminivirus infection, a viral variant thereof and mixed infections. A plurality of transgenic plants, such as a crop of transgenic plants, having increased resistance to a geminivirus infection, a viral variant thereof and mixed infections is also provided.

Also provided are methods of making transgenic plants having increased resistance to a virus infection, said method comprising providing a plant cell capable of regeneration, transforming the plant cell with an isolated nucleic acid comprising an isolated nucleic acid as described herein, and regenerating a transgenic plant from said transformed plant cell, wherein expression of the isolated nucleic acid to produce the polypeptide increases resistance of the transgenic plant to infection by a virus. Additional methods of making transgenic plants having increased resistance to a virus infection comprise introducing an isolated nucleic acid, as recited herein, into a cell to produce a transgenic plant, wherein expression of the isolated nucleic acid to produce the polypeptide increases resistance of the transgenic plant to infection by a virus.

Another aspect of the present invention provides a method of inhibiting viral replication in a plant cell comprising introducing an isolated nucleic acid, as recited herein, into the plant cell in an amount effective to inhibit virus replication.

The present invention further provides methods of detecting a viral infection, comprising: (a) contacting a sample with a polypeptide as recited above or a fusion protein as recited herein; and (b) detecting the presence or absence of binding between the polypeptide or fusion protein and a target, wherein the binding of the polypeptide or fusion protein to the target in the sample indicates the presence of a virus.

A further aspect of the present invention provides polypeptides identified through a method comprising identifying polypeptides that correspond to consensus peptide sequences derived from statistical analysis of a library of peptide sequences.

The invention further provides polypeptides that target a ssDNA virus replication initiation protein and interfere with the function of the replication initiation protein in vivo.

Further aspects of the invention provide a method of treating a viral infection in a subject in need thereof comprising administering a polypeptide according to embodiments of the present invention to the subject. The polypeptide can be formulated in a suitable pharmaceutical or agricultural carrier.

These and other aspects of the invention are set forth in more detail in the description of the invention below.

BRIEF DESCRIPTION OF THE DRAWINGS

FIG. 2A presents diagrams of the TGMV AL1 coding regions ($TAL1_{1-352}$ and $TAL1_{1-130}$) cloned downstream of the LexA DBD. Motifs I (SEQ ID NO:231), II and III (SEQ ID NO:232) associated with rolling circle replication initiator proteins are marked by the black boxes and their consensus are shown (Ilyina, T. V., and E. V. Koonin 1992. Conserved sequence motifs in the initiator proteins for rolling circle DNA replication encoded by diverse replicons from eubacteria, eucaryotes and archaebacteria. Nucleic Acids Res. 20:3279-3285; Koonin, E. V., and T. V. Ilyina. 1992. Geminivirus replication proteins are related to prokaryotic plasmid rolling circle DNA replication initiator proteins. J. Gen. Virol. 73:2763-2766). The oval corresponds to a conserved helix-loop-helix motif and the grey box is the ATP binding motif. In FIG. 2B, baits were tested for oligomerization activity using the positive (AD: $TAL1_{1-352}$) and the negative (AD:Jun) prey controls. The yeast transformants were [1] $TAL1_{1-352}$+AD:$TAL1_{1-352}$, [2] $TAL1_{1-352}$+AD:Jun, [3] $TAL1_{1-130}$ AD:$TAL1_{1-352}$, [4] $TAL1_{1-130}$+AD:Jun, [5] GUS+AD:$TAL1_{1-352}$, [6] GUS+AD:Jun, [7] $CaAL1_{1-349}$+AD:$TAL1_{1-352}$ and [8] $CaAL1_{1-349}$+AD:Jun. Interaction was monitored by growth on Gal-HWUL medium. Growth on Glu-HWU controlled for plasmid selection, whereas no growth on Glu-HWUL verified that interaction was dependent on induction of prey plasmid expression.

FIG. 3A presents a key for N-TrxA-peptides on the plates shown in FIGS. 3B-3D. Controls in column 12 are numbered as in FIG. 2. The interaction assay was performed on Gal-HWUL (B), Glu-HWUL (C) and Glu-HWU (D) media with the $TAL1_{1-130}$, $TAL1_{1-352}$ and GUS baits as indicated at the top. Peptides that interfere with replication of TGMV are boxed in FIG. 3A.

FIG. 4A presents a diagram showing the input replicon cassette, the released TGMV A replicon, and the plant expression cassettes. The positions of primers (LLp1 and LLp2) used to distinguish input vector and replicated DNA are marked. In FIG. 4B, tobacco protoplasts were cotransfected with a TGMV A replicon (pMON1565; lanes 1-4) and a plant expression cassette. Total DNA was isolated 36 h post transfection, digested with DpnI and XhoI, and analyzed on DNA gel blots using a virus-specific probe for double-stranded DNA accumulation (dsDNA). The expression cassettes correspond to the trans-dominant TAL1 mutant FQ118 (pNSB866; lane 1), an empty cassette (pMON921; lane 2), aptamer FL-42 (pNSB1136; lane 3) and aptamer FL-60 (pNSB1144; lane 4). In FIG. 4C, released DNA was amplified from E. coli transfected with an AL1 mutant replicon cassette. Total DNA was isolated from E. coli transformed with either a wild type TGMV A replicon cassette (pMON1565; lanes 1-3) or a mutant replicon cassette carrying an AU frame-shift mutation (pMON1679; lanes 4-6) and amplified using primers LLp1 and LLp2 in (A). The methylation status of the template DNAs was assessed by digestion with DpnI (lanes 2 and 5) and MboI (lanes 3 and 6). PCR products corresponding to the replicon cassette and released TGMV A DNA are marked. Markers corresponding to 100-bp (lane 7) and 1-kb (lane 8) DNA ladders are shown. As shown in FIG. 4D, TGMV A replication required full length AL1 in plant cells. Tobacco protoplasts were transfected with a wild type TGMV A replicon (pMON1565; lanes 1-9) or the mutant AL1 replicon cassette (pMON1679; lanes 10-12). In lanes 1-9, plant expression cassettes corresponding to an empty cassette (pMON921; lanes 1-3), the trans-dominant AL1 mutant FQ118 (pNSB866; lane 4-6) and the TrxA-GST control (pNSB1166; lanes 7-9) were included in the transfections. Total DNA was isolated 36 h post transfection and analyzed directly by PCR or after digestion with DpnI or MboI.

FIG. 6A provides a key for the aptamers on the plates in FIG. 6B. The negative prey control AD:Jun is marked by a "C". FIG. 6B provides results of yeast cells containing the selected aptamers and the $TAL1_{1-130}$ (left), $TAL1_{1-352}$ (center) and $CaAL1_{1-349}$ (right) baits were analyzed for growth on Gal-HWUL medium.

In FIG. 7B, the observed and expected means and standard errors of the pairwise alignments of the three TrxA peptide databases are given. The observed values for the three databases are significantly higher than the expected values derived from the random 20-mer databases (p values<0.0001).

FIG. 8A presents consensus sequences corresponding to motifs (Motif 1, SEQ ID NO:9; Motif 4, SEQ ID NO:10; Motif 20, SEQ ID NO:11; Motif 24, SEQ ID NO:12; Motif 25, SEQ ID NO:13; Motif 27, SEQ ID NO:14; and Motif 28, SEQ ID NO:15) identified in pairwise alignments of the 88 TrxA-peptides described herein. Bold typeface indicates invariant residues, normal typeface marks amino acids conserved in a majority of group members, and X represents any amino acid. The number of members and interfering peptides in each group are listed on the right. (See FIGS. 9 and 10 for sequence alignments). FIG. 8B provides WebLogo representation of Motif 24 (SEQ ID NO:12). The amino acid type and position is shown in the X-axis. The overall height plotted on the Y-axis of the amino acid stacks indicates the sequence conservation at a given position, while the height of individual symbols within a stack indicates the relative frequency of an amino acid at that position (Crooks G E, G. Hon, J. M. Chandonia, S. E. Brenner 2004. WebLogo: A sequence logo generator. Genome Res. 14:1188-1190; Schneider T. D., and R. M. Stephens 1990. Sequence Logos: A new way to display consensus sequences. Nucleic Acids Res. 18:6097-6100). Amino acids are color coded according to their type as basic (blue), hydrophobic (black), polar/non polar (green) and acidic (red) (Bogan, A. A., and K. S. Thorn 1998. Anatomy of hot spots in protein interfaces. J. Mol. Biol. 280:1-9; Glaser, F., D. Steinberg, I. Vakser, and N. Ben-Tal 2001. Residue frequencies and pairing preferences at protein-protein interfaces. Proteins 43:89-102).

FIG. 9 presents sequence alignment of Motif 24 peptides. Peptides containing Motif 24 were classified as interfering or non-interfering, and each class was aligned using Vector NTI-AlignX. Coding of amino acid similarities from Vector NTI-AlignX is: UPPERCASE normal—non-similar residues; UPPERCASE bold—a consensus residue derived from a block of similar residues; lowercase bold and shaded—a consensus residue derived from the occurrence of greater than 50% of a single residue; UPPERCASE bold and shaded—a consensus derived from a completely conserved residue; and lowercase bold—a residue weakly similar to a consensus residue at a given position.

FIG. 10 presents sequence alignments of selected motifs. Motifs 1, 4, 20, 25 and 27 include primarily interfering peptides (in bold). Motif 28 includes mostly noninterfering peptides (normal). Consensus color code presented above (FIG. 9).

DETAILED DESCRIPTION

Figure 1:
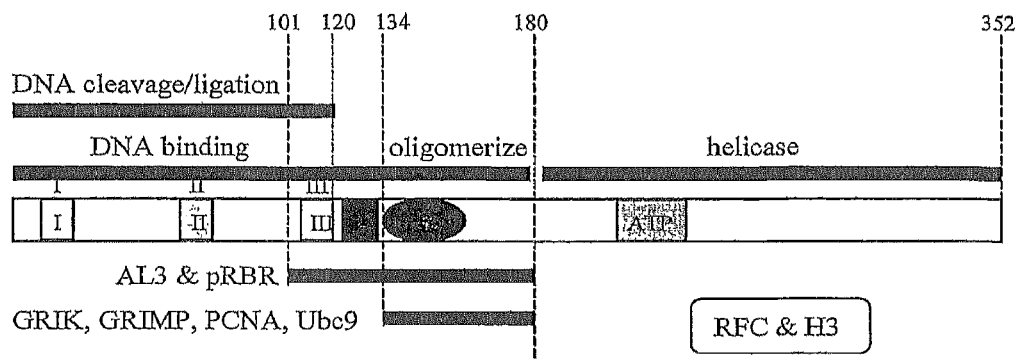
FIG. 1 depicts functional domains and motifs of the Rep protein. Motifs I, II and III are associated with rolling circle replication initiator proteins. The solid box is the conserved element of unknown function. The conserved helix-loop-helix motif marked by the oval provides the primary pRBR contacts. The box marked "ATP" is the NTP binding site of the putative DNA helicase domain. The limits of the functional domains for DNA cleavage/ligation, DNA binding, and known protein interaction sites are indicated. The PCNA binding site has been localized to the Rep N-terminus but has not been finely mapped. The RFC and H3 binding sites have not been mapped. The numbers at the top indicate amino acid positions in TGMV Rep.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Except as otherwise indicated, standard methods can be used for the production of viral and non-viral vectors, manipulation of nucleic acid sequences, production of transformed cells, and the like according to the present invention. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al., CURRENT PROTOCOLS IN MOLECULAR BIOLOGY (Green Publishing Associates, Inc. and John Wiley & Sons, Inc., New York).

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Also as used herein, "and/or" refers to and encompasses any and all possible combinations of one or more of the associated listed items, as well as the lack of combinations when interpreted in the alternative ("or").

As used herein, "aptamers" may be small peptide or nucleic acid molecules that specifically recognize and bind proteins, and in some instances, regulate a protein of interest, for example, decrease activity of the protein. In particular, peptide aptamers are recombinant proteins that have been selected for specific binding to a target protein (Hoppe-Seyler, Crnkovic-Mertens et al. 2004). They generally include a short peptide domain inserted into a supporting protein scaffold that enhances both specificity and affinity by conformationally constraining the peptide sequence (Colas, Cohen et al. 1996; Cohen, Colas et al. 1998; Buerger, Nagel-Wolfrum et al. 2003). Bacterial thioredoxin (Trx), which is rendered inactive by insertion of the peptide sequence into its active site, is the most commonly used scaffold because of its small size (12 kD), stability, solubility and known 3D structure. In some embodiments of the present invention, "aptamer" may be used to designate the peptide in the scaffold protein while "peptide" may refer to the inserted sequence.

"Amino acid sequence" as used herein, refers to an oligopeptide, peptide, polypeptide, or protein sequence, and fragment thereof, and to naturally occurring or partially or completely synthetic molecules. Where "amino acid sequence" is recited herein to refer to an amino acid sequence of a naturally occurring protein molecule, "amino acid sequence," and like terms, are not meant to limit the amino acid sequence to the complete, native amino acid sequence associated with the recited protein molecule.

A "functional fragment" of an amino acid sequence as used herein, refers to a portion of the amino acid sequence that retains at least one biological activity normally associated with that amino acid sequence.

In particular embodiments, a "functional variant" of an amino acid sequence as used herein, refers to no more than one, two, three, four, five, six, seven, eight, nine or ten amino acid substitutions in the sequence of interest. The functional variant retains at least one biological activity normally associated with that amino acid sequence. In particular embodiments, the "functional variant" retains at least about 40%, 50%, 60%, 75%, 85%, 90%, 95% or more biological activity normally associated with the full-length amino acid sequence. In other embodiments, a "functional variant" is an amino acid sequence that is at least about 60%, 70%, 80%, 90%, 95% 97% or 98% similar to the polypeptide sequence disclosed herein (or fragments thereof).

"Polypeptide" as used herein, is used interchangeably with "protein," and refers to a polymer of amino acids (dipeptide or greater) linked through peptide bonds. Thus, the term "polypeptide" includes proteins, oligopeptides, protein fragments, protein analogs and the like. The term "polypeptide" contemplates polypeptides as defined above that are encoded by nucleic acids, are recombinantly produced, are isolated from an appropriate source, or are synthesized.

"Fusion protein" as used herein, refers to a protein produced when two heterologous nucleotide sequences or fragments thereof coding for two (or more) different polypeptides, or fragments thereof, are fused together in the correct translational reading frame. The two or more different polypeptides, or fragments thereof, include those not found fused together in nature and/or include naturally occurring mutants.

"Isolated" nucleic acid as used herein, refers to a nucleic acid separated or substantially free from at least some of the other components of the naturally occurring organism or virus, such as for example, the cell or viral structural components or other polypeptides or nucleic acids commonly found associated with the nucleic acid. Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

"Vector" as used herein, refers to a viral or non-viral vector that is used to deliver a nucleic acid to a cell, protoplast, tissue or subject.

"Transgenic" as used herein, refers a plant that comprises a foreign nucleic acid incorporated into the genetic makeup of the plant, such as for example, by stable integration into the nuclear genome.

"Plant cell" as used herein, refers to plant cells, plant protoplasts and plant tissue cultures, plant calli, plant clumps, and plant cells that are intact in plants or parts of plants, such as leaves, pollen, embryos, cotyledon, hypocotyl, roots, root tips, anthers, flowers and parts thereof, ovules, shoots, stems, stalks, pith, capsules, and the like.

"Resistance to a virus infection" as used herein, refers to the reduced susceptibility of a plant or animal subject to viral infection as compared with a control susceptible plant or animal subject under conditions of infestation. "Resistance" can refer to reduced onset, severity, duration and/or spread of viral infection.

In embodiments of the present invention, a polypeptide comprises, consists essentially of or consists of: (a) the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ. ID NO:130, SEQ ID NO:131, SEQ ID NO:132, SEQ ID NO:133, SEQ ID NO:134, SEQ ID NO:135, SEQ ID NO:136, SEQ ID NO: 137, SEQ ID NO:138, SEQ ID NO:139, SEQ ID NO:140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, or any combination thereof; (b) a functional fragment of any of the amino acid sequences recited above that bind to a viral replication protein (Rep); and (c) a functional variant of any of the amino acid sequences of (a) or (b) that binds to a viral replication protein (Rep).

Moreover, polypeptides of the invention encompass those amino acids that have at least about 60%, 70%, 80%, 90%, 95%, 97%, 98% or higher amino acid sequence similarity with the polypeptide sequences specifically disclosed herein (or fragments thereof). As is known in the art, a number of different programs can be used to identify whether a nucleic acid or polypeptide has sequence identity or similarity to a known sequence. Sequence identity and/or similarity can be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48,443 (1970), by the search for similarity method of Pearson & Lipman, *Proc. Natl. Acad. Sci. USA* 85,2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux at al., *Nucl. Acid Res.* 12, 387-395 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351-360 (1987); the method is similar to that described by Higgins & Sharp, CABIOS 5, 151-153 (1989).

Another example of a useful algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology,* 266, 460-480 (1996); http://blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values can be adjusted to increase sensitivity.

An additional useful algorithm is gapped BLAST as reported by Altschul et al., (1997) *Nucleic Acids Res.* 25, 3389-3402. A percentage amino acid sequence identity value can be determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment can include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as, insertions, deletions, substitutions, etc.

The present invention also encompasses functional fragments of the polypeptides disclosed herein. A functional fragment of an amino acid sequence recited above retains at least one of the biological activities of the unmodified sequence, for example, binding to the Rep protein and/or inhibiting viral replication. In some embodiments, the functional fragment of the amino acid sequence retains all of the activities possessed by the unmodified sequence. By "retains" biological activity, it is meant that the amino acid sequence retains at least about 10%, 20%, 30%, 40%, 50%, 60%, 75%, 85%, 90%, 95%, 97%, 98%, 99%, or more, of one or more biological activities of the native amino acid sequence (and can even have a higher level of activity than the native amino acid sequence). A "non-functional" amino acid sequence is one that exhibits essentially no detectable biological activity normally associated with the amino acid sequence (e.g., at most, only an insignificant amount, e.g., less than about 10% or even 5%).

The invention further provides functional variants of the polypeptides disclosed herein. In particular embodiments, a functional variant of an amino acid sequence recited above has no more than one, two, three, four, five or six amino acid substitutions in the amino acid sequence of interest. In some embodiments, one, more than one, or all of the amino acid substitutions are conservative substitutions. In other embodiments, amino acid substitutions facilitate binding affinity of the polypeptide to the Rep protein and/or improve inhibitory properties. In other embodiments, a functional variant has no more than 1, 2, 3, 4, 5 or 6 amino acid substitutions, insertions and/or deletions in the amino acid sequence of interest. In general, those skilled in the art will appreciate that minor deletions, insertions or substitutions may be made to the amino acid sequences of peptides of the present invention without unduly adversely affecting the activity thereof. Thus, polypeptides containing such deletions or substitutions are a further aspect of the present invention. In polypeptides containing substitutions or replacements of amino acids, one or more amino acids of a polypeptide sequence may be replaced by one or more other amino acids wherein such replacement does not affect the function of that sequence. Such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function.

In particular embodiments, the functional fragment or variant comprises one or more of the conserved structural motifs of the polypeptides specifically disclosed herein (See FIGS. 7-10).

In some embodiments, the polypeptides bind anywhere in the Rep protein. In some other embodiments, the polypeptide binds to the catalytic domain for DNA cleavage of the Rep protein. Binding of the polypeptide to the Rep protein can occur in one or more DNA cleavage motifs (Motif I, Motif II and Motif III) located in the Rep N-terminus (FIG. 1). In certain embodiments, the polypeptide binds to Motif III within the catalytic domain for DNA cleavage. In other representative embodiments, the polypeptide binds to the DNA binding domain of the Rep protein or any other conserved region of the Rep protein (e.g., the N-terminal portion). In still other embodiments, the polypeptide binds to the Rep protein and further inhibits viral replication.

The polypeptides and fusion proteins can bind to a viral Rep protein and optionally inhibit replication and/or infection. The viruses can include any single-stranded eukaryotic DNA virus employing a rolling circle replication mechanism. In representative embodiments, the virus is a plant pathogen or an animal pathogen. In certain embodiments, the virus is a geminivirus, a nanovirus, or a circovirus. In some embodiments, viral infection can be caused by a combination of viruses, i.e., is a mixed infection. In some embodiments, the virus is a tomato golden mosaic virus (TGMV), a cabbage leaf curl virus (CbLCV) or a combination thereof.

Infectious clones for a variety of geminiviruses, nanoviruses and circoviruses are available in the art. See, e.g., Table 1, which provides sequences for geminivirus, nanovirus and circovirus type members. The nucleic acid sequences of other infectious clones are available at http://www.ncbi.nlm.nih.gov/ICTVdb/Ictv/fr-fst-g.htm. See also Hill et al., *Virology* 250, 283-292 (1998); Kong and Hanley-Bowdoin, *Plant Cell* 14, 1817-1832 (2002) (CbLCV); Sangare et al., *Mol Breeding* 5, 95-102 (1999) (ACMV and EACMV); Petty et al., *Virology* 277, 429-438 (2000); Hanley-Bowdoin, *Plant Cell* 1, 1057-1067 (2002) (TGMV); and Kunik et al., *Bio-Technology* 12, 500-504 (1994) (TYLCV).

bind to the target with higher affinity as compared to polypeptides wherein conformation is random. In some embodiments, the fusion protein comprises thioredoxin (or a fragment thereof). In still other embodiments, the fusion proteins binds to Rep and/or inhibits viral replication. In certain embodiments, the fusion protein reduces geminivirus replication.

Embodiments of the present invention further provide an isolated nucleic acid comprising, consisting essentially of or consisting of a nucleotide sequence encoding the polypeptides and fusion proteins of the invention. In some embodiments, the isolated nucleic acid comprises a nucleotide sequence encoding the polypeptide recited above. The nucleic acid can be DNA, RNA or a chimera thereof, and can further include naturally occurring bases and/or analogs and derivatives of naturally occurring bases. Further, the isolated nucleic acid can be double-stranded, single-stranded or a combination thereof.

In other embodiments, the present invention further provides a vector comprising the isolated nucleic acid recited above. In particular embodiments, the vector is an expression vector. In other particular embodiments, the vector is compatible with bacterial, yeast, animal (e.g., mammalian, insect) or plant (e.g., monocot, dicot) cells. Exemplary vectors include but are not limited to plasmids (including the Ti plasmid from *Agrobacteria*), virus vectors, bacterial artificial chromosomes, yeast artificial chromosomes, bacteriophage and the like.

Also provided are cells comprising the isolated nucleic acids, vectors, polypeptides and fusion proteins of the invention. The cell can be any cell known in the art including plant cells and protoplasts, animal cells, bacterial cells, yeast cells, and the like. Further, in particular embodiments, the cell can be a cultured cell or a cell in an intact plant or subject in vivo.

Exemplary Viruses

1. Geminivirus

The geminiviruses are single-stranded plant DNA viruses. They possess a circular, single-stranded (ss) genomic DNA encapsidated in twinned "geminate" icosahedral particles. The encapsidated ssDNAs are replicated through circular

TABLE 1

Biological information for geminivirus, nanovirus and circovirus type members

| Family | Genus | Type Species | Abbrev | ICTV virus code | Motif 3 | NCBI Acc. No. |
|---|---|---|---|---|---|---|
| Geminiviridae | Mastrevirus | Maize streak virus | (MSV) | 00.029.0.01.001. | VRDYILKEPL | Y00514 |
| | Curtovirus | Beet curly top virus | (BCTV) | 00.029.0.02.001 | VKSYVDKDGD | X04144 |
| | Begomovirus | Bean golden mosaic virus | (BGMV-PR) | 00.029.0.03.001 | VKEYIDKDGV | M10070 |
| | Topocuvirus | Tomato pseudo-curly top virus | (PCTV) | 00.029.0.04.001 | VNSYVDKDGD | X84735 |
| Circoviridae | Circovirus | Porcine circovirus type 1 | (PCV1) | 00.016.0.01.001 | NKEYCSKEGH | U49186 |
| | Gyrovirus | Chicken anaemia virus | (CAV) | 00.016.0.02.001 | NLTYVSKIGG | M55918 |
| Nanoviridae | Nanovirus | Subterranean clover stunt virus | (SCSV) | 00.093.0.01.001. | AQLYAMKEDS | U16730 |
| | Babuvirus | Banana bunchy top virus | (BBTV) | 00.093.0.02.001. | ARSYCMKEDT | S56276 |

Motif III sequences of virus type members Rep proteins. Motif III sequences of Rep proteins from geminiviruses, nanoviruses and circoviruses are shown. The invariant Y and K residues are in bold type. Geminiviruses are subgrouped as begomoviruses, curtoviruses, topocuviruses or mastreviruses. See *Virus Taxonomy: The Seventh Report of the International Committee on Taxonomy of Viruses* M.H. van Regenmortel, C.M. Fauquet, D.H.L. Bishop et al. (eds.) Academic Press, 1024 pp. (2000) San Diego, Wien New York.

In still other embodiments, the invention provides a fusion protein comprising, consisting essentially of or consisting of the polypeptide recited above. In some embodiments, the polypeptide conformation is constrained. In certain embodiments, polypeptides wherein conformation is constrained can double stranded DNA intermediates in the nucleus of the host cell, presumably by a rolling circle mechanism. Viral DNA replication, which results in the synthesis of both single and double stranded viral DNAs in large amounts, involves the expression of only a small number of viral proteins that are necessary either for the replication process itself or facilitates replication or viral transcription. The geminiviruses therefore appear to rely primarily on the machinery of the host for viral replication and gene expression.

Geminiviruses are subdivided on the basis of host range in either monocots or dicots and whether the insect vector is a leaf hopper, tree hopper or a whitefly species. Monocot-infecting geminiviruses, the mastreviruses, are transmitted by leaf hoppers and their genome comprises a single ss DNA component about 2.7 kb in size (monopartite geminivirus). This type of genome, the smallest known infectious DNA, is typified by wheat dwarf virus, which is one of a number from the subgroup that have been cloned and sequenced. A few mastreviruses infect dicot species as illustrated by bean yellow dwarf virus. Members of the geminivirus begomovirus genus infect dicot hosts and are transmitted by the whitefly. Many possess a bipartite genome comprising similarly sized DNAs (usually termed A and B) as illustrated by African cassava mosaic virus (ACMV), tomato golden mosaic virus (TGMV) and potato yellow mosaic virus. For successful infection of plants, both genomic components are required. Some begomoviruses possess single component genomes, as illustrated by tomato yellow leaf curl virus (TYLCV). Some single-component begomoviruses are associated with satellite DNAs, as illustrated by tomato leaf curl virus (TYLC). The curtoviruses, typified by beet curly top virus, occupy a unique intermediary position between the above two genera as they infect dicots but are transmitted by leaf hoppers. The fourth geminivirus genus, the topocuviruses, is comprised of a single virus, tomato pseudo-curly top virus, which has single component genome and is transmitted by tree hoppers.

The bipartite geminiviruses contain only the viruses that infect dicots. Exemplary is the African Cassava Mosaic Virus (ACMV) and the Tomato Golden Mosaic Virus (TGMV). TGMV, like ACMV, is composed of two circular DNA molecules of the same size, both of which are required for infectivity. Sequence analysis of the two genome components reveals six open reading frames (ORFs); four of the ORFs are encoded by DNA A and two by DNA B. On both components, the ORFs diverge from a conserved 230 nucleotide intergenic region (common region) and are transcribed bidirectionally from double stranded replicative form DNA. The ORFs are named according to genome component and orientation relative to the common region (i.e., left versus right). The AL2 gene product transactivates expression of the TGMV coat protein gene, which is also sometimes known as "AR1". Functions have not yet been attributed to some of the ORFs in the geminivirus genomes. However, it is known that certain proteins are involved in the replication of viral DNA (REP genes). See, e.g., Elmer et al., *Nucleic Acids Res.* 16, 7043 (1988); Hatta and Francki, *Virology* 92, 428 (1979).

The A genome component contains all viral information necessary for the replication and encapsidation of viral DNA, while the B component encodes functions required for movement of the virus through the infected plant. The DNA A component of these viruses is capable of autonomous replication in plant cells in the absence of DNA B when inserted as a greater than full-length copy into the genome of plant cells, or when a copy is electroporated into plant cells. In monopartite geminivirus genomes, the single genomic component contains all viral information necessary for replication, encapsidation, and movement of the virus.

The geminivirus A component carries the Rep (also known as C1, AC1 or ALI), the AL2 (also known as C2 or TRAP), AL3 (also known as C3, AC3 or REN), and AR1 (also known as V1 or coat protein) sequences. The geminivirus B component carries the BR1 (also known as BV1) and BL1 (also known as BC1) sequences. Additionally, monopartite geminiviruses encode a protein that is homologous to the Rep protein of bipartite viruses.

As used herein, geminiviruses encompass viruses of the Genus Mastrevirus, Genus Curtovirus, Genus Topocuvirus and Genus Begomovirus. Exemplary geminiviruses include, but are not limited to, Abutilon Mosaic Virus, Ageratum Yellow Vein Virus, Bhendi Yellow Vein Mosaic virus, Cassava African Mosaic Virus, Chino del Tomato Virus, Cotton Leaf Crumple Virus, Croton Yellow Vein Mosaic Virus, Dolichos Yellow Mosaic Virus, Horsegram Yellow Mosaic Virus, Jatropha Mosaic virus, Lima Bean Golden Mosaic Virus, Melon Leaf Curl Virus, Mung Bean Yellow Mosaic Virus, Okra Leaf Curl Virus, Pepper Hausteco Virus, Potato Yellow Mosaic Virus, Rhynchosia Mosaic Virus, Squash Leaf Curl Virus, Tobacco Leaf Curl Virus, Tomato Australian Leaf Curl Virus, Tomato Indian Leaf Curl Virus, Tomato Leaf Crumple Virus, Tomato Pseudo-Curly Top Virus, Tomato Yellow Leaf Curl Virus, Tomato Yellow Mosaic Virus, Watermelon Chlorotic Stunt Virus, Watermelon Curly Mottle Virus, Bean Distortion Dwarf Virus, Cowpea Golden Mosaic Virus, Lupin Leaf Curl Virus, Solanum Apical Leaf Curling Virus, Soybean Crinkle Leaf Virus, Chloris Striate Mosaic Virus, Digitaria Striate Mosaic Virus, Digitaria Streak Virus, Miscanthus Streak Virus, Panicum Streak Virus, Pasalum Striate Mosaic Virus, Sugarcane Streak Virus, Tobacco Yellow Dwarf Virus, Cassava Indian Mosaic Virus, Serrano Golden Mosaic Virus, Tomato Golden Mosaic Virus, Cabbage Leaf Curl Virus, Bean Golden Mosaic Virus, Pepper Texas Virus, Tomato Mottle Virus, Euphorbia Mosaic Virus, African Cassava Mosaic Virus, Bean Calico Mosaic Virus, Wheat Dwarf Virus, Cotton Leaf Curl Virus, Maize Streak Virus, and any other virus designated as a Geminivirus by the International Committee on Taxonomy of Viruses (ICTV). In particular embodiments, the geminivirus is a Tomato Golden Mosaic Virus (TGMV), a Cabbage Leaf Curl Virus (CbLCV) or a combination thereof.

2. Nanovirus

Nanovirus Rep proteins differ from those of members of the Geminiviruses in being smaller (about 33 kDa), having a slightly distinct dNTP-binding motif and lacking the Rb-binding motif. Moreover, the Nanoviruses are distinct from Geminivirus particle morphology, genome size, number and size of DNA components, and mode of transcription. The Nanoviruses have a conserved nona-nucleotide motif at the apex of the stem-loop sequence, which is consistent with the operation of a rolling circle model for DNA replication.

As used herein, Nanoviruses include, but are not limited to, Banana Bunchy Top Virus (BBTV), Coconut Foliar Decay Virus, Faba Bean Necrotic Yellows Virus (FBNYN), Milk Vetch Dwarf Virus (MVDV), subterranean clover stunt virus (SCSV), and Ageratum yellow vein virus (AYVV) and any other virus designated as a Nanovirus by the International Committee on Taxonomy of Viruses (ICTV).

3. Circovirus

Circoviruses infect animal species and are characterized as round, non-enveloped virions with mean diameters from 17 to 23.5 nm containing circular ssDNA. The ssDNA genome of the circoviruses represent the smallest viral DNA replicons known. As disclosed in WO 99/45956, at least six viruses have been identified as members of the family according to The Sixth Report of the International Committee for the Taxonomy of Viruses (Lukert, et al. (1995) *Arch. Virol.* 10 Suppl.: 166-168).

As used herein, Circoviruses include, but are not limited to, members of the Circoviridae family including chicken anemia virus (CAV), beak and feather disease virus (BFDV), porcine circovirus type 1 (PCV1), porcine circovirus type 2 (PCV2) and pigeon circovirus and any other virus designated as a nanovirus by the ICTV. Embodiments of the present invention further provide a transgenic plant or plant cell comprising the isolated nucleic acid recited above. The plant or cell can be stably transformed with the isolated nucleic acid. Additionally, embodiments of the invention provide a plurality of plants or cells comprising the isolated nucleic acid recited above. In other representative embodiments, the isolated nucleic acid is flanked by a T-DNA border sequence, optionally by 5' and 3' T-DNA border sequences. In some embodiments, the invention provides a plant cell or plant comprising the polypeptides or fusion proteins of the present invention. In other embodiments, the invention provides a plurality of plant Cells or plants comprising the polypeptides or fusion proteins of the present invention.

Plants can be transformed according to the present invention using any suitable method known in the art. Intact plants, plant tissue, explants, meristematic tissue, protoplasts, callus tissue, cultured cells, and the like may be used for transformation depending on the plant species and the method employed. In a preferred embodiment, intact plants are inoculated using microprojectiles carrying a nucleic acid to be transferred into the plant. The site of inoculation will be apparent to one skilled in the art; leaf tissue is one example of a suitable site of inoculation. In some embodiments, intact plant tissues or plants are inoculated, without the need for regeneration of plants (e.g., from callus).

Exemplary transformation methods include biological methods using viruses and *Agrobacterium*, physicochemical methods such as electroporation, polyethylene glycol, ballistic bombardment, microinjection, floral dip method and the like.

In one form of direct transformation, the vector is microinjected directly into plant cells by use of micropipettes to mechanically transfer the recombinant DNA (Crossway, *Mol. Gen. Genetics* 202: 179 (1985)).

In another protocol, the genetic material is transferred into the plant cell using polyethylene glycol (Krens, et al. *Nature* 296, 72 (1982)).

In still another method, protoplasts are fused with minicells, cells, lysosomes, or other fusible lipid-surfaced bodies that contain the nucleotide sequence to be transferred to the plant (Fraley, et al., *Proc. Natl. Acad. Sci. USA* 79, 1859 (1982)).

DNA may also be introduced into the plant cells by electroporation (Fromm et al., *Proc. Natl. Acad. Sci. USA* 82, 5824 (1985)). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide and regenerate. One advantage of electroporation is that large pieces of DNA, including artificial chromosomes, can be transformed by this method.

Viral vectors include RNA and DNA viral vectors (e.g., geminivirus, badnavirus, nanoviruses and caulimovirus vectors).

Ballistic transformation typically comprises the steps of: (a) providing a plant tissue as a target; (b) propelling a microprojectile carrying the heterologous nucleotide sequence at the plant tissue at a velocity sufficient to pierce the walls of the cells within the tissue and to deposit the nucleotide sequence within a cell of the tissue to thereby provide a transformed tissue. In some particular embodiments of the invention, the method further includes the step of culturing the transformed tissue with a selection agent. In particular embodiments, the selection step is followed by the step of regenerating transformed plants from the transformed tissue. As noted below, the technique may be carried out with the nucleotide sequence as a precipitate (wet or freeze-dried) alone, in place of the aqueous solution containing the nucleotide sequence.

Any ballistic cell transformation apparatus can be used in practicing the present invention. Exemplary apparatus are disclosed by Sandford et al. (*Particulate Science and Technology* 5, 27 (1988)), Klein et al. (*Nature* 327, 70 (1987)), and in EP 0 270 356. Such apparatus have been used to transform maize cells (Klein et al., *Proc. Natl. Acad. Sci. USA* 85, 4305 (1988)), soybean callus (Christou et al., *Plant Physiol.* 87, 671 (1988)), McCabe et al., *BioTechnology* 6, 923 (1988), yeast mitochondria (Johnston et al., *Science* 240, 1538 (1988)), and *Chlamydomonas* chloroplasts (Boynton et al., *Science* 240, 1534 (1988)).

Alternatively, an apparatus configured as described by Klein et al. (*Nature* 70, 327 (1987)) may be utilized. This apparatus comprises a bombardment chamber, which is divided into two separate compartments by an adjustable-height stopping plate. An acceleration tube is mounted on top of the bombardment chamber. A macroprojectile is propelled down the acceleration tube at the stopping plate by a gunpowder charge. The stopping plate has a borehole formed therein, which is smaller in diameter than the microprojectile. The macroprojectile carries the microprojectile(s), and the macroprojectile is aimed and fired at the borehole. When the macroprojectile is stopped by the stopping plate, the microprojectile(s) is propelled through the borehole. The target tissue is positioned in the bombardment chamber so that a microprojectile(s) propelled through the bore hole penetrates the cell walls of the cells in the target tissue and deposit the nucleotide sequence of interest carried thereon in the cells of the target tissue. The bombardment chamber is partially evacuated prior to use to prevent atmospheric drag from unduly slowing the microprojectiles. The chamber is only partially evacuated so that the target tissue is not desiccated during bombardment. A vacuum of typically between about 400 to about 800 millimeters of mercury is suitable.

In alternative embodiments, ballistic transformation is achieved without use of microprojectiles. For example, an aqueous solution containing the nucleotide sequence of interest as a precipitate may be carried by the macroprojectile (e.g., by placing the aqueous solution directly on the plate-contact end of the macroprojectile without a microprojectile, where it is held by surface tension), and the solution alone propelled at the plant tissue target (e.g., by propelling the macroprojectile down the acceleration tube in the same manner as described above). Other approaches include placing the nucleic acid precipitate itself ("wet" precipitate) or a freeze-dried nucleotide precipitate directly on the plate-contact end of the macroprojectile without a microprojectile. In the absence of a microprojectile, it is believed that the nucleotide sequence must either be propelled at the tissue target at a greater velocity than that needed if carried by a microprojectile, or the nucleotide sequenced caused to travel a shorter distance to the target tissue (or both).

The nucleotide sequence can be carried on a microprojectile. The microprojectile may be formed from any material having sufficient density and cohesiveness to be propelled through the cell wall, given the particle's velocity and the distance the particle must travel. Non-limiting examples of materials for making microprojectiles include metal, glass, silica, ice, polyethylene, polypropylene, polycarbonate, and carbon compounds (e.g., graphite, diamond). Metallic particles are currently preferred. Non-limiting examples of suitable metals include tungsten, gold, and iridium. The particles should be of a size sufficiently small to avoid excessive disruption of the cells they contact in the target tissue, and sufficiently large to provide the inertia required to penetrate to the cell of interest in the target tissue. Particles ranging in diameter from about one-half micrometer to about three micrometers are suitable. Particles need not be spherical, as surface irregularities on the particles may enhance their DNA carrying capacity.

The nucleotide sequence may be immobilized on the particle by precipitation. The precise precipitation parameters employed will vary depending upon factors such as the particle acceleration procedure employed, as is known in the art. The carrier particles may optionally be coated with an encapsulating agents such as polylysine to improve the stability of nucleotide sequences immobilized thereon, as discussed in EP 0 270 356 (column 8).

Alternatively, plants may be transformed using *Agrobacterium tumefaciens* or *Agrobacterium rhizogenes*, preferably *Agrobacterium tumefaciens*. *Agrobacterium*-mediated gene transfer exploits the natural ability of *A. tumefaciens* and *A. rhizogenes* to transfer DNA into plant chromosomes. *Agrobacterium* is a plant pathogen that transfers a set of genes encoded in a region called T-DNA of the Ti and Ri plasmids of *A. tumefaciens* and *A. rhizogenes*, respectively, into plant cells. The typical result of transfer of the Ti plasmid is a tumorous growth called a crown gall in which the T-DNA is stably integrated into a host chromosome. Integration of the Ri plasmid into the host chromosomal DNA results in a condition known as "hairy root disease". The ability to cause disease in the host plant can be avoided by deletion of the genes in the T-DNA without loss of DNA transfer and integration. The DNA to be transferred is attached to border sequences that define the end points of an integrated T-DNA.

Gene transfer by means of engineered *Agrobacterium* strains has become routine for many dicotyledonous plants. Some difficulty has been experienced, however, in using *Agrobacterium* to transform monocotyledonous plants, in particular, cereal plants. However, *Agrobacterium* mediated transformation has been achieved in several monocot species, including cereal species such as rye (de la Pena et al., *Nature* 325, 274 (1987)), maize (Rhodes et al., *Science* 240, 204 (1988)), and rice (Shimamoto et al., *Nature* 338, 274 (1989)).

While the following discussion will focus on using *A. tumefaciens* to achieve gene transfer in plants, those skilled in the art will appreciate that this discussion also applies to *A. rhizogenes*. Transformation using *A. rhizogenes* has developed analogously to that of *A. tumefaciens* and has been successfully utilized to transform, for example, alfalfa, *Solanum nigrum* L., and poplar. U.S. Pat. No. 5,777,200 to Ryals et al. As described by U.S. Pat. No. 5,773,693 to Burgess et al., it is preferable to use a disarmed *A. tumefaciens* strain (as described below), however, the wild-type *A. rhizogenes* may be employed. An illustrative strain of *A. rhizogenes* is strain 15834.

The *Agrobacterium* strain is typically modified to contain the nucleotide sequences to be transferred to the plant. The nucleotide sequence to be transferred is incorporated into the T-region and is typically flanked by at least one T-DNA border sequence, preferably two T-DNA border sequences. A variety of *Agrobacterium* strains are known in the art, and can be used in the methods of the invention. See, e.g., Hooykaas, Plant Mol. Biol. 13, 327 (1989); Smith et al., *Crop Science* 35, 301 (1995); Chilton, *Proc. Natl. Acad. Sci. USA* 90, 3119 (1993); Mollony et al., *Monograph Theor. Appl. Genet NY* 19, 148 (1993); Ishida et al., *Nature Biotechnol.* 14, 745 (1996); and Komari et al., *The Plant Journal* 10, 165 (1996).

In addition to the T-region, the Ti (or Ri) plasmid contains a vir region. The vir region is important for efficient transformation, and appears to be species-specific.

Two exemplary classes of recombinant Ti and Ri plasmid vector systems are commonly used in the art. In one class, called "cointegrate," the shuttle vector containing the gene of interest is inserted by genetic recombination into a non-oncogenic Ti plasmid that contains both the cis-acting and trans-acting elements required for plant transformation as, for example, in the PMLJ1 shuttle vector of DeBlock et al., *EMBO J.* 3, 1681 (1984), and the non-oncogenic Ti plasmid pGV2850 described by Zambryski et al., *EMBO J.* 2, 2143 (1983). In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* 12, 8711 (1984), and the non-oncogenic Ti plasmid PAL4404 described by Hoekma, et al., *Nature* 303, 179 (1983).

Binary vector systems have been developed where the manipulated disarmed T-DNA carrying the heterologous nucleotide sequence of interest and the vir functions are present on separate plasmids. In this manner, a modified T-DNA region comprising foreign DNA (the nucleic acid to be transferred) is constructed in a small plasmid that replicates in *E. coli*. This plasmid is transferred conjugatively in a tri-parental mating or via electroporation into *A. tumefaciens* that contains a compatible plasmid with virulence gene sequences. The vir functions are supplied in trans to transfer the T-DNA into the plant genome. Such binary vectors are useful in the practice of the present invention.

Plant cells may be transformed with *Agrobacteria* by any means known in the art, e.g., by co-cultivation with cultured isolated protoplasts, or transformation of intact cells or tissues. The first generally utilizes an established culture system that allows for culturing protoplasts and subsequent plant regeneration from cultured protoplasts. Identification of transformed cells or plants is generally accomplished by including a selectable marker in the transforming vector, or by obtaining evidence of successful bacterial infection.

In plants stably transformed by *Agrobacteria*-mediated transformation, the nucleotide sequence of interest is incorporated into the plant genome, typically flanked by at least one T-DNA border sequence. In some embodiments, the nucleotide sequence of interest is flanked by two T-DNA border sequences.

Alternatively, transgenic plants may be produced using the well-established 'floral dip' method (See, e.g., Clough and Bent (1998) *Plant Journal* 16:735). In one representative protocol, plants are grown in soil until the primary inflorescence is about 10 cm tall. The primary inflorescence is cut to induce the emergence of multiple secondary inflorescences. The inflorescences of these plants are dipped in a suspension of *Agrobacterium* containing the vector of interest. After the dipping process, the plants are grown to maturity and the seeds are harvested. Transgenic seeds from these treated plants are selected by germination in soil under selective pressure (e.g., using the chemical bialaphos). Transgenic plants containing the selectable marker survive treatment and are transplanted to individual pots for subsequent analysis. See Bechtold, N. and Pelletier, G. Methods Mol Biol 82, 259-266 (1998); Chung, M. H. et al. Transgenic Res 9, 471-476 (2000); Clough, S. J. and Bent, A. F. Plant J 16, 735-743 (1998); Mysore, K. S. et al. Plant J 21, 9-16 (2000); Tague, B.

W. Transgenic Res 10, 259-267 (2001); Wang, W. C. et al. Plant Cell Rep 22, 274-281 (2003); Ye, G. N. et al. Plant J., 19:249-257 (1999).

Plant cells, which have been transformed by any method known in the art, can also be regenerated to produce intact plants using known techniques.

Plant regeneration from cultured protoplasts is described in Evans et al., *Handbook of Plant Cell Cultures*, Vol. 1: (Mac-Milan Publishing Co. New York, 1983); and Vasil I. R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues, including but not limited to, all major species of sugar-cane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

A large number of plants have been shown capable of regeneration from transformed individual cells to obtain transgenic whole plants.

The regenerated plants are transferred to standard soil conditions and cultivated in a conventional manner. The plants are grown and harvested using conventional procedures.

The particular conditions for transformation, selection and regeneration may be optimized by those of skill in the art. Factors that affect the efficiency of transformation include the species of plant, the tissue infected, composition of the media for tissue culture, selectable marker genes, the length of any of the above-described step, kinds of vectors, and light/dark conditions. Therefore, these and other factors may be varied to determine what is an optimal transformation protocol for any particular plant species. It is recognized that not every species will react in the same manner to the transformation conditions and may require a slightly different modification of the protocols disclosed herein. However, by altering each of the variables, an optimum protocol can be derived for any plant species.

The foregoing methods for transformation may be used for producing transgenic inbred or doubled-haploid lines. Transgenic inbred/doubled-haploid lines could then be crossed, with another (non-transformed or transformed) inbred or doubled-haploid line, in order to produce a transgenic hybrid plant. Alternatively, a genetic trait which has been engineered into a particular line using the foregoing transformation techniques could be moved into another line using traditional backcrossing techniques that are well known in the plant breeding arts.

Plants that may be employed in practicing the present invention include any plant (angiosperm or gymnosperm; monocot or dicot).

Exemplary plants include, but are not limited to corn (*Zea mays*), canola (*Brassica napus, Brassica rapa* ssp.), alfalfa (*Medicago saliva*), rice (*Oryza sativa*), rape (*Brassica napus*), rye (*Secale cereale*), sorghum (*Sorghum bicolor, Sorghum vulgare*), sunflower (*Helianthus annus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), apple (*Malus pumila*), blackberry (*Rubus*), strawberry (*Fragaria*), walnut (*Juglans regia*), grape (*Vitis vinifera*), apricot (*Prunus armeniaca*), cherry (*Prunus*), peach (*Prunus persica*), plum (*Prunus domestica*), pear (*Pyrus communis*), watermelon (*Citrullus vulgaris*). duckweed (*Lemna*), oats, barley, vegetables, ornamentals, conifers, and turfgrasses (e.g., for ornamental, recreational or forage purposes).

Vegetables include Solanaceous species (e.g., tomatoes; *Lycopersicon esculentum*), lettuce (e.g., *Lactuea sativa*), carrots (*Caucus carota*), cauliflower (*Brassica oleracea*), celery (*apium graveolens*), eggplant (*Solanum melongena*), asparagus (*Asparagus officinalis*), ochra (*Abelmoschus esculentus*), green beans (*Phaseolus vulgaris*), lima beans (*Phaseolus limensis*), peas (*Lathyrus* spp.), members of the genus. *Cucurbita* such as Hubbard squash (*C. Hubbard*), Butternut squash (*C. moschata*), Zucchini (*C. pepo*), Crookneck squash (*C. crookneck*), *C. argyrosperma, C. argyrosperma* ssp *sororia, C. digitata, C. ecuadorensis, C. foetidissima, C. lundelliana*, and *C. martinezii*, and members of the genus *Cucumis* such as cucumber (*Cucumis sativus*), cantaloupe (*C. cantalupensis*), and musk melon (*C. melo*).

Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*dianthus caryophyllus*), poinsettia (*Euphorbia pulcherima*), and chrysanthemum.

Conifers, which may be employed in practicing the present invention, include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

Turfgrass include, but are not limited to, zoysiagrasses, bentgrasses, fescue grasses, bluegrasses, St. Augustinegrasses, bermudagrasses, bufallograsses, ryegrasses, and orchardgrasses.

Also included are plants that serve primarily as laboratory models, e.g., *Arabidopsis*.

In some embodiments, the transgenic plant can be a tobacco plant, a potato plant, a soybean plant, a peanut plant, a tomato plant, a melon plant, a cassava plant, a bean plant, a squash plant, a maize plant, a cotton plant or a vegetable plant. In certain embodiments, the plant is a cassava plant. In still other embodiments, the present invention provides methods of providing resistance against a plant virus infection, in an agricultural field, comprising planting the field with a crop of plants as recited above. Accordingly, the present invention provides a plurality of transgenic plants, such as a crop, having a resistance against a plant virus infection and fields of grasses having the same.

Embodiments of the present invention further provide transgenic plants having increased resistance to a virus infection from viruses such as a geminivirus, a nanovirus and combinations thereof as compared to a non-transgenic control. Resistance may be evaluated by any suitable method known in the art, e.g., measuring inhibition of viral replication, detecting specific mutations within the genome of the viral agent, detecting and quantifying viral load and measuring surrogate markers of viral replication. The term "resistant/resistance" is not intended to indicate that the subject is absolutely immune from viral infection. Those skilled in the art will appreciate that the degree of resistance may be assessed with respect to a population of subjects or an entire field of plants. A subject may be considered "resistant" to viral infection if the overall incidence of infection is reduced, even if particular subjects may be susceptible to disease.

In some embodiments of the present invention, methods of making transgenic plants having increased resistance to a virus comprise introducing an isolated nucleic acid recited above into a plant cell to produce a transgenic plant, wherein expression of the isolated nucleic acid to produce the polypeptide increases resistance of the transgenic plant to infection by a virus. In particular embodiments, the present invention provides methods of making transgenic plants having increased resistance to a virus, wherein the method comprises providing a plant cell capable of regeneration; transforming the plant cell with an isolated nucleic acid comprising an isolated nucleic acid recited above; and regenerating a transgenic plant from that transformed plant cell, wherein expression of the isolated nucleic acid to produce the polypeptide increases resistance of the transgenic plant to infection by a virus. In some embodiments, the plant cell can be a tobacco plant cell, a potato plant cell, a soybean plant cell, a peanut plant cell, a tomato plant cell, a melon plant cell, a cassava plant cell, a bean plant cell, a squash plant cell, a maize plant cell, a cotton plant cell or a vegetable plant cell. In still other embodiments, the plant cell is stably transformed with the isolated nucleic acid. In certain embodiments, the plant cell is transformed by an *Agrobacterium*-mediated transformation method. In other embodiments, the plant cell is transformed by a biolistic transformation method.

In still other embodiments, the present invention provides methods of inhibiting viral replication in a plant cell (e.g., a cultured plant cell or protoplast or a plant cell in vivo) comprising introducing an isolated nucleic acid recited above into the plant cell in an amount effective to inhibit virus replication as compared to non-transgenic control. In some embodiments, virus replication is inhibited by at least about 10%, 20%, 30%, 40%, 50%, 60%, 75%, 85%, 90%, 95%, 97%, 98%, 99%, or more. In certain embodiments, the virus can be a geminivirus, a nanovirus and combinations thereof.

In still other embodiments, the invention provides methods of inhibiting viral replication in a plant cell by introducing a polypeptide or fusion protein of the invention into a plant cell. In still other embodiments, the invention provides a method of providing increased resistance to a viral infection comprising introducing a polypeptide or fusion protein of the invention into a plant.

A further embodiment of the present invention is a method of detecting a viral infection. The method can involve contacting a sample with at least one polypeptide of the present invention or a fusion protein thereof and detecting the presence or absence of binding between the polypeptide and a target, wherein the binding of the polypeptide to the target in the sample indicates the presence of a virus.

A sample is intended to include biological or environmental material, which may be suspected of containing a virus of the family Geminiviridae, Nanoviridae or Circoviridae. A sample suspected of containing a virus is one that may have come in contact with a virus or may be at risk of having or acquiring a virus. When the virus being detected is of the family Circoviridae (or other animal virus as described above), a sample may be blood, plasma, serum, cell products, cell line cultures, cell extracts, cerebrospinal fluid (CSF), tissue homogenates, urine, organs for transplantation, or semen isolated preferably from a bird, such as chicken or pigeon, or a pig. When the virus being detected is of the family Geminiviridae or Nanoviridae (or other plant viruses as described above), the sample may be a plant tissue culture, fruit, leaf, root, stem, or seed. A sample of environmental origin may include, but not be limited to, soil, water, and food samples including canned goods, meats, and animal fodder. It is contemplated that the method of the invention may be useful in detecting viral contaminants in an environmental sample, viral presence in an organ being used in a transplantation, or viral infection of plant seeds or tissue cultures.

Upon, binding of a polypeptide with its viral target, excess polypeptide and/or targets that do not bind said polypeptide may be removed by washing the sample so that bound polypeptide-target complexes are isolated. Subsequently, the presence or absence of binding (i.e., the presence or absence of polypeptide-target complexes) is measured or detected. To facilitate the step of detecting the presence of absence of binding, the polypeptide of the present invention can be labeled, preferably with a fluorescent or bioluminescent tag. Fluorochromes such as Phycocyanine, Allophycocyanine, Tricolor, AMCA, Eosin, Erythrosin, Fluorescein, Fluorescein Isothiocyanate Hydroxycoumarin, Rhodamine, Texas Red, Lucifer Yellow, and the like may be attached directly to a polypeptide of the invention through standard groups such as sulfhydryl or primary amine groups. Methods of imaging and analyzing any of the above-mentioned labels are well-known in the art and the method employed will vary with the type of analysis being conducted, i.e. individual samples or multiple sample analyses in high-throughput screens. Measurement of the label can be accomplished using flow cytometry, laser confocal microscopy, spectrofluorometer, fluorescence microscopy, fluorescence scanners and the like.

Further, a polypeptide of the present invention may be biotinylated and detection of a biotinylated polypeptide may be performed using any of the well-known avidin or streptavidin reagents. Detection of biotin-avidin or biotin-streptavidin complexes typically involves conjugated forms of avidin or streptavidin including, but are not limited to, enzyme-conjugates (e.g., alkaline phosphatase, β-galactosidase, glucose oxidase, horseradish peroxidase) or fluorescent-conjugates (e.g., 7-amino-4-methylcoumarin-3-acetic (AMCA), fluorescein, phycoerythrin, rhodamine, TEXAS RED®, OREGON GREEN®) or antibodies which specifically bind to avidin or streptavidin.

Antibodies which specifically interact with a polypeptide of the present invention can also be used in the detection of binding between said polypeptide and its target. As will be understood by one of skill in the art, a bound polypeptide-target complex is contacted with an antibody specific for said polypeptide and standard methods for detecting antibodies are employed for detecting binding of the antibody to the polypeptide-target complex, e.g., spectrofluorometer, fluorescence microscopy, immunocytochemistry, western blotting, ELISA, fluorescence scanners, and the like. Other methods for detecting antibodies are well-known to those of skill in the art (see, e.g., "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984) *J. Clin. Chem. Clin. Biochem.* 22:895-904).

Subsequently, the presence or absence of a bound polypeptide-target complex is then correlated with the presence or absence of a virus from which the target was derived.

As will be appreciated by one of skill in the art, the detection method of the invention may be used to detect one or more specific viruses, genera, or family of viruses depending on the specificity of the polypeptide being used.

In still other embodiments, the products of the present invention can be used for the preparation of a medicament, veterinary or agricultural product.

The present invention is applicable to animal, avian and plant subjects, where appropriate, for medicinal, diagnostic, drug screening, veterinary, or agricultural purposes. For example, geminiviruses and nanoviruses affect plants, circoviruses affect livestock and poultry, and a human circovirus has been identified in patients with Hepatitis C. Animal subjects include, but are not limited to, humans, primates, canines, felines, bovines, caprines, equines, ovines, porcines, rodents (e.g. rats and mice), lagomorphs, and the like, and mammals in utero. Avian subjects include, but are not limited to, chickens, ducks, turkeys, geese, quail, pheasant, ratites (e.g., ostrich) and domesticated birds (e.g., parrots and canaries), and birds in ovo. Plant subjects are described above.

Methods of the present invention can be carried out in a manner suitable for administration or application to the suitable subject. Administration to a plant or a plant cell is described above. Additionally, an isolated nucleic acid vector, polypeptide or fusion protein of the present invention can be used to formulate pharmaceutical compositions comprising a vector of the invention in a pharmaceutically acceptable carrier and/or other medicinal agents, pharmaceutical agents, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In general, a "physiologically acceptable carrier" is one that is not toxic or unduly detrimental to cells. Exemplary physiologically acceptable carriers include sterile, pyrogen-free water and sterile, pyrogen-free, phosphate buffered saline. physiologically acceptable carriers include pharmaceutically acceptable carriers.

By "pharmaceutically acceptable" it is meant a material that is not biologically or otherwise undesirable, i.e., the material may be administered to a subject without causing any undesirable biological effects. Thus, such a pharmaceutical composition may be used, for example, in transfection of a cell ex vivo or in administering a viral particle or cell directly to a subject.

As used herein, the term "effective amount" refers to an amount of a compound or composition that is sufficient to produce the desired effect, which can be a therapeutic or agricultural effect, i.e., an effect on plant and plant matter as described herein. The effective amount will vary with the application for which the compound or composition is being employed, the subject, the age and physical condition of the subject, the severity of the condition, the duration of the treatment, the nature of any concurrent treatment, the pharmaceutically or agriculturally acceptable carrier used, and like factors within the knowledge and expertise of those skilled in the art. An appropriate "effective amount" in any individual case can be determined by one of ordinary skill in the art by reference to the pertinent texts and literature and/or by using routine experimentation. (See, for example for pharmaceutical applications, Remington, *The Science And Practice of Pharmacy* (20th Ed. 2000).

Dosages will depend upon the mode of administration, the disease or condition to be treated, the individual subject's condition, and can be determined in a routine manner. See e.g., Remington, *The Science And Practice of Pharmacy* (20th Ed. 2000).

In particular embodiments, more than one administration (e.g., two, three, four or more administrations) may be employed.

Exemplary modes of administration include oral, rectal, transmucosal, topical, transdermal, in utero (or in ovo), inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, administration may be by local rather than systemic manner, for example, in a depot or sustained-release formulation.

As used herein, the term "treat" refers to an action resulting in a reduction in the severity of the subject's condition or at least the condition is partially improved or ameliorated and/or that some alleviation, mitigation or decrease in at least one clinical symptom (or agricultural index for plants) is achieved and/or there is a delay in the progression of the condition and/or prevention or delay of the onset of the condition. Thus, the term "treat" refers to both prophylactic and therapeutic treatment regimes.

As used herein, the term "agriculturally acceptable carrier" refers to adjuvants, e.g., inert components, dispersants, surfactants, tackifiers, binders, etc. that are ordinarily used in agricultural formulation technology.

Having now described the invention, the same will be illustrated with reference to certain examples, which are included herein for illustration purposes only, and which are not intended to be limiting of the invention.

Example 1

Viruses

Geminivirus Rep proteins have been studied extensively, and many of the assays for studying this protein are well-established in the art. Consequently, geminiviruses were used to test the capacity of aptamers to interfere with ssDNA virus replication and infection in eukaryotes. The tomato golden mosaic virus (TGMV) and cabbage leaf curl virus (CbLCV) were primarily studied. TGMV is a bipartite geminivirus that infects solanaceous species and encodes a typical Rep protein. CbLCV has a bipartite genome and is a severe pathogen in *brassica*. CbLCV is representative of a small group of dicot-infecting geminiviruses that encode an atypical Rep protein. Other viruses such as ACMV, BCTV, EACMV, MSV, ToMoV and TYLCV may also be useful in the analysis of selected aptamers. For example, TYLCV is a monopartite geminivirus that causes significant losses in tomato crops through out the world. Genomic clones as well as replication and infectivity assays are well established for these viruses. Together, these viruses can be used to establish the efficacy and breadth of the aptamer resistance strategy for ssDNA viruses.

Example 2

Materials and Methods

A. Yeast Plasmids.

The bait and prey plasmids used in this study are listed in Table 2. pNSB1118, the bait plasmid for full-length TGMV AL1 (TAL1$_{1-352}$), was generated by cloning a 1.2-Kb fragment with NdeI (trimmed) and BamHI ends from pNSB736 (Orozco et al. (2000) J. Biol. Chem. 275:6114-6122) into pEG202 (Golemis and Brent (1992) Mol. Cell. Biol. 12:3006-3014) with BamHI and EcoRI (repaired) ends. The same fragment was also ligated into pHybLex/Zeo (Invitrogen) digested with PvuII and BamHI to create pNSB1089. The TAL1$_{1-352}$ coding sequence from pNSB1089 was introduced into pYESTrp2 (Invitrogen) as a SacI/XhoI fragment to give the prey plasmid pNSB970. The bait plasmid for truncated TAL1$_{1-130}$ (pNSB1162) was generated in two steps. First, an 895-bp EcoRI/BamHI fragment from pNSB603 (Orozco et al. (2000) J. Biol. Chem. 275:6114-6122) was ligated into the same sites of pNSB1118 to create pNSB1153. Then, pNSB1153 was digested with NotI, repaired with *E. coli* DNA polymerase (Klenow fragment) and religated to delete an 861-bp sequence encoding the TAL1 C-terminus. The bait plasmid (pNSB1122) for full-length CaLCuV ALA (CaAL1$_{1-349}$) was built by cloning a 1.2-Kb BamHI/XhoI fragment from pNSB909 (Kong and Hanley-Bowdoin (2002) Plant Cell 14:1817-1832) into the same sites of pEG202.

The β-glucuronidase coding sequence (GUS) from pMON10018 (Monsanto) was cloned into pEG202 as a 2.2-Kb BglII-NotI fragment to give the control bait plasmid pNSB1120. An EcoRI/NotI fragment encoding TrxA-GST from pNSB1166 (described below) was cloned into the same sites of pYESTrp2 to generate pNSB1172, a negative control prey plasmid.

TABLE 2

Yeast dihybrid plasmids

| Insert | Cloning vector | Yeast selection[a] | Plasmid |
|---|---|---|---|
| Bait (DBD) | | | |
| TAL1$_{1-352}$ | pEG202 | (−) Histidine | pNSB1118 |
| TAL1$_{1-130}$ | pEG202 | (−) Histidine | pNSB1162 |
| CaAL1$_{1-349}$ | pEG202 | (−) Histidine | pNSB1122 |
| GUS | pEG202 | (−) Histidine | pNSB1120 |

TABLE 2-continued

Yeast dihybrid plasmids

| Insert | Cloning vector | Yeast selection[a] | Plasmid |
|---|---|---|---|
| Prey (AD) | | | |
| TAL1$_{1-352}$ | pYESTrp2 | (−) Tryptophan | pNSB970 |
| Jun | pYESTrp2 | (−) Tryptophan | pYESTrp-Jun |
| TrxA-GST | pYESTrp2 | (−) Tryptophan | pNSB1172 |

[a](−) Histidine, medium lacking histidine; (−) Tryptophan, medium lacking tryptophan.

B. Plant Expression Plasmids

TrxA-peptide prey plasmids isolated in the TAL1$_{1-352}$ screen were digested with EcoRI-XbaI, and the resulting 412-bp fragments were gel purified and cloned into pMON921 (Fontes et al. (1994) J. Biol. Chem. 269:8459-8465). To eliminate the gel purification step during the cloning of aptamers derived from the AL1$_{1-130}$ screen, a polylinker was inserted into pMON921 and the β-lactamase gene was replaced by the aminoglycoside 3'-phosphotransferase (aphA) coding sequence, which confers kanamycin resistance. The polylinker was generated by ligating the annealed oligonucleotides LLp27 and LLp28 (Table 3) into pMON921 digested with BglII/BamH1 to create pNSB1208. A fragment carrying the aphA gene was amplified from pFGC5941 (Kerschen et al. (2004) FEBS Lett. 566:223-228) using the primers LLp29 and LLp30 (Table 3), digested with SmaI/AatII and cloned into pNSB1208 cut with DraI/AatII to generate pNSB1226. The N-TrxA peptides were cloned into pNSB1226 as EcoRI/BamHI fragments. N-TrxA aptamers with internal EcoRI or BamHI sites (N-3, N-71, N-99, N-123, N-149 and N-153) were cloned into pNSB1226 as PCR-generated EcoRI/SacI or SacI inserts using primers LLp41 and LLp42 (Table 3).

The TrxA-GST control was generated in two steps. First, the RsrII site in the active site of the thioredoxin coding sequence (TrxA) was reconstituted. Two fragments were generated using pJM-1 library DNA as template in PCR reactions with primer pairs LLp9/LLp16 and LLp15/LLp12 (Table 3.) The PCR products were digested with RsrII and ligated in vitro. The resulting 414-bp fragment was digested with EcoRI/BamHI and cloned into the same sites of pBSKSII(−) to give pNSB1151. Both constructs were sequenced to verify the integrity of the TrxA sequence. Oligonucleotides LLp55 and LLp56 (Table 3), carrying a 60-bp sequence of the glutathione S-transferase gene (GST), were annealed and ligated into RsrII site of pNSB1151, creating pNSB1166. An EcoRI/BamHI fragment from pNSB1166 was cloned into the same sites of pMON921 to generate pNSB1168. The expression cassette (pNSB866) corresponding to FQ118, a TAL1 trans-dominant negative mutant, has been described before (Orozco et al. (2000) J. Biol. Chem. 275:6114-6122).

TABLE 3

Oligonucleotides

| Oligo-nucleotide | Target | Sequence[a] | Application |
|---|---|---|---|
| LLp1 | 5'-AL1 TGMV A | GATGTTTGGCAACCTCCTCTAG | Replication |
| LLp2 | 3'-CP TGMV A | GGTCGTTCTTTACCGTTGCAGTAC | Replication |
| LLp9 | 5'-pJM-1 | TCAAT<u>GAGCTC</u>GGTCCTACCCTTATGATGTG | Cloning |
| LLp10 | 5'-pJM-1 | TTCACCTGACTGACGACAGT | Sequencing |
| LLp12 | 3'-pJM-1 | AT<u>GGATCC</u>AGGCCTCTGGCGAAGAAGTCC | Cloning |

TABLE 3-continued

Oligonucleotides

| Oligo-nucleotide | Target | Sequence<sup>a</sup> | Application |
|---|---|---|---|
| LLp13 | 5'-pMON921 | TCATTTCATTTGGAGAGGACACGC | Sequencing |
| LLp14 | 3'-pMON921 | CCAATGCCATAATACTCGAACTCA | Sequencing |
| LLp15 | TrxA-2 | TACAG<u>CGGTCCG</u>TGCAAAATGATCGCC | Cloning |
| LLp16 | TrxA-1 | <u>CGGACCG</u>CACCACTCTGCCCAG | Cloning |
| LLp27 | pMON921 | <u>GATCT</u>GAATTCGCGATCTAGAGAGCTCG | Cloning |
| LLp28 | pMON921 | <u>GATCC</u>GAGCTCTCTAGATCGCGAATTCA | Cloning |
| LLp29 | 5'-aphA | AATTC<u>GGACGTC</u>GCTCCGTCGATACTATGTTATACGCC | Cloning |
| LLp30 | 3'-aphA | ATGA<u>CCCGGGG</u>ACGCTCAGTGGAACGAAAACTCACG | Cloning |
| LLp39 | 5'-Npt II | GGCGATAGAAGGCGATGCGCTGCG | Replication |
| LLp40 | 3'-Npt II | TGCACGCAGGTTCTCCGGCCGCT | Replication |
| LLp41 | 5'-pJM-1 | AA<u>GAGCTCAGTA</u>CTCCTACCCTTATGATGTGCCA | Cloning |
| LLp42 | 3'-pJM-1 | TT<u>GAGCTC</u>CTCTGGCGAAGAAGTCCA | Cloning |
| LLp55 | 5'-GST 20mer | GTCCGGAGCTCCCTATACTAGGTTATTGGAAAATTAAGGGCCTTGTGCAACCCACTCG<u>CG</u> | Cloning |
| LLp56 | 3T-GST 20mer | GA<u>CCG</u>CGAGTGGGTTGCACAAGGCCCTTAATTTTCCAATAACCTAGTATAGGGAGCTC<u>CG</u> | Cloning |

<sup>a</sup>Nucleotides used to generate restriction sites for cloning are underlined.

C. Peptide Aptamer Screens

The pJM-1 library (Colas et al. (1996) Nature 380:548-550.) was amplified by transforming 5 μg plasmid DNA into 1×10$^{10}$ electro-competent *E. coli* DH10B cells (Invitrogen) and stored at −80° C. in 40 mL aliquots containing 5×10$^8$ UFC/mL (Geyer and Brent (2000) Methods Enzymol. 328:171-208). Plasmid DNA was extracted using a QIAfilter plasmid maxi kit according to the manufacturer's protocols (QIAGEN), *Saccharomyces cerevisiae* strains EGY48 (MAT his3 trp1 ura3-52 leu2::LexA6op-) and EGY191 (MAT his3 trp1 ura3-52 leu2::LexA2op-LEU2) were used for the library screens (Estojak et al. (1995) Mol. Cell. Biol. 15:5820-5829). Plasmid DNA (50 μg) from the library was transformed into the bait strains containing the lacZ, reporter plasmid pSH18-34 (Invitrogen; Estojak et al. (1995) Mol. Cell. Biol. 15:5820-5829; Golemis and Brent (1992) Mol. Cell. Biol. 12:3006-3014) and the corresponding bait plasmids, Transformants were plated on synthetic dropout medium lacking histidine, tryptophan, uracil and leucine and supplemented with galactose/raffinose (Gal-HWUL) after heat shock and a 4 h incubation at 30° C. in liquid medium containing galactose/raffinose and lacking histidine and uracil (Gal-HU, Golemis and Brent (1992) Mol. Cell. Biol. 12:3006-3014). Recovered yeast colonies were also grown in medium lacking histidine, tryptophan and uracil and supplemented with glucose (Glu-HWU) to repress library expression. Activation of the leucine and β-galactosidase reporters was confirmed in growth assays (Gal-HWUL) and filter lift assays (Gal-HWU), respectively (Geyer and Brent (2000) Methods Enzymol. 328:171-208). pJM-1 plasmids containing the selected aptamers were recovered using the lyticase protocol and QIAGEN miniprep columns. The plasmids were transformed into *E. coli* KC8 strain (Clontech Yeast Protocols Manual PT3024-1) and selected on minimal M9 medium lacking tryptophan. Recovered plasmids were transferred into *E. coli* DH5α for isolation and retransformed into the yeast baits strains to confirm specific activation with the TAL1$_{1-352}$ and TAL1$_{1-130}$ baits and not with the GUS bait. For these assays, 4 μl droplets of 1×10$^{-2}$ dilutions (OD$_{600}$ adjusted to 0.08-0.12) of fresh yeast colonies were plated onto Gal-HWUL medium and incubated at 30° C. for 3-6 days. For sequencing, DNA minipreps were performed using the R.E.A.L. Prep 96 plasmid kit and a Biorobot 9600 (QIAGEN). Sequencing was performed according to the BigDye® Terminator v3.1 method (Applied Biosystems) using a Perkin Elmer Prism 3700 96-capillary automated DNA sequencer.

D. Replication Interference Assays.

Protoplasts were isolated from *Nicotiana tabacum* (BY-2) suspension cells, electroporated and cultured according to published methods (Fontes et al. (1994) J. Biol. Chem. 269:8459-8465). For the replication interference assays (Orozco et al. (2000) J. Biol. Chem. 275:6114-6122), replicon DNA (2 μg) containing a partial tandem copy of TGMV A (pMON1565; Orozco and Hanley-Bowdoin. (1996) J. Virol. 270:148-158) was cotransfected with a plant expression cassette (40 μg). Viral DNA accumulation was monitored by either hybridization or semi-quantitative PCR. For the hybridization assays, total DNA was extracted 48 h post-transfection, digested with DpnI and XhoI, resolved on 1% agarose gels and probed with a $^{32}$P-labeled DNA corresponding to TGMV A. Double-stranded viral DNA accumulation was quantified by phosphorimager analysis in a minimum of three independent experiments.

For semi-quantitative PCR assays, BY-2 cells were harvested 36 h post-transfection and lysed by vortexing using 50 μL of glass beads in 400 μL lysis buffer (50 mM Tris-HCl pH 7.6, 100 mM NaCl, 50 mM EDTA, 0.5% SDS). The lysates were cleared by centrifugation at 14,000 g for 5 min and extracted using a QIAprep Spin Miniprep Kit according to the manufacturer protocols (QIAGEN). Total DNA was quantified by A260, and identical amounts were digested overnight with DpnI and subjected to PCR analysis using primers LLp1 and LLp2 (Table 3) for the TGMV A replicon. The amount (12.5-200 ng) of total DNA in the reactions was titrated for each experiment. pMON721 plasmid DNA (1 µg), which does not contain TGMV sequences (Lanahan et al. (1994) Plant Cell 6:521-530) was added to each PCR reaction as an internal control and amplified with primers LLp39 and LLp40 (Table 3). Bands were quantified using ImageJ software (Abramoff et al. (2004) Biophotonics International 11:36-42; Rasband, W. S. (2005) ImageJ. National Institutes of Health). PCR efficiency was standardized between reactions as a ratio of the band intensities corresponding to TGMV A DNA and the pMON721 control. Relative replication was determined as the ratio of the normalized intensity of each reaction versus the normalized intensity detected for protoplasts transfected with TGMV A replicon DNA and the empty expression cassette pMON921.

D. Sequence Alignments.

For each experimental database, the amino acid content of the peptide 20-mers was computed using a script aminocounter.pl that was coded using BioPerl Modules (Stajich et al. (2002) Genome Res. 12:1611-1618). Based on this information, 100 random databases of equivalent size and content were generated using the Perl script ranPEP.pl (Stajich et al. (2002) Genome Res. 12:1611-1618). The random and experimental peptide databases were formatted using NCBI formatdb.exe, and pairwise alignments were performed using the NCBI Basic Alignment Search Tool (BLASTP 2.2.10; Henikoff and Henikoff (1992) Proc. Natl. Acad. Sci. USA 89:10915-10919) with a modified BLOSUM62 matrix (Altschul et al. (1997) Nucleic Acids Res. 25:3389-3402). The modified matrix removed the stringent gap restriction and included similarities based in amino acid hydrophobicity and charge. An E value of 20 (scores of 10 bits or more) was used as cutoff for the alignments, which were recorded as the number of peptides with hits and the sum of hits for all 20-mers in each database. These frequencies were used to calculate the expected or observed mean and the standard error of the mean for each database, which were compared in one-way T-tests in JMP 5.1 (SAS). The pairwise alignments of the experimental databases were analyzed further using the Vector NTI AlignX module (Invitrogen) to identify potential consensus motifs.

Example 3

Yeast Dihybrid Library Screen

Geminivirus replication proteins contain several conserved motifs that are essential for function. To develop new approaches to study and modulate these proteins, the pJM-1 library for interacting peptides using the well-characterized TGMV replication protein designated here as TAL1 was screened. The pJM-1 library encodes *E. coli* thioredoxin (TrxA) with $2.9 \times 10^a$ random 20-mer peptides in its active site (Colas et al. (1996) Nature 380:548-550). The TrxA-peptides are fused to the SV40 nuclear localization signal, the *E. coli* B42 activation domain (AD) and the hemagglutinin epitope tag and are expressed from the yeast Gal1 promoter (Colas et al. (1996) Nature 380:548-550). For the screens, two types of TAL1 bait plasmids (FIG. 2A) were constructed. $TAL1_{1-352}$ encodes the full-length TAL1 protein fused to the *E. coli* LexA DNA binding domain (DBD). $TAL1_{1-130}$ specifies a LexA DBD fusion with the first 130 amino acids of TAL1, which includes the conserved Motifs I, II and III (FIG. 1). A bait ($CaAL1_{1-349}$) containing the LexA DBD fused to the full-length coding sequence of the Cabbage leaf curl virus (CaLCuV) replication protein designated here as CaAL1 was also constructed. GUS encoding a DBD: β-glucuronidase fusion as a negative control was employed.

Figure 2:
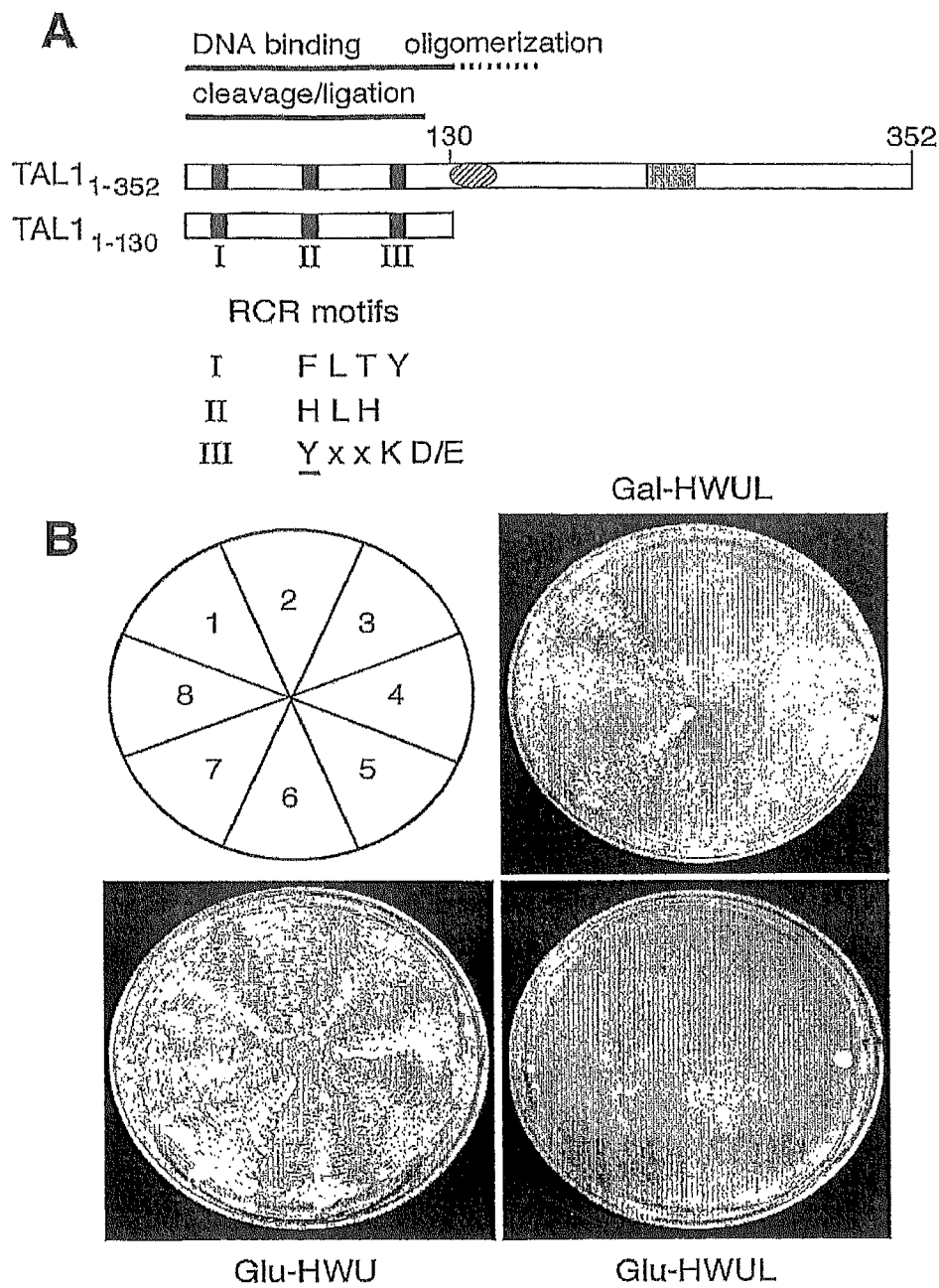
FIG. 2 presents baits for aptamer screens.
Figure 3:
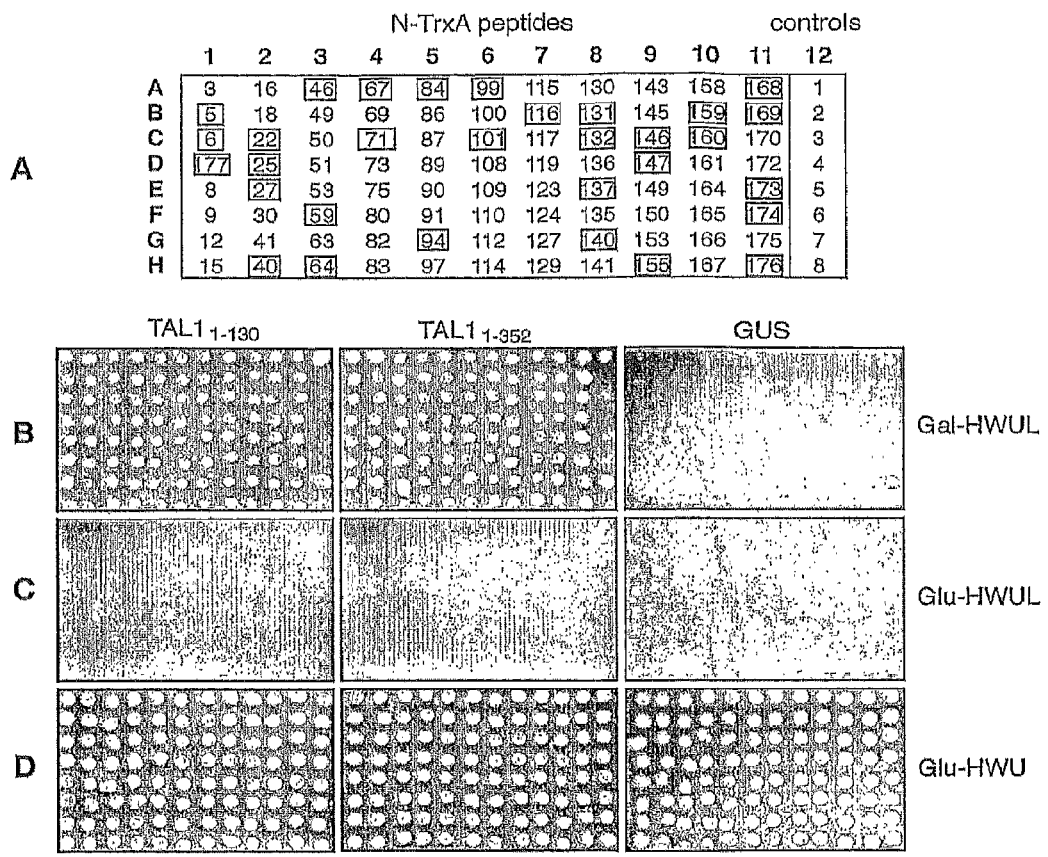
FIG. 3 shows that aptamers that bind to $TAL1_{1-130}$ also interact with $TAL1_{1-352}$. The 88 plasmids recovered from the screen of the JM-1 library using $TAL1_{1-130}$ as bait were retransformed into different bait strains to confirm specificity of interaction.
Figure 4:
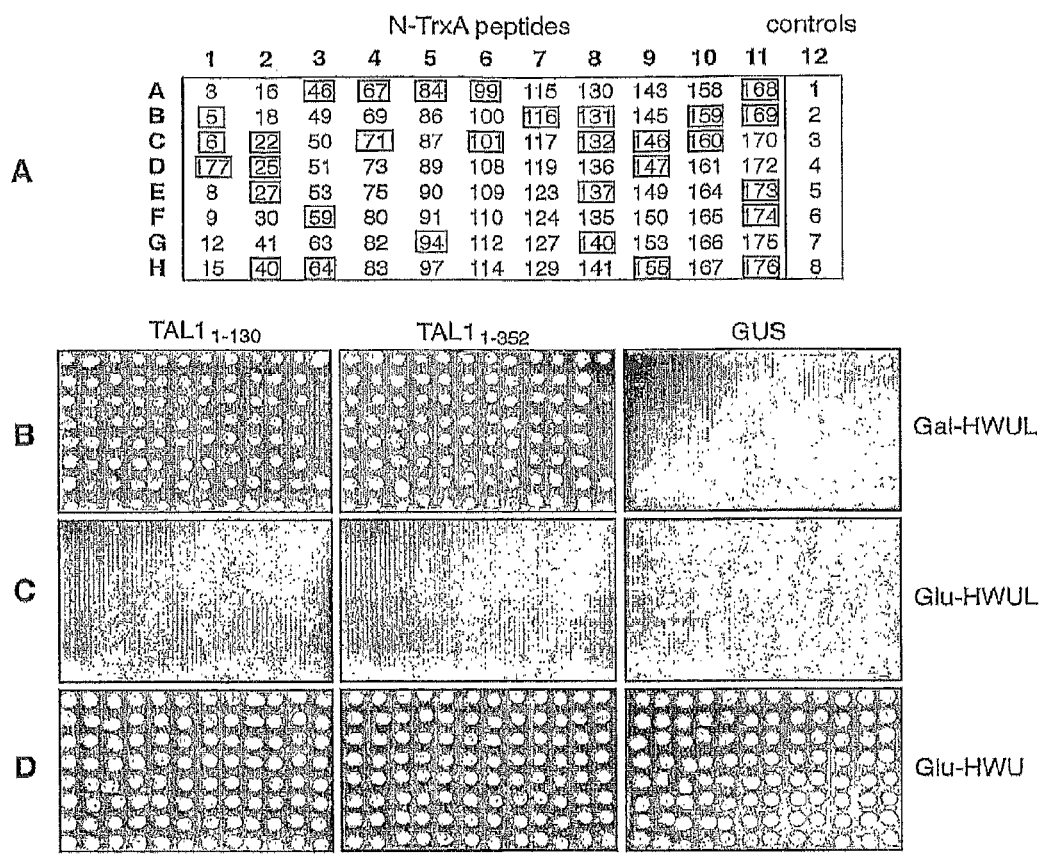
FIG. 4 shows results of replication interference assays.

The advantages of the oligomerization properties of TAL1 (Orozco et al. (2000) J. Biol. Chem. 275:6114-6122) were used to test the functionality of our full-length AL1 baits (FIG. 2A). Yeast carrying the $TAL1_{1-352}$ bait and AD:$TAL1_{1-352}$ prey plasmids were able to activate the Leu reporter in the presence of galactose (Gal-HWUL plates, FIG. 2B-1), consistent with the ability of full-length TAL1 to form oligomers. Transformants carrying the $CaAL1_{1-349}$ bait and AD:$TAL1_{1-352}$ prey plasmids also grew (FIG. 2B-7), indicating that the heterologous CaAL1 protein is able to interact with TAU. In contrast, no growth was observed for the $TAL1_{1-130}$ bait (FIG. 2B-3), which lacks the oligomerization domain (Orozco et al. (1997) J. Biol. Chem. 272:9840-9846), or the GUS bait (FIG. 2B-5) in cotransfection assays with the AD:$TAL1_{1-352}$ prey plasmid. None of the baits interacted with the AD:Jun (FIGS. 2B-2, 4, 6 and 8) or the AD:TrxA-GST prey plasmids (data not shown). All of the bait/prey combinations also failed to grow on selective medium supplemented with glucose (Glu-HWUL plates, FIG. 2B). The presence of the bait and prey plasmids in the transformants was verified by growth on Glu-HWU plates. Similar results were obtained when activation of the LacZ reporter was used to detect interactions (data not shown). Together, these data established the specificity of the $TAL1_{1-352}$ and $CaAL1_{1-349}$ interactions. These results also verified that interaction is dependent on galactose induction of prey plasmid expression, and that none of the bait plasmids autoactivate the yeast reporters.

A two-step transformation protocol was used for the two-hybrid screens of the pJM-1 library (Geyer and Brent (2000) Methods Enzymol. 328:171-208). The yeast strain EGY48 was first co-transformed with the LacZ reporter pSH18-34 and the $TAL1_{1-352}$ bait plasmid. The recovered bait strains were transformed with 50 µg of the library DNA. A total of $5 \times 10^6$ colonies were plated on selective media (Gal-HWUL) in 2 transformation events, resulting in the recovery of 350 colonies. These colonies were transferred to Glu-HWU plates, grown for 2 days to repress the library expression and re-evaluated for induction of the Leu and LacZ reporters on HWUL and HWU media supplemented with either galactose or glucose. Prey plasmids were recovered from 350 colonies that grew only in the presence of galactose. Retransformation assays using bait strains carrying $TAL1_{1-352}$ or GUS verified the specificity of interaction for 170 of the recovered plasmids, 40 of which were sequenced. Eleven TrxA-peptides with unique sequences and no stop codons or frameshifts were selected for further analysis (Table 4).

TABLE 4

Aptamers isolated in screens with $TAL1_{1-352}$

| Aptamer | Peptide sequence | Yeast plasmid[a] | Expression cassette[b] |
|---|---|---|---|
| FL-1 | PLSGRQGVHLYFLLLMPA | B1118-001 | pNSB1138 |
| FL-7 | FAVEYGSQGWGLWYCVWLDL | B1118-007 | pNSB1141 |

TABLE 4-continued

Aptamers isolated in screens with TAL1$_{1-352}$

| Aptamer | Peptide sequence | Yeast plasmid[a] | Expression cassette[b] |
|---|---|---|---|
| FL-18 | FQSRMGGGSGVVNAKLWAKE | B1118-018 | pNSB1137 |
| FL-19 | VASRDSGAWRELHSFLNFAS | B1118-019 | pNSB1135 |
| FL-41 | YYMALLYSQCPTVVLFRMTT | B1118-041 | pNSB1139 |
| FL-42 | DFVCLCLFACTSDLSAFRVC | B1118-042 | pNSB1136 |
| FL-57 | TAFRWDMFWMHTSGTWRKP | B1118-057 | pNSB1143 |
| FL-60 | FASGSGEPVGLGLGSPLEKL | B1118-060 | pNSB1144 |
| FL-70 | VYDSALCLVVGRCGLIRCR | B1118-070 | pNSB1134 |
| FL-90 | LVWASM | B1118-090 | pNSB1142 |
| FL-99 | LHESCWGWAGDSSPQGVLAG | B1118-099 | pNSB1140 |

[a]The yeast plasmids were cloned into pJM-1 with carbenicillin selection.
[b]The plant expression cassettes were cloned into pMON921 with carbenicillin selection.

To facilitate the identification of TrxA-peptides that inhibit the essential DNA binding and cleavage activities mediated by the N-terminus of AL1 (Orozco et al. 1997), the pJM-1 library with the TAL1$_{1-130}$ bait (FIG. 2A) was also screened. The screens were performed as described above for the TAL1$_{1-352}$ bait except for the use of the stringent yeast strain EGY191 to ensure the identification of high affinity interactions (Golemis and Brent (1992) Mol. Cell. Biol. 12:3006-3014). In this experiment, 597 positive candidates were isolated from a screen of $2\times10^7$ yeast colonies. Interaction with TAL1$_{1-130}$ was confirmed for 287 yeast colonies displaying activation of both the Leu and LacZ reporters. Prey plasmids were recovered and sequenced for 130 colonies, out of which 88 unique TrxA-peptides were selected (Table 5).

TABLE 5

Aptamers isolated in screens with TAL1$_{1-130}$

| Aptamer | Peptide sequence | Yeast plasmid[a] | Expression cassette[b] | Aptamer | Peptide sequence | Yeast plasmid[a] | Expression cassette[b] |
|---|---|---|---|---|---|---|---|
| A-3 | GFRAPGLSPTRPSCLICSTL | B1162-3 | pNSB1228 | A-114 | VRSHRRYQRNWEPVVSWFSS | B1162-114 | pNSB1279 |
| A-5 | NECLICHMLGIREFGLSA | B1162-5 | pNSB1229 | A-115 | WCGPQVSARCK | B1162-115 | pNSB1253 |
| A-6 | GTLWRRCASSWAFPPDCPSA | B1162-6 | pNSB1230 | A-116 | SCDEAFDAASVASELFCQPY | B1162-116 | pNSB1280 |
| A-8 | RRALRHCTGCMLSQRLGTAL | B1162-8 | pNSB1258 | A-117 | ARMALSLREWEYLFFKDAPSGPGL QGLSLASRLNLVILRGYG | B1162-117 | pNSB1228 |
| A-9 | HSMHSCSVGRCLVDVKVVVS | B1162-9 | pNSB1231 | | | | |
| A-12 | WMVCAGCGALRTRQVTLHPG | B1162-12 | pNSB1232 | A-119 | RSYGGGEIPSVTMHCWIHCD | B1162-119 | pNSB1281 |
| A-15 | GGFVPMRLCTCLLIVRLFI | B1162-15 | pNSB1264 | A-123 | SSSRWVPFALQDPLFSSDDW | B1162-123 | pNSB1282 |
| A-16 | VPQPLNCDLCVLMGGASSSR | B1162-16 | pNSB1233 | A-124 | YLWSSKMDEWVAMDDVYAAC | B1162-124 | pNSB1283 |
| A-18 | RRDYRKFFALNCQLCRLTVT | B1162-18 | pNSB1234 | A-127 | TWGLVCTGTGWGLLDTVVRA | B1162-127 | pNSB1284 |
| A-22 | CRTRGCGCHLCRMLSQFTGG | B1162-22 | pNSB1235 | A-129 | VYEWGDVLCGGSMAIQWGL | B1162-129 | pNSB1254 |
| A-25 | MRLGKGWNLMFLEEVSVLDA | B1162-25 | pNSB1323 | A-130 | ASNGEIAYCVEQAMLLLCFH | B1162-130 | pNSB1285 |
| A-27 | RDPQLGQVAQTWGCRLCLLE | B1162-27 | pNSB1259 | A-131 | ELIVHEWPLILSRVGRIVL | B1162-131 | pNSB1255 |
| A-30 | LVSESCGSWFCLCPWEVLNW | B1162-30 | pNSB1263 | A-132 | GRVQLEILVSEAEEGVSPFL | B1162-132 | pNSB1286 |
| A-40 | LQYSWNLYSVASFKTRRVSS | B1162-40 | pNSB1236 | A-135 | RDAEWQDVLGRARAVHLRGR | B1162-135 | pNSB1287 |
| A-41 | RLQESSIDLTPGIYLGMDFV | B1162-41 | pNSB1265 | A-136 | GLKWKSDNGCVYVSFMRGGV | B1162-136 | pNSB1288 |
| A-46 | CYMEVEGRPRRWADSFFVAW | B1162-46 | pNSB1262 | A-137 | SSSPVPYSGGTCNLCSMRMW | B1162-137 | pNSB1289 |
| A-49 | SESFVCKTCHMLRVSDAVGA | B1162-49 | pNSB1260 | A-140 | EWEDPQYAGWELFSISDLVH | B1162-140 | pNSB1256 |
| A-50 | MHVSLVFPWRLTGHIQQYKV | B1162-50 | pNSB1261 | A-141 | PMVRTEWPLCAIIPLSMLYQ | B1162-141 | pNSB1290 |
| A-51 | GRCNLQGMSFMGVGRSVWFE | B1162-51 | pNSB1237 | A-143 | RAGWHERVRQWWAIECTLEV | B1162-143 | pNSB1291 |
| A-53 | VVGGSLRDEWKWWREGRSLP | B1162-53 | pNSB1267 | A-145 | SVRCWYVLRCSFLVGSGSSV | B1162-145 | pNSB1292 |
| A-59 | AKDVERGAGGKIKACELCRL | B1162-59 | pNSB1268 | A-146 | RSCVLCAYGSRTFNGSYLLF | B1162-146 | pNSB1257 |

TABLE 5-continued

Aptamers isolated in screens with TAL1$_{1-130}$

| Aptamer | Peptide sequence | Yeast plasmid[a] | Expression cassette[b] | Aptamer | Peptide sequence | Yeast plasmid[a] | Expression cassette[b] |
|---|---|---|---|---|---|---|---|
| A-63 | VETFKARARQTPSCDLCPKT | B1162-63 | pNSB1238 | A-147 | GRGGCMLCDVDGSSAWLHTEGRLT | B1162-147 | pNSB1266 |
| A-64 | TELWWADFAKMHMEGGKGMC | B1162-64 | pNSB1239 | | GPITSQQCLSFQYLGNGEFIDG | | |
| A-67 | RHRCTSRAPRQWFRPHRDSP | B1162-67 | pNSB1269 | A-149 | TLETLDMGNPLYTCVLMDWM | B1162-149 | pNSB1324 |
| A-69 | RYRVSAGPLCSLCSLWGSVG | B1162-69 | pNSB1240 | A-150 | LVMGWRSEVSSLQGKTGTGGGPTL | B1162-150 | pNSB1293 |
| A-71 | EEGLAAITHTWLTMCFAAGL | B1162-71 | pNSB1241 | | RKCQLCRGSRYTLKYYPC | | |
| A-73 | AAFLESVRSYWSRFVRHVQG | B1162-73 | pNSB1242 | A-153 | RPGCPFCTSWRCG | B1162-153 | pNSB1294 |
| A-75 | RAMCDKDKSVCSILALYVQV | B1162-75 | pNSB1243 | A-155 | FCPECQMVAGAEDGDAIDLQ | B1162-155 | pNSB1295 |
| A-80 | CWWLREIGTFRCVTLQHVAG | B1162-80 | pNSB1244 | A-158 | RRCMLCTSDKPGGDQGALNM | B1162-158 | pNSB1296 |
| A-82 | FESAWSTLMGAMTPMVLDET | B1162-82 | pNSB1270 | A-159 | LWGGGTAWDFFVWGEDSAC | B1162-159 | pNSB1297 |
| A-83 | QALVVSPETFLCLEALGVNS | B1162-83 | pNSB1271 | A-160 | GMSGRIPEPDDWVVLFITGC | B1162-160 | pNSB1298 |
| A-84 | GGRQTEPSLTLLADLTLLLS | B1162-84 | pNSB1272 | A-161 | GGTNALLQKVFFGEVGVASM | B1162-161 | pNSB1299 |
| A-86 | GSRAELSAPEVAWLLFCTPG | B1162-86 | pNSB1245 | A-164 | ECCLFPIFAMADSFPCPSPV | B1162-164 | pNSB1300 |
| A-87 | RYSAVCRDCYEGHGRGLWYM | B1162-87 | pNSB1273 | A-165 | MLEGPLDQGLMMGTCCWECS | B1162-165 | pNSB1301 |
| A-89 | GGWLVTIVEGPLAICCLRDD | B1162-89 | pNSB1274 | A-166 | TPSVTWAEWCSCVFCRDAS | B1162-166 | pNSB1302 |
| A-90 | PSIESGWVGDQAVAPCDLSV | B1162-90 | pNSB1275 | A-167 | SWWWANNSLCREWEFAC | B1162-167 | pNSB1303 |
| A-91 | TWGAWKRDIVLVSEIGFTWG | B1162-91 | pNSB1246 | A-168 | WNMLAFGGALVASGLLRGWE | B1162-168 | pNSB1304 |
| A-94 | RLGGGRPKLWHFSPNLMAGF | B1162-94 | pNSB1247 | A-169 | DKCDDVEPFLWWGQQCFFDV | B1162-169 | pNSB1305 |
| A-97 | ERVHVCFSRKCTALSVDSSV | B1162-97 | pNSB1248 | A-170 | GSPSRISYTCLSPDVTLLFL | B1162-170 | pNSB1306 |
| A-99 | RERGGDDYRRMMHPGAASGP | B1162-99 | pNSB1249 | A-172 | MGIEACSITECTSQHCNEVA | B1162-172 | pNSB1307 |
| A-100 | RLVVGCEWRIGCSTGSGPRG | B1162-100 | pNSB1250 | A-173 | CLDNLCWELGGGFPVILIHC | B1162-173 | pNSB1308 |
| A-101 | ASLIGVGIASMHGMQTDGIY | B1162-101 | pNSB1251 | A-174 | HVHGSCPSMGWSSNSWCSVF | B1162-174 | pNSB1309 |
| A-108 | VGLMEWAVWSLEVREKLYSC | B1162-108 | pNSB1276 | A-175 | PLELEFAVCGCSWLVALDWS | B1162-175 | pNSB1310 |
| A-109 | VLGRLGGAGGCSLCDQLEAL | B1162-109 | pNSB1277 | A-176 | AWDSESLATVVASVMPWPYPT | B1162-176 | pNSB1311 |
| A-110 | IWINPNGLWWTKVGLNPYAV | B1162-110 | pNSB1252 | A-177 | TGCHYKGARCCRLTWDVLIL | B1162-177 | pNSB1312 |
| A-112 | RHESALHKSCELCYCPWKVC | B1162-112 | pNSB1278 | | | | |

[a]The yeast plasmids were cloned into pJM-1 with carbenicillin selection.
[b]The plant expression cassettes were cloned into pNSB1226 with kanamycin selection.

Because these TrxA-peptides were selected for binding to a truncated TAL1 protein that does not oligomerize, interaction with full-length TAL1 was investigated. FIG. 3B shows that yeast co-transformed with each of the 88 TrxA-peptides in the presence of either TAL1$_{1-130}$ or TAL1$_{1-352}$ baits grew on in Gal-HWUL medium. Cotransfection with the negative control bait GUS did not induce the Leu reporter and no growth occurred (FIG. 3B). No growth was seen on plates lacking leucine but supplemented with glucose (FIG. 3C). Growth on Glu-HWU medium confirmed the presence of the prey and bait plasmids in all of the transfections (FIG. 3D). Based on these results, it can be concluded that the 88 TrxA-peptides initially selected for interaction with TAL1$_{1-130}$ also bind to TAL1$_{1-352}$.

Example 4

Aptamer Interference with Viral DNA Replication

After the initial screening, a subsequent aptamer library screen was performed to identify aptamer sequences that specifically bind to the N-terminal domain of Rep and impact Rep function during viral replication.
A. Binding of TrxA-Peptides to TGMV AL1 and Interference with Viral DNA Replication.

The 11 FL-TrxA-peptides (Table 4) selected in the screen using the TAL1$_{1-352}$ bait were subcloned into a plant expression cassette containing the CaMV35S promoter with a duplicated enhancer and the rbcS E9 terminator. The constructs were co-transfected into tobacco protoplasts in the presence of a replicon plasmid containing a partial tandem copy of TGMV A that supports the release of unit length viral DNA (FIG. 4A). The TGMV A DNA, which encodes TAL1 and its replication accessory factor AL3 (FIG. 4A), replicates autonomously and accumulates to high copy number in plant cells (Orozco and Hanley-Bowdoin. (1996) J. Virol. 270:148-158). To determine whether expression of the FL-TrxA-peptides quantitatively impacts TGMV A DNA accumulation as an indicator of altered TAL1 activity, total DNA was isolated 48 h post transfection, and the levels of double-stranded TGMV A DNA were examined by DNA gel blot hybridization. Nine of the FL-TrxA-peptides had no detectable effect on viral DNA accumulation (data not shown). In contrast, cells containing the FL-42 (FIG. 4B, lane 3) and FL-60 (lane 4) cassettes only accumulated about 25% of the levels detected in a transfection containing an empty expression cassette (lane 2). The level of viral DNA detected in the presence of FL-42 and FL-60 was similar to that seen for FQ118 (FIG. 4B, lane 1), a strong trans-dominant negative mutant of TAL1 (Orozco et al. (2000) J. Biol. Chem. 275: 6114-6122). These results indicated that two of the FL-TrxA-peptides interfere with the ability of TAL1 to support viral DNA replication.

The 88 N-TrxA-peptides were also tested in replication interference assays. For these experiments, a semi-quantitative PCR protocol was developed to facilitate the analysis of a large number of expression cassettes. The assay was based on primers that distinguish the input replicon cassette and nascent viral DNA by size and DpnI sensitivity. Primers LLp1 and LLp2 (Table 3 and FIG. 4A) amplify a 4.9 Kb DNA from the replicon cassette and a 1.2 Kb product from the released TGMV A component (FIG. 4C, lane 1) in DNA extracts from E. coli cells carrying the replicon cassette plasmid. Even though the replicon cassette is the prevalent form in E. coli (data not shown), it amplified less, efficiently than the released TGMV component because of its large size. The production of both products is sensitive to DpnI digestion (FIG. 4C, lane 2) and resistant to MboI digestion (lane 3), indicative of an E. coli Dam-methylated template. Interestingly, the same results (FIG. 4C, lanes 4-6) were obtained for the mutant TGMV A replicon cassette with a frame shift mutation at TAL1 amino acid position 120 (Elmer et al. (1988) Nucleic Acids Res. 16:7043-7060).

The amplification strategy was also tested with DNA extracted from tobacco cells co-transfected with various TGMV A replicon and expression cassettes. It was then determined whether the input and nascent viral DNA can be distinguished by comparing DNA samples isolated from cells transfected with the wild type TGMV A replicon cassette or the mutant AL1 cassette. The 1.2 Kb product (top band) was produced when uncut and MboI-digested DNA from cells transfected with both cassettes was amplified (FIG. 4D, lanes 1-3 and 10-12, top and bottom). In contrast, the 1.2 Kb product was only amplified from DpnI-treated DNA from cells with the wild type cassette (FIG. 4D, lanes 1-3, middle) but not the mutant cassette (lanes 10-12, middle). This result demonstrated that residual Dam-methylated E. coli DNA can be quantitatively removed by DpnI digestion, thereby allowing the detection of nascent DNA by PCR. Subsequent verification that replication interference can be monitored by PCR was obtained by showing that the level of the 1.2 Kb PCR product is reduced in cells carrying a TAL1 dominant negative mutant (FQ118) expression cassette (FIG. 4D, lanes 7-9) relative to cells with the empty (lanes 1-3) or TrxA-GST (lanes 7-9) cassettes. This difference was not apparent in uncut or MboI-treated DNA because of the presence of intact E. coli input DNA (FIG. 4D, lanes 1-9, upper and lower). Similar results were seen for the three biological replicas for each transfection condition. Together; these results establish that the PCR assay can be used to monitor viral DNA accumulation in a reproducible, semi-quantitative manner.

Expression cassettes corresponding to the 88 N-TrxA-peptides (Table 5) were transfected into tobacco protoplasts with the wild type TGMV A replicon cassette. Total DNA was isolated 36 h after transfection and analyzed in replication interference assays using the semi-quantitative PCR method. Because of the high number of samples, the N-TrxA-peptides were initially analyzed in triplicate in 3 separate experiments. 35 N-TrxA-peptide cassettes that reduced viral DNA accumulation relative to the empty expression cassette were selected. The selected cassettes were then assayed in a single transfection experiment (FIG. 5), with 31 of 35 showing statistically significant interference activity (p<0.05 in a one-tailed Students T-test). The experiment also included the FQ118 and TrxA-GST expression cassettes as positive and negative controls, respectively. The N-TrxA-peptides were classified as weak (50-65%), moderate (25-50%) and strong (<25%) interferers (FIG. 5, dotted lines) relative to the control transfection with an empty cassette (100%). Ten N-TrxA-peptides showed strong interference (black bars), fourteen exhibited moderate interference (grey bars), and seven were weak interferers (white bars). In total, fourteen aptamers displayed interference activity that was greater or equal to FQ118. TrxA-GST did not impact viral DNA accumulation, indicating the TrxA sequences per se do not contribute to interference.
B. Binding of N-TrxA-Peptides to CaAL1 and Interference with Viral DNA Replication.

Figure 5:
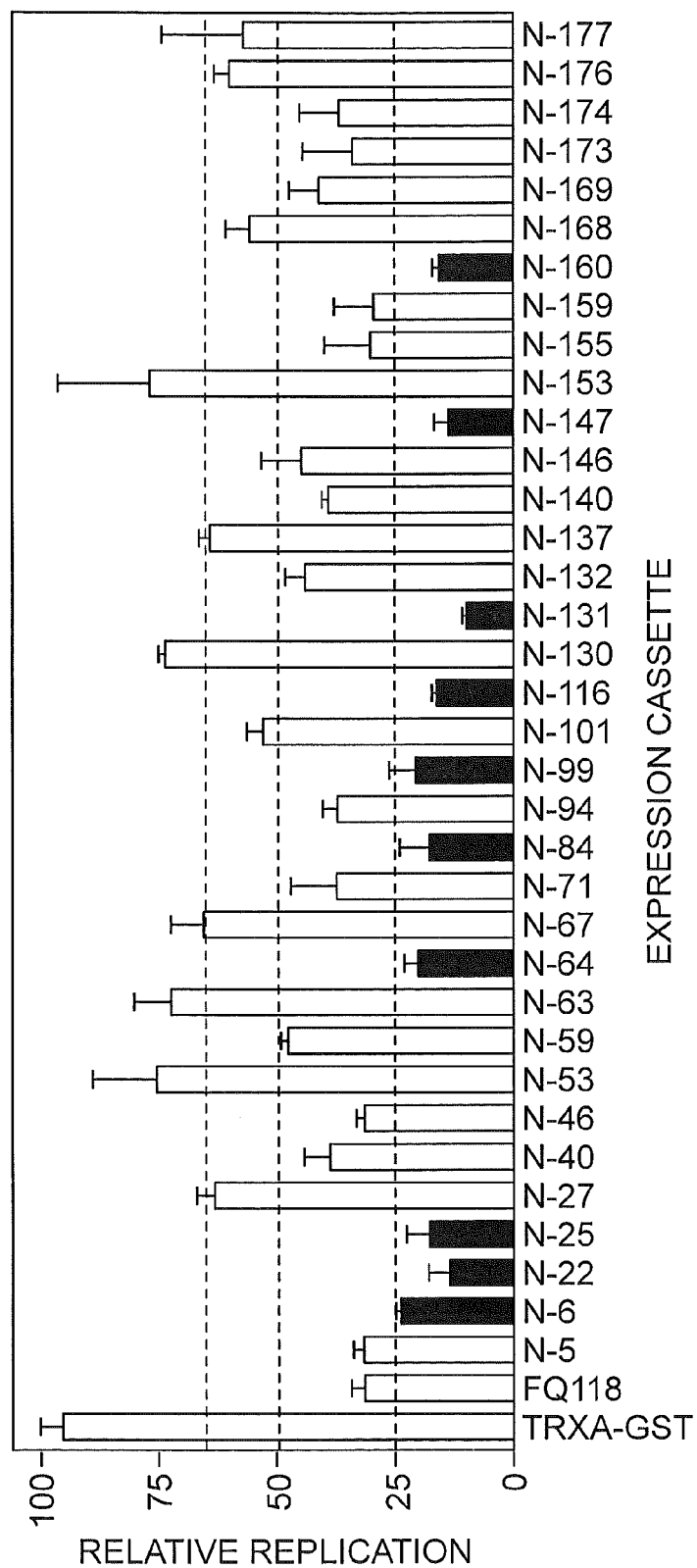
FIG. 5 shows results of studies designed to study interference with TGMV replication for aptamers that bind to $TAL1_{1-130}$. The N-TrxA-peptides selected by screening with $TAL1_{1-130}$ and cloned into plant expression cassettes (Table 4) were tested in replication interference assays using the semi-quantitative PCR assay shown in FIG. 4D. Bands corresponding to the replicated TGMV A DNA (1.2 Kb) and the PCR internal control (700 bp) were quantified using imageJ software (Abramoff, M. D., P. J. Magelhaes, and S. J. Ram. 2004. Image processing with ImageJ. Biophotonics International 11:36-42; Rasband, W. S. 1997-2005. ImageJ. National Institutes of Health). Replication in the presence of the expression cassettes indicated on the left was normalized to amount of replicated DNA in the presence of the empty expression (set to 100). Cut off values of ≥25%, ≥50% and ≥65% indicate strong (black bars), moderate (gray bars), and weak interference (white bars), respectively. Some N-TrxA-peptides show no significant interference (also in white bars). Each assay was performed in triplicate with the error bars corresponding to 2 standard errors.
Figure 6:
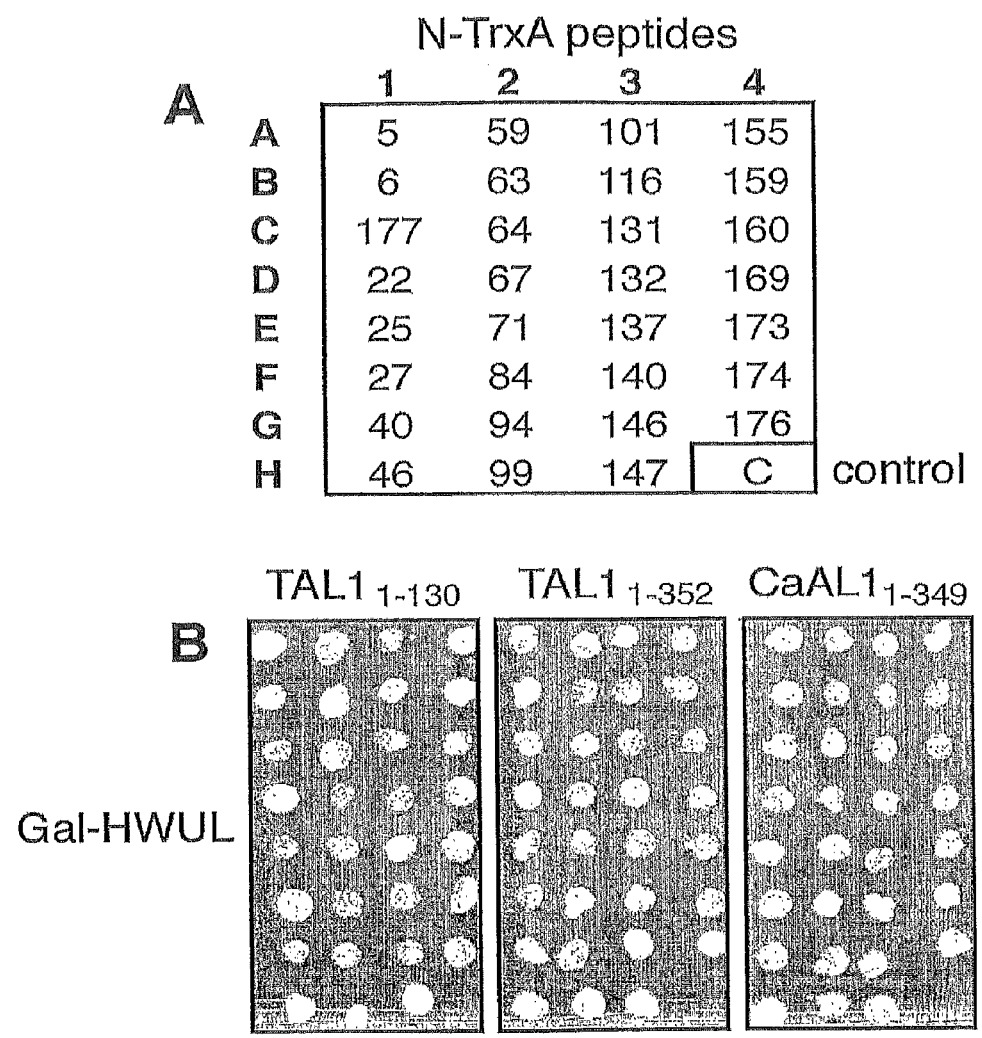
FIG. 6 shows results of studies designed to study interaction with replication proteins from a heterologous geminivirus. Selected N-TrxA-peptides were tested for interaction with CaLCuV AL1.
Figure 7:
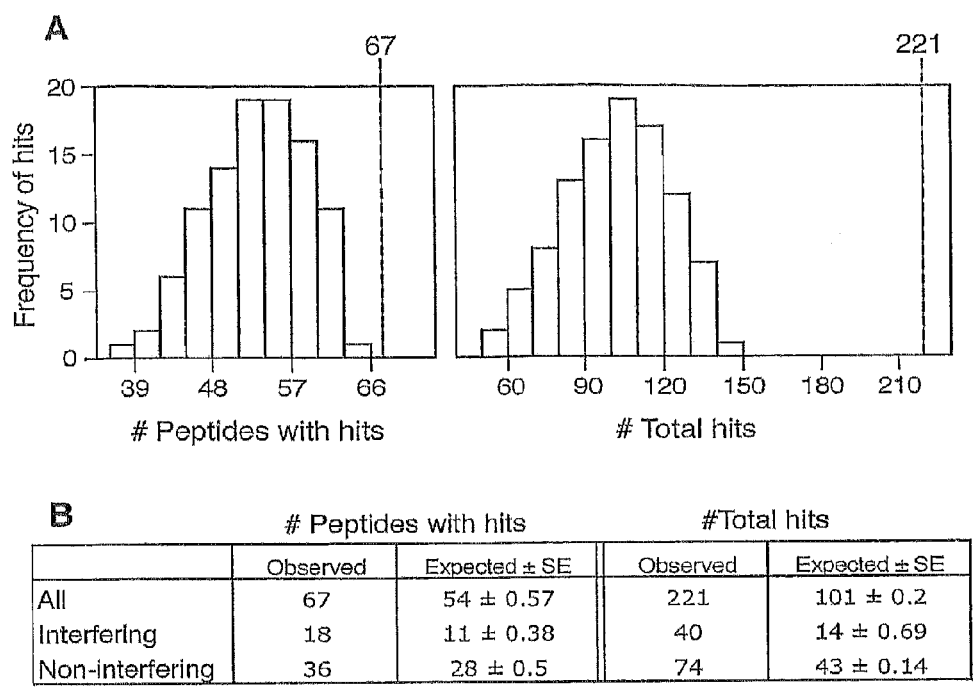
FIG. 7 presents results showing the statistical significance of pairwise alignments. Pairwise alignments were performed for 100 sets of three random databases of computer-generated 20-mers containing 88, 31 or 57 members. The frequencies of hits were compared to equivalent alignments of the databases corresponding to All, Interfering or Non-interfering N-TrxA peptides, respectively. (A) The left panel shows the frequency distribution (expected mean=54) of a random 20-mer of having at least one hit against a database comprised of 88 random 20-mers. The right panel shows the frequency distribution (expected mean=101) of the total number of hits per peptide for all the 88 random 20-mers. The dashed lines represent the observed values for the All N-TrxA-peptides database for each analysis. Similar analyses were performed for the Interfering and Non-interfering TrxA peptide databases and their random 20-mer control databases (not shown).

Motifs I, II and III in TAL1$_{1-130}$ (FIG. 1) are conserved in all geminivirus replication proteins (Ilyina and Koonin (1992) Nucleic Acids Res. 20:3279-3285; Koonin and Ilyina (1992) J. Gen. Virol. 73:2763-2766). Hence, it was determined whether peptides that bind to TAL1$_{1-130}$ and inhibit TGMV replication are also able to interact with an AU protein from a heterologous geminivirus. Accordingly, experiments were conducted using CaLCuV AL1 protein because it only shares 42% identity and 58% similarity with TAL1 across the first 130 amino acids. Full-length CaAL1 fused to the LexA DBD (CaAL1$_{1-349}$) was used as bait in yeast two-hybrid assays with the 31 N-TrxA-peptides that displayed replication interference activity (FIG. 5). All of the peptides were positive for interaction with CaAL1$_{1-349}$ in growth assays (FIG. 6B, right). The prey control did not interact with any of the baits (FIG. 6). Comparison of the interactions with TAL1$_{1-130}$, TAL1$_{1-352}$ and CaAL1$_{1-349}$ baits on LacZ plates suggested that interaction is stronger with TAL1$_{1-130}$ than with the two full-length AU baits (data not shown).

Example 5

Pairwise Alignments of Peptide Aptamers

To determine whether the peptide aptamers of the present invention are random or related in view of their selection for binding to TAL1 the 20-mers were grouped into three database corresponding to the 88 selected for binding to TAL1$_{1-130}$ (All), the 31 positive for replication interference (Interfering), and the 57 negative for interference (Non-interfering), and their sequences were compared in pairwise alignments using BLASTP. The score values of the alignments were low (data not shown) because of the short length of the peptide sequences (20 amino acids). To address the possibility that the alignments were produced by chance, 100 sets of three random databases of the same size and amino acid content as the N-TrxA-peptide were compared using BLASTP. The distribution of the frequency of hits was analyzed for each database and used to determine the expected mean and standard error of the mean for random sequences.

The frequency distribution of the 100 databases comprising the 88 random 20-mers is shown in FIG. 7A. The left panel represents the expected distribution of peptides with at least one hit while the right panel shows the frequency distribution of the total number of hits for all the 20-mers in the database. The expected means of the two distributions (54 and 101) are lower than the observed means (67 and 221, respectively) for the All database (FIG. 7B). The observed means for the Interfering and Non-interfering databases are also higher than the expected means calculated using the corresponding random databases (FIG. 7B). The observed and expected means of all three databases differed by at least two standard deviations and gave p<0.0001 in one-way Students T-tests. These results established that even though N-TrxA-peptides were derived from a random library, their sequences are not random.

Figure 8:
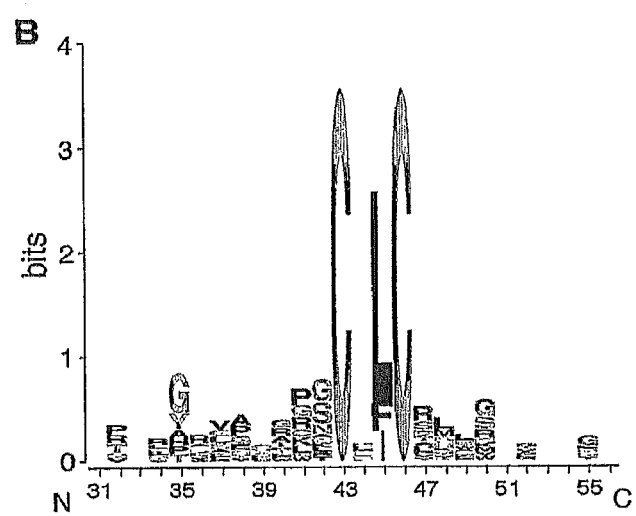
FIG. 8 presents motifs involved in AL1 binding and replication interference.

Inspection of the BLASTP alignments revealed that some pairs contained common sequences. Similar pairs were grouped and compared using the Vector NTI AlignX module. A total of 18 groups containing four or more sequences were identified among the 88 N-TrxA peptides. The putative motifs were filtered using four criteria—[1] include at least five members, [2] members interact with CaAL1, [3] contain amino acids typically involved in protein-protein interactions (Bogan and Thorn (1998) J. Mol. Biol. 280:1-9; Glaser et al. (2001) Proteins 43:89-102), and [4] related to a plant protein. Seven motifs that satisfied at least three criteria are shown in FIG. 8A. The sequence alignments are shown in FIGS. 9 and 10. Motifs 1, 4, 20, 25 and 27 consist primarily of interfering peptides, while Motif 28 is composed of mostly non-interfering peptides. Motif 24 includes 18 members that are distributed between interfering and non-interfering peptides, all of which contain a core CxLC sequence (FIG. 8). The interfering members also include conserved polar and nonpolar residues flanking the core sequence (FIG. 9). These residues occur individually in non-interfering peptides, but only the interfering peptides contain both sets of flanking residues.

Example 6

Characterization of Additional Peptide Aptamers

To expand the repertoire of aptamers, additional peptides selected in the dihybrid screen using full-length TGMV Rep were characterized. The locations of their binding sites were mapped using a series of baits corresponding to known Rep functional domains (FIG. 1). The baits contained Rep$_{1-130}$ (DNA binding, cleavage and ligation), Rep$_{101-180}$ (C3 and pRBR binding), Rep$_{130-180}$ (GRIK, CRIMP, PCNA and Ubc9 binding and oligomerization), and Rep$_{180-352}$ (helicase) and were designated as FL, NT, PI, OL and CT, respectively. Aptamers were further tested for binding to full-length CaLCuV Rep.

The results of the yeast two-hybrid experiments are summarized in Table 6. The peptide sequences and binding properties of 99 Trx-aptamers that bound to full-length TGMV Rep and do not contain a frameshift or stop condon in their coding sequence are shown in Table 7. A comprehensive listing of peptide sequences according to some embodiments of the present invention is provided in Table 8.

TABLE 6

Results summary

| TGMV baits | TGMV Rep | CaLCuV Rep |
|---|---|---|
| FL | 22 | 22 |
| FL, NT | 7 | 6 |
| FL, PI | 8 | 4 |
| FL, OL | 12 | 10 |
| FL, CT | 7 | 7 |
| FL, NT, PI | 7 | 7 |
| FL, NT, OL | 3 | 3 |
| FL, NT, CT | 5 | 4 |
| FL, PI, OL | 5 | 4 |
| FL, OL, CT | 11 | 10 |
| FL, NT, PI, OL | 1 | 1 |
| FL, NT, PI, CT | 2 | 1 |
| FL, NT, OL, CT | 5 | 4 |
| FL, NT, PI, OL, CT | 3 | 3 |

TABLE 7

Binding properties and sequences of individual peptide aptamers

| Aptamer name (FL#) | TGMV Rep bait* | CaLCuV Rep bait* | peptide sequence |
|---|---|---|---|
| 5 | FL | YES | ELLVAHLITPWTSMGRTQAL |
| 73 | FL | YES | HKDRGYANLMLCSLLACFEP |

TABLE 7-continued

Binding properties and sequences of individual peptide aptamers

| Aptamer name (FL#) | TGMV Rep bait* | CaLCuV Rep bait* | peptide sequence |
|---|---|---|---|
| 76 | FL | YES | GMLWTWLCDSPQSFVAPRGV |
| 111 | FL | YES | PVCRVGRGLLVQAKLVRAQS |
| 119 | FL | YES | DLEWDGNAYSGCCHCAFSIR |
| 141 | FL | YES | PNCEICYVARRLVLSMEACS |
| 165 | FL | YES | EGLPIDLLTNWHLTCWIALG |
| 177 | FL | YES | GVNLLQRCWGGPVHIFSYLM |
| 184 | FL | YES | CLMHMRFPLGGTWRMNLRAE |
| 190 | FL | YES | LVTALIMSESIVRMNPMYLT |
| 193 | FL | YES | EVERSRMLFNYGGMVASRVA |
| 194 | FL | YES | PWLSVDVTALIVDFLQDFSA |
| 200 | FL | YES | EGGEDSAWDWGSSGGIWCWF |
| 206 | FL | YES | CDVMEWRMMGLGLSKWLRGR |
| 219 | FL | YES | VYYHKECALDSYVRTCWVSG |
| 225 | FL | YES | PSAYEAVETLDMSEVKGLGQ |
| 237 | FL | YES | CEDMREAKVCRTLLAHSFLP |
| 251 | FL | YES | TSWRHRMPTGTDRCCFLVQL |
| 275 | FL | YES | TIDQRMVSLGAIWWSYPRCW |
| 293 | FL | YES | AQRSCWERLWTGQWRRSASD |
| 322 | FL | YES | WGYFGSFVGGVFDVWFSGVA |
| 326 | FL | YES | RNGRNICVLSVCSRFSHFNP |
| 133 | FL, NT | YES | FGVIVTNAASEFTTRVDDSC |
| 199 | FL, NT | YES | FNARALACKCDRGILILSQP |
| 214 | FL, NT | YES | IYDYTWAEEQGYVWRPAGGA |
| 227 | FL, NT | YES | LARCLCEIVGSCISYSNLPI |
| 239 | FL, NT | YES | RPWSSDTSVWWDGLFGMNYS |
| 252 | FL, NT | NO | RPWSSDTSVWWDGLFGMNYS |
| 281 | FL, NT | YES | TEACQVVLLGKRSLLPVVAG |
| 52 | FL, PI | YES | LARQPGKFIELPVLIRFATSGP LLQSNSSSGHWLSDEHWTRR |
| 180 | FL, PI | YES | VDSIDKGEALVSLWGWHVQI |
| 189 | FL, PI | YES | LVRWSYTCSVLVGLRDSLDS |
| 278 | FL, PI | NO | PPWTKRPLTSGGVRGELWVW |
| 280 | FL, PI | NO | RVDSLGIKLDKSTLVTVHVV |
| 294 | FL, PI | NO | VSWSAAGRGYVFMYRWSPRC |
| 325 | FL, PI | NO | SRSDLWVSWCRNLLDGQSWS |
| 381 | FL, PI | YES | MLGIWRVLHEMVVPLKLGVD |
| 58 | FL, OL | NO | GKLTDTTRISVCCICVSVLD |
| 72 | FL, OL | YES | MDRREDLRSLLVLTLSDARG |
| 100 | FL, OL | YES | PLLLLAADSVELQRVLARR |
| 107 | FL, OL | YES | AMTYRAAWSPPPWGVLGIWH |
| 154 | FL, OL | YES | RLTVLEAAVVLWGWSLFQVP |
| 197 | FL, OL | YES | VIVDFLSTGVSTGEVRGGIV |
| 221 | FL, OL | YES | TLHTNRFCFRWVPALDSVTT |
| 256 | FL, OL | NO | LVTALIMSESIVRMNPMYLT |
| 258 | FL, OL | YES | GVNNGGTNDPEGVSEASWIP |
| 300 | FL, OL | YES | FGVIVTNAASEFTTRGYDSC |
| 304 | FL, OL | YES | SRSDLWVSWCRNLLDGQSWS |
| 382 | FL, OL | YES | CPDCPLSSVLRTATTAFFGG |
| 121 | FL, CT | YES | QSVRKMPMFWPLAGEVWCRPLGFR |
| 181 | FL, CT | YES | PPWTKRPLTSGGVRGELWVW |
| 196 | FL, CT | YES | ISSYLWWSEYCRPGSAMGDV |
| 218 | FL, CT | YES | RVWTFFVREAALELPSRDTL |
| 222 | FL, CT | YES | LNPWEGEWTRWDVFRVLGEF |
| 265 | FL, CT | YES | GIVSKQGADEGMLEIFASSW |
| 292 | FL, CT | YES | AQRSCWERLWTGQWRRLPLM |
| 8 | FL, NT, PI | YES | DEQESVCRSCKCRYVDNWLE |
| 25 | FL, NT, PI | YES | HKDRGYANLMLCSLLACFEP |
| 117 | FL, NT, PI | YES | SFVVQSFLGGKSIFNGPFAD |
| 120 | FL, NT, PI | YES | LGAPLLRCMVHHAMMVGEGY |
| 135 | FL, NT, PI | YES | RPWSSDTSVWWDGLFGMNYS |
| 232 | FL, NT, PI | YES | SFATANSEQVLRDMLLLASH |
| 364 | FL, NT, PI | YES | TGSGLTPCLHCRVQFQRSYL |
| 216 | FL, NT, OL | YES | QMNAAPPARSCADTWSLLLF |
| 229 | FL, NT, OL | YES | SGYPKMVWGEGPMLLDWKFV |
| 246 | FL, NT, OL | YES | WCSMCSVLRAFNCPYFCPWL |
| 14 | FL, NT, CT | YES | VGGMPPLPWYEPVGLVWSCM |

TABLE 7-continued

Binding properties and sequences of individual peptide aptamers

| Aptamer name (FL#) | TGMV Rep bait* | CaLCuV Rep bait* | peptide sequence |
|---|---|---|---|
| 21 | FL, NT, CT | YES | GKLTDTRISVCCCICVSVLD |
| 167 | FL, NT, CT | YES | SFMMRLLRTGEMQFQADCVGGP IPLKSPRALSLYNWGLLLWV |
| 202 | FL, NT, CT | YES | LLYPSLTLTLWRWLFADEGC |
| 247 | FL, NT, CT | NO | PWIFDRSVVCEEREAPRRHL |
| 6 | FL, PI, OL | YES | TNELPLTIVTDDVSQLVISRGP ARHLYELMPEMLVLRSARLT |
| 334 | FL, PI, OL | YES | GVLFTFKKYPQGLSCTTSYG |
| 341 | FL, PI, OL | NO | LLACSVYWLWQRPCDGCLFM |
| 365 | FL, PI, OL | YES | TRMHSLCSGFCVICMGGPRV |
| 380 | FL, PI, OL | YES | RNGRNICVLSVCSRFSHFNP |
| 109 | FL, OL, CT | YES | GMLWTWLCDSPQSFVAPRGV |
| 116 | FL, OL, CT | YES | EVVETAEVYWSCGDWSCEGW |
| 179 | FL, OL, CT | YES | CAMCLDVFGWSASHWGGFTV |
| 220 | FL, OL, CT | YES | FNARALACKCDRRILILSQP |
| 245 | FL, OL, CT | YES | GRFGQGQCYQVADSTYWTFGPG GPRKCEREPAGWSDTGWVC |
| 254 | FL, OL, CT | YES | RPWSSDTSVWWDGLFGMNYS |
| 262 | FL, OL, CT | YES | LLACSVYWLWQRPCDGCLFM |
| 302 | FL, OL, CT | NO | SFSSLFLAWLMQTGQEAGTV |
| 312 | FL, OL, CT | YES | HPYLITDIISMYRSPWSVPA |
| 352 | FL, OL, CT | YES | VVQNVRGWLVYCCADFHTYV |
| 355 | FL, OL, CT | YES. | LRGVSPWLQSFVSIAVQSCK |
| 313 | FL, NT, PI, OL | YES | RDALTNIGRSICALLLVLCK |
| 153 | FL, NT, PI, CT | YES | PNCEICYVARRLVLSMEACS |
| 223 | FL, NT, PI, CT | NO | QMFWFTDSEGKPGFCTFYGF |
| 110 | FL, NT, OL, CT | YES | ALKDEPFCDLPMVLVSWWRG |
| 208 | FL, NT, OL, CT | YES | DLEWDGNAYSGCCHCAGSIR |
| 257 | FL, NT, OL, CT | YES | LLACSVYWLWQRPCDGCLFM |
| 328 | FL, NT, OL, CT | NO | GGSDERYFWYQSFSSCAYEW |
| 434 | FL, NT, OL, CT | YES | RGRMEADKSFDSTCLRCGCS |
| 236 | FL, NT, PI, OL, CT | YES | VGPLIVGPPGMEMTANSWSC |
| 242 | FL, NT, PI, OL, CT | YES | DLRLPVYSEWVRVYSSDAWM |
| 293 | FL, NT, PI, OL, CT | YES | AQRSCWERLWTGQWRRLPLM |

*TGMV baits
FL — full length (aa 1-352)
NT — N-terminus (aa 1-130)
PI — protein interaction (aa 101-180)
OL — oligomerization (aa 130-180)
CT — C-terminus (181-352)
CaLCuV bait
full length (aa 1-347)

TABLE 8

Listing of peptide sequences

| SEQ ID NO. | Research Name | Peptide sequence |
|---|---|---|
| 1 | Motif 3 | VRDYILKEPL |
| 2 | Motif 3 | VKSYVDKDGD |
| 3 | Motif 3 | VKEYIDKDGV |
| 4 | Motif 3 | VNSYVDKDGD |
| 5 | Motif 3 | NKEYCSKEGH |
| 6 | Motif 3 | NLTYVSKIGG |
| 7 | Motif 3 | AQLYAMKEDS |
| 8 | Motif 3 | ARSYCMKEDT |

TABLE 8-continued

Listing of peptide sequences

| SEQ ID NO. | Research Name | Peptide sequence |
|---|---|---|
| 9 | Motif 1 | WxDxxxAW |
| 10 | Motif 4 | MHxxxxxG |
| 11 | Motif 20 | (L/M)GGxxP |
| 12 | Motif 24 | (G/S)CxLCxL |
| 13 | Motif 25 | WxxxSLC |
| 14 | Motif 27 | (S/A)FxxAxVAS |
| 15 | Motif 28 | WfxVL |
| 16 | A-3 | GFRAPGLSPTRPSCLICSTL |
| 17 | A-5 | NECLICHMLGIREFGLSA |
| 18 | A-6 | GTLWRRCASSWAFPPDCPSA |
| 19 | A-8 | RRALRHCTGCMLSQRLGTAL |
| 20 | A-9 | HSMHSCSVGRCLVDVKVVVS |
| 21 | A-12 | WMVCAGCGALRTRQVTLHPG |
| 22 | A-15 | GGFVPMRLCTCLLIVRLFI |
| 23 | A-16 | VPQPLNCDLCVLMGGASSSR |
| 24 | A-18 | RRDYRKFFALNCQLCRLTVT |
| 25 | A-22 | CRTRGCGCHLCRMLSQFTGG |
| 26 | A-25 | MRLGKGWNLMFLEEVSVLDA |
| 27 | A-27 | RDPQLGQVAQTWGCRLCLLE |
| 28 | A-30 | LVSESCGSWFCLCPWEVLNW |
| 29 | A-40 | LQYSWNLYSVASFKTRRVSS |
| 30 | A-41 | RLQESSIDLTPGIYLGMDFV |
| 31 | A-46 | CYMEVEGRPRRWADSFFVAW |
| 32 | A-49 | SESFVCKTCHMLRVSDAVGA |
| 33 | A-50 | MHVSLVFPWRLTGHIQQYKV |
| 34 | A-51 | GRCNLQGMSFMGVGRSVWFE |
| 35 | A-53 | VVGGSLRDEWKWWREGRSLP |
| 36 | A-59 | AKDVERGAGGKIKACELCRL |
| 37 | A-63 | VETFKARARQTPSCDLCPKT |
| 38 | A-64 | TELWWADFAKMHMEGGKGMC |
| 39 | A-67 | RHRCTSRAPRQWFRPHRDSP |
| 40 | A-69 | RYRVSAGPLCSLCSLWGSVG |
| 41 | A-71 | EEGLAAITHTWLTMCFAAGL |
| 42 | A-73 | AAFLESVRSYWSRFVRHVQG |
| 43 | A-75 | RAMCDKDKSVCSILALYVQV |
| 44 | A-80 | CWWLREIGTFRCVTLQHVAG |
| 45 | A-82 | FESAWSTLMGAMTPMVLDET |
| 46 | A-83 | QALVVSPETFLCLEALGVNS |

TABLE 8-continued

Listing of peptide sequences

| SEQ ID NO. | Research Name | Peptide sequence |
|---|---|---|
| 47 | A-84 | GGRQTEPSLTLLADLTLLLS |
| 48 | A-86 | GSRAELSAPEVAWLLFCTPG |
| 49 | A-87 | RYSAVCRDCYEGHGRGLWYM |
| 50 | A-89 | GGWLVTIVEGPLAICCLRDD |
| 51 | A-90 | PSIESGWVGDQAVAPCDLSV |
| 52 | A-91 | TWGAWKRDIVLVSEIGFTWG |
| 53 | A-94 | RLGGGRPKLWHFSPNLMAGF |
| 54 | A-97 | ERVHVCFSRKCTALSVDSSV |
| 55 | A-99 | RERGGDDYRRMMHPGAASGP |
| 56 | A-100 | RLVVGCEWRIGCSTGSGPRG |
| 57 | A-101 | ASLIGVGIASMHGMQTDGIY |
| 58 | A-108 | VGLMEWAVWSLEVREKLYSC |
| 59 | A-109 | VLGRLGGAGGCSLCDQLEAL |
| 60 | A-110 | IWINPNGLWWTKVGLNPYAV |
| 61 | A-112 | RHESALHKSCELCYCPWKVC |
| 62 | A-114 | VRSHRRYQRNWEPVVSWFSS |
| 63 | A-115 | WCGPQVSARCK |
| 64 | A-116 | SCDEAFDAASVASELFCQPY |
| 65 | A-117 | ARMALSLREWEYLFFKDAPSGPGLQGLSLASRLNLVILRGYG |
| 66 | A-119 | RSYGGGEIPSVTMHCWIHCD |
| 67 | A-123 | SSSRWVPFALQDPLFSSDDW |
| 68 | A-124 | YLWSSKMDEWVAMDDVYAAC |
| 69 | A-127 | TWGLVCTGTGWGLLDTVVRA |
| 70 | A-129 | VYEWGDVLCGGSMATQWGL |
| 71 | A-130 | ASNGEIAYCVEQAMLLLCFH |
| 72 | A-131 | ELIVHEWPLILSRVGRIVL |
| 73 | A-132 | GRVQLEILVSEAEEGVSFL |
| 74 | A-135 | RDAEWQDVLGRARAVHLRGR |
| 75 | A-136 | GLKWKSDNGCVYVSFMRGGV |
| 76 | A-137 | SSSPVPYSGGTCNLCSMRMW |
| 77 | A-140 | EWEDPQYAGWELFSISDLVH |
| 78 | A-141 | PMVRTEWPLCATIPLSMLYQ |
| 79 | A-143 | RAGWHE RVRQWWAIECTLEV |
| 80 | A-145 | SVRCWYVLRCSFLVGSGSSV |
| 81 | A-146 | RSCVLCAYGSRTFNGSYLLF |
| 82 | A-147 | GRGGCMLCDVDGSSAWLHTEGRLTGPITSQQCLSFQYLGNGEFIDG |
| 83 | A-149 | TLETLDMGNPLYTCVLMDWM |
| 84 | A-150 | LVMGWRSEVSSLQGKTGTGGGPTLRKCQLCRGSRYTLKYYPC |

TABLE 8-continued

Listing of peptide sequences

| SEQ ID NO. | Research Name | Peptide sequence |
|---|---|---|
| 85 | A-153 | RPGCPFCTSWRCG |
| 86 | A-155 | FCPECQMVAGAEDGDAIDLQ |
| 87 | A-158 | RRCMLCTSDKPGGDQGALNM |
| 88 | A-159 | LWGGGTAWDFFVWGEDSAC |
| 89 | A-160 | GMSGRIPEPDDWVVLFITGC |
| 90 | A-161 | GGTNALLQKVFFGEVGVASM |
| 91 | A-164 | ECCLFPIFAMADSFPCPSPV |
| 92 | A-165 | MLEGPLDQGLMMGTCCWECS |
| 93 | A-166 | TPSVTWLAEWCSCVFCRDAS |
| 94 | A-167 | SWWWANNSLCREWEFAC |
| 95 | A-168 | WNMLAFGGALVASGLLRGWE |
| 96 | A-169 | DKCDDVEPFLWWGQQCFFDV |
| 97 | A-170 | GSPSRISYTCLSPDVTLLFL |
| 98 | A-172 | MGIEACSITECTSQHCNEVA |
| 99 | A-173 | CLDNLCWELGGGFPVILIHC |
| 100 | A-174 | HVHGSCPSMGWSSNSWCSVF |
| 101 | A-175 | PLELEFAVCGCSWLVALDWS |
| 102 | A-176 | AWDSESLATWASVMPWPYPT |
| 103 | A-177 | TGCHYKGARCCRLTWDVLIL |
| 104 | FL-1 | PLSGRQGVHLYFLLLMPA |
| 105 | FL-7 | FAVEYGSQGWGLWYCVWLDL |
| 106 | FL-18 | FQSRMGGGSGVVNAKLWAKE |
| 107 | FL-19 | VASRDSGAWRELHSFLNFAS |
| 108 | FL-41 | YYMALLYSQCPTVVLFRMTT |
| 109 | FL-42 | DFVCLCLFACTSDLSAFRVC |
| 110 | FL-57 | TAFRWDMFWMHTSGTWRKP |
| 111 | FL-60 | FASGSGEPVGLGLGSPLEKL |
| 112 | FL-70 | VYDSALCLVVGRCGLIRCR |
| 113 | FL-90 | LVWASM |
| 114 | FL-99 | LHESCWGWAGDSSPQGVLAG |
| 115 | FL-5 | ELLVAHLITPWTSMGRTQAL |
| 116 | FL-6 | TNELPLTIVTDDVSQLVISRGPARHLYELMPEMLVLRSARLT |
| 117 | FL-8 | DEQESVCRSCKCRYVDNWLE |
| 118 | FL-14 | VGGMPPLPWYEPVGLVWSCM |
| 119 | FL-21 | GKLTDTRISVCCCICVSVLD |
| 120 | FL-25 | HKDRGYANLMLCSLLACFEP |
| 121 | FL-52 | LARQPGKFIELPVLIRFATSGPLLQSNSSSGHWLSDEHWTRR |
| 122 | FL-58 | GKLTDTTRISVCCCICVSVLD |

TABLE 8-continued

Listing of peptide sequences

| SEQ ID NO. | Research Name | Peptide sequence |
|---|---|---|
| 123 | FL-72 | MDRREDLRSLLVLTLSDARG |
| 124 | FL-73 | HKDRGYANLMLCSLLACFEP |
| 125 | FL-76 | GMLWTWLCDSPQSFVAPRGV |
| 126 | FL-100 | PLLLLAADSVELQRVLARR |
| 127 | FL-107 | AMTYRAAWSPPPWGVLGIWH |
| 128 | FL-109 | GMLWTWLCDSPQSFVAPRGV |
| 129 | FL-110 | ALKDEPFCDLPMVLVSWWRG |
| 130 | FL-111 | PVCRVGRGLLVQAKLVRAQS |
| 131 | FL-116 | EVVETAEVYWSCGDWSCEGW |
| 132 | FL-117 | SFVVQSFLGGKSIFNGPFAD |
| 133 | FL-119 | DLEWDGNAYSGCCHCAFSIR |
| 134 | FL-120 | LGAPLLRCMVHHAMMVGEGY |
| 135 | FL-121 | QSVRKMPMFWPLAGEVWCRPLGFR |
| 136 | FL-133 | FGVIVTNAASEFTTRVDDSC |
| 137 | FL-135 | RPWSSDTSVWWDGLFGMNYS |
| 138 | FL-141 | PNCEICYVARRLVLSMEACS |
| 139 | FL-153 | PNCEICYVARRLVLSMEACS |
| 140 | FL-154 | RLTVLEAAVVLWGWSLFQVP |
| 141 | FL-165 | EGLPIDLLTNWHLTCWIALG |
| 142 | FL-167 | SFMMRLLRTGEMQFQADCVGGPIPLKSPRALSLYNWGLLLWV |
| 143 | FL-177 | GVNLLQRCWGGPVHIFSYLM |
| 144 | FL-179 | CAMCLDVFGWSASHWGGFTV |
| 145 | FL-180 | VDSIDKGEALVSLWGWHVQI |
| 146 | FL-181 | PPWTKRPLTSGGVRGELWVW |
| 147 | FL-184 | CLMHMRFPLGGTWRMNLRAE |
| 148 | FL-189 | LVRWSYTCSVLVGLRDSLDS |
| 149 | FL-190 | LVTALIMSESIVRMNPMYLT |
| 150 | FL-193 | EVERSRMLFNYGGMVASRVA |
| 151 | FL-194 | PWLSVDVTALIVDFLQDFSA |
| 152 | FL-196 | ISSYLWWSEYCRPGSAMGDV |
| 153 | FL-197 | VIVDFLSTGVSTGEVRGGIV |
| 154 | FL-199 | FNARALACKCDRGILILSQP |
| 155 | FL-200 | EGGEDSAWDWGSSGGIWCWF |
| 156 | FL-202 | LLYPSLTLTLWRWLFADEGC |
| 157 | FL-206 | CDVMEWRMMGLGLSKWLRGR |
| 158 | FL-208 | DLEWDGNAYSGCCHCAGSIR |
| 159 | FL-214 | IYDYTWAEEQGYVWRPAGGA |
| 160 | FL-216 | QMNAAPPARSCADTWSLLLF |

TABLE 8-continued

Listing of peptide sequences

| SEQ ID NO. | Research Name | Peptide sequence |
|---|---|---|
| 161 | FL-218 | RVWTFFVREAALELPSRDTL |
| 162 | FL-219 | VYYHKECALDSYVRTCWVSG |
| 163 | FL-220 | FNARALACKCDRRILILSQP |
| 164 | FL-221 | TLHTNRFCFRWVPALDSVTT |
| 165 | FL-222 | LNPWEGEWTRWDVFRVLGEF |
| 166 | FL-223 | QMFWFTDSEGKPGFCTFYGF |
| 167 | FL-225 | PSAYEAVETLDMSEVKGLGQ |
| 168 | FL-227 | LARCLCEIVGSCISYSNLPI |
| 169 | FL-229 | SGYPKMVWGEGPMLLDWKFV |
| 170 | FL-232 | SFATANSEQVLRDMLLLASH |
| 171 | FL-236 | VGPLIVGPPGMEMTANSWSC |
| 172 | FL-237 | CEDMREAKVCRTLLAHSFLP |
| 173 | FL-239 | RPWSSDTSVWWDGLFGMNYS |
| 174 | FL-242 | DLRLPVYSEWVRVYSSDAWM |
| 175 | FL-245 | GRFGQGQCYQVADSTYWTFGPGGPRKCEREPAGWSDTGWVC |
| 176 | FL-246 | WCSMCSVLRAFNCPYFCPWL |
| 177 | FL-247 | PWIFDRSVVCEEREAPRRHL |
| 178 | FL-251 | TSWRHRMPTGTDRCCFLVQL |
| 179 | FL-252 | RPWSSDTSVWWDGLFGMNYS |
| 180 | FL-254 | RPWSSDTSVWWDGLFGMNYS |
| 181 | FL-256 | LVTALIMSESIVRMNPMYLT |
| 182 | FL-257 | LLACSVYWLWQRPCDGCLFM |
| 183 | FL-258 | GVNNGGTNDPEGVSEASWIP |
| 184 | FL-262 | LLACSVYWLWQRPCDGCLFM |
| 185 | FL-265 | GIVSKQGADEGMLEIFASSW |
| 186 | FL-275 | TIDQRMVSLGAIWWSYPRCW |
| 187 | FL-278 | PPWTKRPLTSGGVRGELWVW |
| 188 | FL-280 | RVDSLGIKLDKSTLVTVHVV |
| 189 | FL-281 | TEACQVVLLGKRSLLPVVAG |
| 190 | FL-292 | AQRSCWERLWTGQWRRLPLM |
| 191 | FL-293 | AQRSCWERLWTGQWRRSASD |
| 192 | FL-294 | VSWSAAGRGYVFMYRWSPRC |
| 193 | FL-300 | FGVIVTNAASEFTTRGYDSC |
| 194 | FL-302 | SFSSLFLAWLMQTGQEAGTV |
| 195 | FL-304 | SRSDLWVSWCRNLLDGQSWS |
| 196 | FL-312 | HPYLITDIISMYRSPWSVPA |
| 197 | FL-313 | RDALTNIGRSICALLLVLCK |
| 198 | FL-322 | WGYFGSFVGGVFDVWFSGVA |

TABLE 8-continued

Listing of peptide sequences

| SEQ ID NO. | Research Name | Peptide sequence |
| --- | --- | --- |
| 199 | FL-325 | SRS DLWVSWCRNLLDGQSWS |
| 200 | FL-326 | RNGRNICVLSVCSRFSHFNP |
| 201 | FL-328 | GGSDERYFWYQSFSSCAYEW |
| 202 | FL-334 | GVLFTFKKYPQGLSCTTSYG |
| 203 | FL-341 | LLACSVYWLWQRPCDGCLFM |
| 204 | FL-352 | VVQNVRGWLVYCCADFHTYV |
| 205 | FL-355 | LRGVSPWLQSFVSIAVQSCK |
| 206 | FL-364 | TGSGLTPCLHCRVQFQRSYL |
| 207 | FL-365 | TRMHSLCSGFCVICMGGPRV |
| 208 | FL-380 | RNGRNICVLSVCSRFSHFNP |
| 209 | FL-381 | MLGIWRVLHEMVVPLKLGVD |
| 210 | FL-382 | CPDCPLSSVLRTATTAFFGG |
| 211 | FL-434 | RGRMEADKSFDSTCLRCGCS |

The peptide aptamers of the present invention were isolated in a stringent in vivo screen and, as such, are likely to bind to viral replication initiation proteins with high affinity, fold correctly and be stably expressed in a cellular environment. Some of the peptide aptamers were selected for binding to the N-terminus of AL1, which does not resemble plant proteins. Consequently, the peptide aptamers are unlikely to interact with host proteins, minimizing the risk that their expression will be toxic to plants. Further, the peptide aptamers are ca. 12 kD—a size typical of a small, stable protein that can move passively into the nucleus where replication proteins are localized. Additionally, several of the aptamer peptides reduced TGMV DNA accumulation more strongly than a trans-dominant negative TAL1 mutant that can confer immunity to TGMV infection when expressed in transgenic plants. Finally, the ability of the aptamer peptides to bind to the divergent TAL1 and CaAL1 proteins suggests that these peptides recognize conserved features in the N-termini of geminivirus replication proteins. This observation represents a key difference from interference strategies based on viral sequences like trans-dominant negative mutants, antisense RNAs and RNAi constructs, all of which are only effective against the cognate geminivirus or closely related viruses. In contrast, a resistance strategy based on the interfering aptamer peptides could be broadly applicable to all geminivirus genera and other eukaryotic single-stranded DNA viruses with related replication proteins and could confer resistance to mixed infections and viral variants.

The foregoing examples are illustrative of the present invention, and are not to be construed as limiting thereof. The invention is described by the following claims, with equivalents of the claims to be included therein.

That which is claimed is:

1. A polypeptide comprising an amino acid sequence selected from the group consisting of:
   (a) the amino acid sequence of SEQ ID NO:38;
   (b) a fragment of the amino acid sequence of SEQ ID NO:38, wherein the fragment comprises MHXXXXXG; and wherein the fragment binds to a viral replication (Rep) protein; and
   (c) an amino acid sequence having at least 95% sequence identity to the amino acid sequence of (a) or (b) and binds to a viral Rep protein selected from the group consisting of a geminivirus Rep protein, a nanovirus Rep protein, a circovirus Rep protein and combinations thereof;
   wherein X represents any amino acid.

2. The polypeptide according to claim 1, wherein the polypeptide binds to a Rep protein selected from the group consisting of a nanovirus Rep protein, a circovirus Rep protein and combinations thereof.

3. The polypeptide according to claim 1, wherein the polypeptide binds to a geminivirus Rep protein.

4. The polypeptide according to claim 1, wherein the polypeptide binds to a Rep protein selected from the group consisting of a tomato golden mosaic virus (TGMV) Rep protein, a cabbage leaf curl virus (CbLCV) Rep protein, a tomato yellow leaf curl virus (TYLCV) Rep protein, a tomato mottle virus (ToMoV) Rep protein, an African cassava mosaic virus (ACMV) Rep protein, a maize streak virus (MSV) Rep protein, and a cotton leaf curl virus (CLCuV) Rep protein, and combinations thereof.

5. The polypeptide according to claim 1, wherein the amino acid sequence comprises MHXXXXXG.

6. The polypeptide according to claim 1 consisting of the amino acid sequence of SEQ ID NO:38.

7. A fusion protein comprising the polypeptide according to claim 1.

8. The fusion protein according to claim 7, wherein the fusion protein comprises thioredoxin.

9. The polypeptide according to claim 1, wherein the polypeptide comprises a fragment of the amino acid sequence of SEQ ID NO:38, wherein the fragment comprises MHXXXXXG, and wherein the fragment binds to a viral Rep protein.

10. The polypeptide according to claim 1, wherein the amino acid sequence comprises no more than three amino acid substitutions, insertions and/or deletions as compared with the amino acid sequence of (a).

11. The polypeptide according to claim 1, wherein the amino acid sequence comprises no more than two amino acid substitutions as compared with the amino acid sequence of (a), and wherein all of the amino acid substitutions are conservative substitutions.

12. The polypeptide according to claim 1, wherein the polypeptide inhibits viral replication.

13. The polypeptide according to claim 12, wherein the polypeptide inhibits geminivirus, nanovirus and/or circovirus replication.

14. The polypeptide according to claim 12, wherein the polypeptide inhibits geminivirus replication.

15. The polypeptide according to claim 14, wherein the polypeptide inhibits tomato golden mosaic virus (TGMV), tomato yellow leaf curl virus (TYLCV) replication, cabbage leaf curl virus (CbLCV) replication, tomato mottle virus (ToMoV) replication, African cassava mosaic virus (ACMV) replication, maize streak virus (MSV) replication and/or cotton leaf curl virus (CLCuV) replication.

16. The polypeptide according to claim 1, wherein the polypeptide inhibits viral infection.

17. The polypeptide according to claim 16, wherein the polypeptide inhibits geminivirus, nanovirus and/or circovirus infection.

18. The polypeptide according to claim 16, wherein the polypeptide inhibits geminivirus replication.

19. The polypeptide according to claim 18, wherein the polypeptide inhibits tomato golden mosaic virus (TGMV), tomato yellow leaf curl virus (TYLCV) infection, cabbage leaf curl virus (CbLCV) infection, tomato mottle virus (ToMoV) infection, African cassava mosaic virus (ACMV) infection, maize streak virus (MSV) infection and/or cotton leaf curl virus (CLCuV) infection.

20. A method of detecting a viral infection, the method comprising:
   (a) contacting a sample with a polypeptide according to claim 1; and
   (b) detecting the presence or absence of binding between the polypeptide and a viral Rep protein, wherein the binding of the polypeptide to the viral Rep protein in the sample indicates the presence of a geminivirus, nanovirus and/or circovirus.

21. A method of detecting a viral infection, the method comprising:
   (a) contacting a sample with a fusion protein according to claim 7; and
   (b) detecting the presence or absence of binding between the polypeptide and a viral Rep protein, wherein the binding of the polypeptide to the viral Rep protein in the sample indicates the presence of a geminivirus, nanovirus and/or circovirus.

22. A method of inhibiting viral replication in a plant cell, the method comprising introducing the polypeptide of claim 1 into the plant cell in an amount effective to inhibit geminivirus, nanovirus and/or circovirus replication.

23. A method of inhibiting viral replication in a plant cell, the method comprising introducing the fusion protein of claim 7 into the plant cell in an amount effective to inhibit geminivirus, nanovirus and/or circovirus replication.

24. A method of providing increased resistance to viral infection in a plant, the method comprising introducing the polypeptide of claim 1 into the plant in an amount effective to increase resistance to geminivirus, nanovirus and/or circovirus infection.

25. A method of providing increased resistance to viral infection in a plant, the method comprising introducing the fusion protein of claim 7 into the plant in an amount effective to increase resistance to geminivirus, nanovirus and/or circovirus infection.

26. The polypeptide of claim 1, wherein the fragment of the amino acid sequence of SEQ ID NO:38 binds to a single-stranded DNA (ssDNA) viral replication (Rep) protein.

* * * * *

SEQUENCE LISTING

```
<160> NUMBER OF SEQ ID NOS: 232

<210> SEQ ID NO 1
<211> LENGTH: 10
<212> TYPE: PRT
<213> ORGANISM: Artificial
<220> FEATURE:
<223> OTHER INFORMATION: Rep structural motif

<400> SEQUENCE: 1

Val Arg Asp Tyr Ile Leu Lys Glu Pro Leu
1               5                   10

<210> SEQ ID NO 2
<211> LENGTH: 10
<212> TYPE: PRT
<213> ORGANISM: Artificial
<220> FEATURE:
<223> OTHER INFORMATION: Rep structural motif
```

```
<400> SEQUENCE: 2

Val Lys Ser Tyr Val Asp Lys Asp Gly Asp
1               5                   10

<210> SEQ ID NO 3
<211> LENGTH: 10
<212> TYPE: PRT
<213> ORGANISM: Artificial
<220> FEATURE:
<223> OTHER INFORMATION: Rep structural motif

<400> SEQUENCE: 3

Val Lys Glu Tyr Ile Asp Lys Asp Gly Val
1               5                   10

<210> SEQ ID NO 4
<211> LENGTH: 10
<212> TYPE: PRT
<213> ORGANISM: Artificial
<220> FEATURE:
<223> OTHER INFORMATION: Rep structural motif

<400> SEQUENCE: 4

Val Asn Ser Tyr Val Asp Lys Asp Gly Asp
1               5                   10

<210> SEQ ID NO 5
<211> LENGTH: 10
<212> TYPE: PRT
<213> ORGANISM: Artificial
<220> FEATURE:
<223> OTHER INFORMATION: Rep structural motif

<400> SEQUENCE: 5

Asn Lys Glu Tyr Cys Ser Lys Glu Gly His
1               5                   10

<210> SEQ ID NO 6
<211> LENGTH: 10
<212> TYPE: PRT
<213> ORGANISM: Artificial
<220> FEATURE:
<223> OTHER INFORMATION: Rep structural motif

<400> SEQUENCE: 6

Asn Leu Thr Tyr Val Ser Lys Ile Gly Gly
1               5                   10

<210> SEQ ID NO 7
<211> LENGTH: 10
<212> TYPE: PRT
<213> ORGANISM: Artificial
<220> FEATURE:
<223> OTHER INFORMATION: Rep structural motif

<400> SEQUENCE: 7

Ala Gln Leu Tyr Ala Met Lys Glu Asp Ser
1               5                   10

<210> SEQ ID NO 8
<211> LENGTH: 10
<212> TYPE: PRT
<213> ORGANISM: Artificial
<220> FEATURE:
<223> OTHER INFORMATION: Rep structural motif

<400> SEQUENCE: 8
```

```
Ala Arg Ser Tyr Cys Met Lys Glu Asp Thr
1               5                   10

<210> SEQ ID NO 9
<211> LENGTH: 8
<212> TYPE: PRT
<213> ORGANISM: Artificial
<220> FEATURE:
<223> OTHER INFORMATION: Rep structural motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid

<400> SEQUENCE: 9

Trp Xaa Asp Xaa Xaa Xaa Ala Trp
1               5

<210> SEQ ID NO 10
<211> LENGTH: 8
<212> TYPE: PRT
<213> ORGANISM: Artificial
<220> FEATURE:
<223> OTHER INFORMATION: Rep structural motif
<220> FEATURE:
<221> NAME/KEY: misc_feature
<222> LOCATION: (3)..(7)
<223> OTHER INFORMATION: Xaa can be any naturally occurring amino acid

<400> SEQUENCE: 10

Met His Xaa Xaa Xaa Xaa Xaa Gly
1               5

<210> SEQ ID NO 11
<211> LENGTH: 6
<212> TYPE: PRT
<213> ORGANISM: Artificial
<220> FEATURE:
<223> OTHER INFORMATION: Rep structural motif
<220> FEATURE:
<221> NAME/KEY: misc_feature
<222> LOCATION: (1)..(1)
<223> OTHER INFORMATION: Xaa may be Leu or Met
<220> FEATURE:
<221> NAME/KEY: misc_feature
<222> LOCATION: (4)..(5)
<223> OTHER INFORMATION: Xaa can be any naturally occurring amino acid

<400> SEQUENCE: 11

Xaa Gly Gly Xaa Xaa Pro
1               5

<210> SEQ ID NO 12
<211> LENGTH: 7
<212> TYPE: PRT
<213> ORGANISM: Artificial
<220> FEATURE:
<223> OTHER INFORMATION: Rep structural motif
<220> FEATURE:
<221> NAME/KEY: misc_feature
<222> LOCATION: (1)..(1)
<223> OTHER INFORMATION: Xaa may be Gly or Ser
<220> FEATURE:
<221> NAME/KEY: misc_feature
<222> LOCATION: (3)..(3)
<223> OTHER INFORMATION: Xaa can be any naturally occurring amino acid
<220> FEATURE:
```

```
<221> NAME/KEY: misc_feature
<222> LOCATION: (6)..(6)
<223> OTHER INFORMATION: Xaa can be any naturally occurring amino acid

<400> SEQUENCE: 12

Xaa Cys Xaa Leu Cys Xaa Leu
1               5

<210> SEQ ID NO 13
<211> LENGTH: 7
<212> TYPE: PRT
<213> ORGANISM: Artificial
<220> FEATURE:
<223> OTHER INFORMATION: Rep structural motif
<220> FEATURE:
<221> NAME/KEY: misc_feature
<222> LOCATION: (2)..(4)
<223> OTHER INFORMATION: Xaa can be any naturally occurring amino acid

<400> SEQUENCE: 13

Trp Xaa Xaa Xaa Ser Leu Cys
1               5

<210> SEQ ID NO 14
<211> LENGTH: 9
<212> TYPE: PRT
<213> ORGANISM: Artificial
<220> FEATURE:
<223> OTHER INFORMATION: Rep structural motif
<220> FEATURE:
<221> NAME/KEY: misc_feature
<222> LOCATION: (1)..(1)
<223> OTHER INFORMATION: Xaa may be Ser or Ala
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 14

Xaa Phe Xaa Xaa Ala Xaa Val Ala Ser
1               5

<210> SEQ ID NO 15
<211> LENGTH: 5
<212> TYPE: PRT
<213> ORGANISM: Artificial
<220> FEATURE:
<223> OTHER INFORMATION: Rep structural motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 15

Trp Gly Xaa Val Leu
1               5

<210> SEQ ID NO 16
<211> LENGTH: 20
<212> TYPE: PRT
<213> ORGANISM: Artificial
<220> FEATURE:
<223> OTHER INFORMATION: Peptide aptamer sequence

<400> SEQUENCE: 16

Gly Phe Arg Ala Pro Gly Leu Ser Pro Thr Arg Pro Ser Cys Leu Ile
```

```
                   1               5                  10                  15

Cys Ser Thr Leu
            20

<210> SEQ ID NO 17
<211> LENGTH: 18
<212> TYPE: PRT
<213> ORGANISM: Artificial
<220> FEATURE:
<223> OTHER INFORMATION: Peptide aptamer sequence

<400> SEQUENCE: 17

Asn Glu Cys Leu Ile Cys His Met Leu Gly Ile Arg Glu Phe Gly Leu
1               5                  10                  15

Ser Ala

<210> SEQ ID NO 18
<211> LENGTH: 20
<212> TYPE: PRT
<213> ORGANISM: Artificial
<220> FEATURE:
<223> OTHER INFORMATION: Peptide aptamer sequence

<400> SEQUENCE: 18

Gly Thr Leu Trp Arg Arg Cys Ala Ser Ser Trp Ala Phe Pro Pro Asp
1               5                  10                  15

Cys Pro Ser Ala
            20

<210> SEQ ID NO 19
<211> LENGTH: 20
<212> TYPE: PRT
<213> ORGANISM: Artificial
<220> FEATURE:
<223> OTHER INFORMATION: Peptide aptamer sequence

<400> SEQUENCE: 19

Arg Arg Ala Leu Arg His Cys Thr Gly Cys Met Leu Ser Gln Arg Leu
1               5                  10                  15

Gly Thr Ala Leu
            20

<210> SEQ ID NO 20
<211> LENGTH: 20
<212> TYPE: PRT
<213> ORGANISM: Artificial
<220> FEATURE:
<223> OTHER INFORMATION: Peptide aptamer sequence

<400> SEQUENCE: 20

His Ser Met His Ser Cys Ser Val Gly Arg Cys Leu Val Asp Val Lys
1               5                  10                  15

Val Val Val Ser
            20

<210> SEQ ID NO 21
<211> LENGTH: 20
<212> TYPE: PRT
<213> ORGANISM: Artificial
<220> FEATURE:
<223> OTHER INFORMATION: Peptide aptamer sequence

<400> SEQUENCE: 21

Trp Met Val Cys Ala Gly Cys Gly Ala Leu Arg Thr Arg Gln Val Thr
```

Leu His Pro Gly
            20

<210> SEQ ID NO 22
<211> LENGTH: 19
<212> TYPE: PRT
<213> ORGANISM: Artificial
<220> FEATURE:
<223> OTHER INFORMATION: Peptide aptamer sequence

<400> SEQUENCE: 22

Gly Gly Phe Val Pro Met Arg Leu Cys Thr Cys Leu Leu Ile Val Arg
1               5                   10                  15

Leu Phe Ile

<210> SEQ ID NO 23
<211> LENGTH: 20
<212> TYPE: PRT
<213> ORGANISM: Artificial
<220> FEATURE:
<223> OTHER INFORMATION: Peptide aptamer sequence

<400> SEQUENCE: 23

Val Pro Gln Pro Leu Asn Cys Asp Leu Cys Val Leu Met Gly Gly Ala
1               5                   10                  15

Ser Ser Ser Arg
            20

<210> SEQ ID NO 24
<211> LENGTH: 20
<212> TYPE: PRT
<213> ORGANISM: Artificial
<220> FEATURE:
<223> OTHER INFORMATION: Peptide aptamer sequence

<400> SEQUENCE: 24

Arg Arg Asp Tyr Arg Lys Phe Phe Ala Leu Asn Cys Gln Leu Cys Arg
1               5                   10                  15

Leu Thr Val Thr
            20

<210> SEQ ID NO 25
<211> LENGTH: 20
<212> TYPE: PRT
<213> ORGANISM: Artificial
<220> FEATURE:
<223> OTHER INFORMATION: Peptide aptamer sequence

<400> SEQUENCE: 25

Cys Arg Thr Arg Gly Cys Gly Cys His Leu Cys Arg Met Leu Ser Gln
1               5                   10                  15

Phe Thr Gly Gly
            20

<210> SEQ ID NO 26
<211> LENGTH: 20
<212> TYPE: PRT
<213> ORGANISM: Artificial
<220> FEATURE:
<223> OTHER INFORMATION: Peptide aptamer sequence

<400> SEQUENCE: 26

Met Arg Leu Gly Lys Gly Trp Asn Leu Met Phe Leu Glu Glu Val Ser
1               5                   10                  15

```
Val Leu Asp Ala
            20

<210> SEQ ID NO 27
<211> LENGTH: 20
<212> TYPE: PRT
<213> ORGANISM: Artificial
<220> FEATURE:
<223> OTHER INFORMATION: Peptide aptamer sequence

<400> SEQUENCE: 27

Arg Asp Pro Gln Leu Gly Gln Val Ala Gln Thr Trp Gly Cys Arg Leu
1               5                   10                  15

Cys Leu Leu Glu
            20

<210> SEQ ID NO 28
<211> LENGTH: 20
<212> TYPE: PRT
<213> ORGANISM: Artificial
<220> FEATURE:
<223> OTHER INFORMATION: Peptide aptamer sequence

<400> SEQUENCE: 28

Leu Val Ser Glu Ser Cys Gly Ser Trp Phe Cys Leu Cys Pro Trp Glu
1               5                   10                  15

Val Leu Asn Trp
            20

<210> SEQ ID NO 29
<211> LENGTH: 20
<212> TYPE: PRT
<213> ORGANISM: Artificial
<220> FEATURE:
<223> OTHER INFORMATION: Peptide aptamer sequence

<400> SEQUENCE: 29

Leu Gln Tyr Ser Trp Asn Leu Tyr Ser Val Ala Ser Phe Lys Thr Arg
1               5                   10                  15

Arg Val Ser Ser
            20

<210> SEQ ID NO 30
<211> LENGTH: 20
<212> TYPE: PRT
<213> ORGANISM: Artificial
<220> FEATURE:
<223> OTHER INFORMATION: Peptide aptamer sequence

<400> SEQUENCE: 30

Arg Leu Gln Glu Ser Ser Ile Asp Leu Thr Pro Gly Ile Tyr Leu Gly
1               5                   10                  15

Met Asp Phe Val
            20

<210> SEQ ID NO 31
<211> LENGTH: 20
<212> TYPE: PRT
<213> ORGANISM: Artificial
<220> FEATURE:
<223> OTHER INFORMATION: Peptide aptamer sequence

<400> SEQUENCE: 31
```

```
Cys Tyr Met Glu Val Glu Gly Arg Pro Arg Arg Trp Ala Asp Ser Phe
1               5                   10                  15

Phe Val Ala Trp
            20
```

<210> SEQ ID NO 32
<211> LENGTH: 20
<212> TYPE: PRT
<213> ORGANISM: Artificial
<220> FEATURE:
<223> OTHER INFORMATION: Peptide aptamer sequence

<400> SEQUENCE: 32

```
Ser Glu Ser Phe Val Cys Lys Thr Cys His Met Leu Arg Val Ser Asp
1               5                   10                  15

Ala Val Gly Ala
            20
```

<210> SEQ ID NO 33
<211> LENGTH: 20
<212> TYPE: PRT
<213> ORGANISM: Artificial
<220> FEATURE:
<223> OTHER INFORMATION: Peptide aptamer sequence

<400> SEQUENCE: 33

```
Met His Val Ser Leu Val Phe Pro Trp Arg Leu Thr Gly His Ile Gln
1               5                   10                  15

Gln Tyr Lys Val
            20
```

<210> SEQ ID NO 34
<211> LENGTH: 20
<212> TYPE: PRT
<213> ORGANISM: Artificial
<220> FEATURE:
<223> OTHER INFORMATION: Peptide aptamer sequence

<400> SEQUENCE: 34

```
Gly Arg Cys Asn Leu Gln Gly Met Ser Phe Met Gly Val Gly Arg Ser
1               5                   10                  15

Val Trp Phe Glu
            20
```

<210> SEQ ID NO 35
<211> LENGTH: 20
<212> TYPE: PRT
<213> ORGANISM: Artificial
<220> FEATURE:
<223> OTHER INFORMATION: Peptide aptamer sequence

<400> SEQUENCE: 35

```
Val Val Gly Gly Ser Leu Arg Asp Glu Trp Lys Trp Trp Arg Glu Gly
1               5                   10                  15

Arg Ser Leu Pro
            20
```

<210> SEQ ID NO 36
<211> LENGTH: 20
<212> TYPE: PRT
<213> ORGANISM: Artificial
<220> FEATURE:
<223> OTHER INFORMATION: Peptide aptamer sequence

<400> SEQUENCE: 36

```
Ala Lys Asp Val Glu Arg Gly Ala Gly Gly Lys Ile Lys Ala Cys Glu
1               5                   10                  15

Leu Cys Arg Leu
            20

<210> SEQ ID NO 37
<211> LENGTH: 20
<212> TYPE: PRT
<213> ORGANISM: Artificial
<220> FEATURE:
<223> OTHER INFORMATION: Peptide aptamer sequence

<400> SEQUENCE: 37

Val Glu Thr Phe Lys Ala Arg Ala Arg Gln Thr Pro Ser Cys Asp Leu
1               5                   10                  15

Cys Pro Lys Thr
            20

<210> SEQ ID NO 38
<211> LENGTH: 20
<212> TYPE: PRT
<213> ORGANISM: Artificial
<220> FEATURE:
<223> OTHER INFORMATION: Peptide aptamer sequence

<400> SEQUENCE: 38

Thr Glu Leu Trp Trp Ala Asp Phe Ala Lys Met His Met Glu Gly Gly
1               5                   10                  15

Lys Gly Met Cys
            20

<210> SEQ ID NO 39
<211> LENGTH: 20
<212> TYPE: PRT
<213> ORGANISM: Artificial
<220> FEATURE:
<223> OTHER INFORMATION: Peptide aptamer sequence

<400> SEQUENCE: 39

Arg His Arg Cys Thr Ser Arg Ala Pro Arg Gln Trp Phe Arg Pro His
1               5                   10                  15

Arg Asp Ser Pro
            20

<210> SEQ ID NO 40
<211> LENGTH: 20
<212> TYPE: PRT
<213> ORGANISM: Artificial
<220> FEATURE:
<223> OTHER INFORMATION: Peptide aptamer sequence

<400> SEQUENCE: 40

Arg Tyr Arg Val Ser Ala Gly Pro Leu Cys Ser Leu Cys Ser Leu Trp
1               5                   10                  15

Gly Ser Val Gly
            20

<210> SEQ ID NO 41
<211> LENGTH: 20
<212> TYPE: PRT
<213> ORGANISM: Artificial
<220> FEATURE:
<223> OTHER INFORMATION: Peptide aptamer sequence
```

```
<400> SEQUENCE: 41

Glu Glu Gly Leu Ala Ala Ile Thr His Thr Trp Leu Thr Met Cys Phe
1               5                   10                  15

Ala Ala Gly Leu
            20

<210> SEQ ID NO 42
<211> LENGTH: 20
<212> TYPE: PRT
<213> ORGANISM: Artificial
<220> FEATURE:
<223> OTHER INFORMATION: Peptide aptamer sequence

<400> SEQUENCE: 42

Ala Ala Phe Leu Glu Ser Val Arg Ser Tyr Trp Ser Arg Phe Val Arg
1               5                   10                  15

His Val Gln Gly
            20

<210> SEQ ID NO 43
<211> LENGTH: 20
<212> TYPE: PRT
<213> ORGANISM: Artificial
<220> FEATURE:
<223> OTHER INFORMATION: Peptide aptamer sequence

<400> SEQUENCE: 43

Arg Ala Met Cys Asp Lys Asp Lys Ser Val Cys Ser Ile Leu Ala Leu
1               5                   10                  15

Tyr Val Gln Val
            20

<210> SEQ ID NO 44
<211> LENGTH: 20
<212> TYPE: PRT
<213> ORGANISM: Artificial
<220> FEATURE:
<223> OTHER INFORMATION: Peptide aptamer sequence

<400> SEQUENCE: 44

Cys Trp Trp Leu Arg Glu Ile Gly Thr Phe Arg Cys Val Thr Leu Gln
1               5                   10                  15

His Val Ala Gly
            20

<210> SEQ ID NO 45
<211> LENGTH: 20
<212> TYPE: PRT
<213> ORGANISM: Artificial
<220> FEATURE:
<223> OTHER INFORMATION: Peptide aptamer sequence

<400> SEQUENCE: 45

Phe Glu Ser Ala Trp Ser Thr Leu Met Gly Ala Met Thr Pro Met Val
1               5                   10                  15

Leu Asp Glu Thr
            20

<210> SEQ ID NO 46
<211> LENGTH: 20
<212> TYPE: PRT
<213> ORGANISM: Artificial
<220> FEATURE:
<223> OTHER INFORMATION: Peptide aptamer sequence
```

-continued

```
<400> SEQUENCE: 46

Gln Ala Leu Val Val Ser Pro Glu Thr Phe Leu Cys Leu Glu Ala Leu
1               5                   10                  15

Gly Val Asn Ser
            20

<210> SEQ ID NO 47
<211> LENGTH: 20
<212> TYPE: PRT
<213> ORGANISM: Artificial
<220> FEATURE:
<223> OTHER INFORMATION: Peptide aptamer sequence

<400> SEQUENCE: 47

Gly Gly Arg Gln Thr Glu Pro Ser Leu Thr Leu Leu Ala Asp Leu Thr
1               5                   10                  15

Leu Leu Leu Ser
            20

<210> SEQ ID NO 48
<211> LENGTH: 20
<212> TYPE: PRT
<213> ORGANISM: Artificial
<220> FEATURE:
<223> OTHER INFORMATION: Peptide aptamer sequence

<400> SEQUENCE: 48

Gly Ser Arg Ala Glu Leu Ser Ala Pro Glu Val Ala Trp Leu Leu Phe
1               5                   10                  15

Cys Thr Pro Gly
            20

<210> SEQ ID NO 49
<211> LENGTH: 20
<212> TYPE: PRT
<213> ORGANISM: Artificial
<220> FEATURE:
<223> OTHER INFORMATION: Peptide aptamer sequence

<400> SEQUENCE: 49

Arg Tyr Ser Ala Val Cys Arg Asp Cys Tyr Glu Gly His Gly Arg Gly
1               5                   10                  15

Leu Trp Tyr Met
            20

<210> SEQ ID NO 50
<211> LENGTH: 20
<212> TYPE: PRT
<213> ORGANISM: Artificial
<220> FEATURE:
<223> OTHER INFORMATION: Peptide aptamer sequence

<400> SEQUENCE: 50

Gly Gly Trp Leu Val Thr Ile Val Glu Gly Pro Leu Ala Ile Cys Cys
1               5                   10                  15

Leu Arg Asp Asp
            20

<210> SEQ ID NO 51
<211> LENGTH: 20
<212> TYPE: PRT
<213> ORGANISM: Artificial
<220> FEATURE:
```

-continued

<223> OTHER INFORMATION: Peptide aptamer sequence

<400> SEQUENCE: 51

Pro Ser Ile Glu Ser Gly Trp Val Gly Asp Gln Ala Val Ala Pro Cys
1               5                   10                  15

Asp Leu Ser Val
            20

<210> SEQ ID NO 52
<211> LENGTH: 20
<212> TYPE: PRT
<213> ORGANISM: Artificial
<220> FEATURE:
<223> OTHER INFORMATION: Peptide aptamer sequence

<400> SEQUENCE: 52

Thr Trp Gly Ala Trp Lys Arg Asp Ile Val Leu Val Ser Glu Ile Gly
1               5                   10                  15

Phe Thr Trp Gly
            20

<210> SEQ ID NO 53
<211> LENGTH: 20
<212> TYPE: PRT
<213> ORGANISM: Artificial
<220> FEATURE:
<223> OTHER INFORMATION: Peptide aptamer sequence

<400> SEQUENCE: 53

Arg Leu Gly Gly Gly Arg Pro Lys Leu Trp His Phe Ser Pro Asn Leu
1               5                   10                  15

Met Ala Gly Phe
            20

<210> SEQ ID NO 54
<211> LENGTH: 20
<212> TYPE: PRT
<213> ORGANISM: Artificial
<220> FEATURE:
<223> OTHER INFORMATION: Peptide aptamer sequence

<400> SEQUENCE: 54

Glu Arg Val His Val Cys Phe Ser Arg Lys Cys Thr Ala Leu Ser Val
1               5                   10                  15

Asp Ser Ser Val
            20

<210> SEQ ID NO 55
<211> LENGTH: 20
<212> TYPE: PRT
<213> ORGANISM: Artificial
<220> FEATURE:
<223> OTHER INFORMATION: Peptide aptamer sequence

<400> SEQUENCE: 55

Arg Glu Arg Gly Gly Asp Asp Tyr Arg Arg Met Met His Pro Gly Ala
1               5                   10                  15

Ala Ser Gly Pro
            20

<210> SEQ ID NO 56
<211> LENGTH: 20
<212> TYPE: PRT
<213> ORGANISM: Artificial

```
<220> FEATURE:
<223> OTHER INFORMATION: Peptide aptamer sequence

<400> SEQUENCE: 56

Arg Leu Val Val Gly Cys Glu Trp Arg Ile Gly Cys Ser Thr Gly Ser
1               5                   10                  15

Gly Pro Arg Gly
            20

<210> SEQ ID NO 57
<211> LENGTH: 20
<212> TYPE: PRT
<213> ORGANISM: Artificial
<220> FEATURE:
<223> OTHER INFORMATION: Peptide aptamer sequence

<400> SEQUENCE: 57

Ala Ser Leu Ile Gly Val Gly Ile Ala Ser Met His Gly Met Gln Thr
1               5                   10                  15

Asp Gly Ile Tyr
            20

<210> SEQ ID NO 58
<211> LENGTH: 20
<212> TYPE: PRT
<213> ORGANISM: Artificial
<220> FEATURE:
<223> OTHER INFORMATION: Peptide aptamer sequence

<400> SEQUENCE: 58

Val Gly Leu Met Glu Trp Ala Val Trp Ser Leu Glu Val Arg Glu Lys
1               5                   10                  15

Leu Tyr Ser Cys
            20

<210> SEQ ID NO 59
<211> LENGTH: 20
<212> TYPE: PRT
<213> ORGANISM: Artificial
<220> FEATURE:
<223> OTHER INFORMATION: Peptide aptamer sequence

<400> SEQUENCE: 59

Val Leu Gly Arg Leu Gly Gly Ala Gly Gly Cys Ser Leu Cys Asp Gln
1               5                   10                  15

Leu Glu Ala Leu
            20

<210> SEQ ID NO 60
<211> LENGTH: 20
<212> TYPE: PRT
<213> ORGANISM: Artificial
<220> FEATURE:
<223> OTHER INFORMATION: Peptide aptamer sequence

<400> SEQUENCE: 60

Ile Trp Ile Asn Pro Asn Gly Leu Trp Trp Thr Lys Val Gly Leu Asn
1               5                   10                  15

Pro Tyr Ala Val
            20

<210> SEQ ID NO 61
<211> LENGTH: 20
<212> TYPE: PRT
```

<213> ORGANISM: Artificial
<220> FEATURE:
<223> OTHER INFORMATION: Peptide aptamer sequence

<400> SEQUENCE: 61

Arg His Glu Ser Ala Leu His Lys Ser Cys Glu Leu Cys Tyr Cys Pro
1               5                   10                  15

Trp Lys Val Cys
            20

<210> SEQ ID NO 62
<211> LENGTH: 20
<212> TYPE: PRT
<213> ORGANISM: Artificial
<220> FEATURE:
<223> OTHER INFORMATION: Peptide aptamer sequence

<400> SEQUENCE: 62

Val Arg Ser His Arg Arg Tyr Gln Arg Asn Trp Glu Pro Val Val Ser
1               5                   10                  15

Trp Phe Ser Ser
            20

<210> SEQ ID NO 63
<211> LENGTH: 11
<212> TYPE: PRT
<213> ORGANISM: Artificial
<220> FEATURE:
<223> OTHER INFORMATION: Peptide aptamer sequence

<400> SEQUENCE: 63

Trp Cys Gly Pro Gln Val Ser Ala Arg Cys Lys
1               5                   10

<210> SEQ ID NO 64
<211> LENGTH: 20
<212> TYPE: PRT
<213> ORGANISM: Artificial
<220> FEATURE:
<223> OTHER INFORMATION: Peptide aptamer sequence

<400> SEQUENCE: 64

Ser Cys Asp Glu Ala Phe Asp Ala Ala Ser Val Ala Ser Glu Leu Phe
1               5                   10                  15

Cys Gln Pro Tyr
            20

<210> SEQ ID NO 65
<211> LENGTH: 42
<212> TYPE: PRT
<213> ORGANISM: Artificial
<220> FEATURE:
<223> OTHER INFORMATION: Peptide aptamer sequence

<400> SEQUENCE: 65

Ala Arg Met Ala Leu Ser Leu Arg Glu Trp Glu Tyr Leu Phe Phe Lys
1               5                   10                  15

Asp Ala Pro Ser Gly Pro Gly Leu Gln Gly Leu Ser Leu Ala Ser Arg
            20                  25                  30

Leu Asn Leu Val Ile Leu Arg Gly Tyr Gly
            35                  40

<210> SEQ ID NO 66
<211> LENGTH: 20

```
<212> TYPE: PRT
<213> ORGANISM: Artificial
<220> FEATURE:
<223> OTHER INFORMATION: Peptide aptamer sequence

<400> SEQUENCE: 66

Arg Ser Tyr Gly Gly Gly Glu Ile Pro Ser Val Thr Met His Cys Trp
1               5                   10                  15

Ile His Cys Asp
            20

<210> SEQ ID NO 67
<211> LENGTH: 20
<212> TYPE: PRT
<213> ORGANISM: Artificial
<220> FEATURE:
<223> OTHER INFORMATION: Peptide aptamer sequence

<400> SEQUENCE: 67

Ser Ser Ser Arg Trp Val Pro Phe Ala Leu Gln Asp Pro Leu Phe Ser
1               5                   10                  15

Ser Asp Asp Trp
            20

<210> SEQ ID NO 68
<211> LENGTH: 20
<212> TYPE: PRT
<213> ORGANISM: Artificial
<220> FEATURE:
<223> OTHER INFORMATION: Peptide aptamer sequence

<400> SEQUENCE: 68

Tyr Leu Trp Ser Ser Lys Met Asp Glu Trp Val Ala Met Asp Asp Val
1               5                   10                  15

Tyr Ala Ala Cys
            20

<210> SEQ ID NO 69
<211> LENGTH: 20
<212> TYPE: PRT
<213> ORGANISM: Artificial
<220> FEATURE:
<223> OTHER INFORMATION: Peptide aptamer sequence

<400> SEQUENCE: 69

Thr Trp Gly Leu Val Cys Thr Gly Thr Gly Trp Gly Leu Leu Asp Thr
1               5                   10                  15

Val Val Arg Ala
            20

<210> SEQ ID NO 70
<211> LENGTH: 19
<212> TYPE: PRT
<213> ORGANISM: Artificial
<220> FEATURE:
<223> OTHER INFORMATION: Peptide aptamer sequence

<400> SEQUENCE: 70

Val Tyr Glu Trp Gly Asp Val Leu Cys Gly Gly Ser Met Ala Ile Gln
1               5                   10                  15

Trp Gly Leu

<210> SEQ ID NO 71
<211> LENGTH: 20
```

```
<212> TYPE: PRT
<213> ORGANISM: Artificial
<220> FEATURE:
<223> OTHER INFORMATION: Peptide aptamer sequence

<400> SEQUENCE: 71

Ala Ser Asn Gly Glu Ile Ala Tyr Cys Val Glu Gln Ala Met Leu Leu
1               5                   10                  15

Leu Cys Phe His
            20

<210> SEQ ID NO 72
<211> LENGTH: 19
<212> TYPE: PRT
<213> ORGANISM: Artificial
<220> FEATURE:
<223> OTHER INFORMATION: Peptide aptamer sequence

<400> SEQUENCE: 72

Glu Leu Ile Val His Glu Trp Pro Leu Ile Leu Ser Arg Val Gly Arg
1               5                   10                  15

Ile Val Leu

<210> SEQ ID NO 73
<211> LENGTH: 20
<212> TYPE: PRT
<213> ORGANISM: Artificial
<220> FEATURE:
<223> OTHER INFORMATION: Peptide aptamer sequence

<400> SEQUENCE: 73

Gly Arg Val Gln Leu Glu Ile Leu Val Ser Glu Ala Glu Glu Gly Val
1               5                   10                  15

Ser Pro Phe Leu
            20

<210> SEQ ID NO 74
<211> LENGTH: 20
<212> TYPE: PRT
<213> ORGANISM: Artificial
<220> FEATURE:
<223> OTHER INFORMATION: Peptide aptamer sequence

<400> SEQUENCE: 74

Arg Asp Ala Glu Trp Gln Asp Val Leu Gly Arg Ala Arg Ala Val His
1               5                   10                  15

Leu Arg Gly Arg
            20

<210> SEQ ID NO 75
<211> LENGTH: 20
<212> TYPE: PRT
<213> ORGANISM: Artificial
<220> FEATURE:
<223> OTHER INFORMATION: Peptide aptamer sequence

<400> SEQUENCE: 75

Gly Leu Lys Trp Lys Ser Asp Asn Gly Cys Val Tyr Val Ser Phe Met
1               5                   10                  15

Arg Gly Gly Val
            20

<210> SEQ ID NO 76
<211> LENGTH: 20
```

```
<212> TYPE: PRT
<213> ORGANISM: Artificial
<220> FEATURE:
<223> OTHER INFORMATION: Peptide aptamer sequence

<400> SEQUENCE: 76

Ser Ser Ser Pro Val Pro Tyr Ser Gly Gly Thr Cys Asn Leu Cys Ser
1               5                   10                  15

Met Arg Met Trp
            20

<210> SEQ ID NO 77
<211> LENGTH: 20
<212> TYPE: PRT
<213> ORGANISM: Artificial
<220> FEATURE:
<223> OTHER INFORMATION: Peptide aptamer sequence

<400> SEQUENCE: 77

Glu Trp Glu Asp Pro Gln Tyr Ala Gly Trp Glu Leu Phe Ser Ile Ser
1               5                   10                  15

Asp Leu Val His
            20

<210> SEQ ID NO 78
<211> LENGTH: 20
<212> TYPE: PRT
<213> ORGANISM: Artificial
<220> FEATURE:
<223> OTHER INFORMATION: Peptide aptamer sequence

<400> SEQUENCE: 78

Pro Met Val Arg Thr Glu Trp Pro Leu Cys Ala Ile Ile Pro Leu Ser
1               5                   10                  15

Met Leu Tyr Gln
            20

<210> SEQ ID NO 79
<211> LENGTH: 20
<212> TYPE: PRT
<213> ORGANISM: Artificial
<220> FEATURE:
<223> OTHER INFORMATION: Peptide aptamer sequence

<400> SEQUENCE: 79

Arg Ala Gly Trp His Glu Arg Val Arg Gln Trp Trp Ala Ile Glu Cys
1               5                   10                  15

Thr Leu Glu Val
            20

<210> SEQ ID NO 80
<211> LENGTH: 20
<212> TYPE: PRT
<213> ORGANISM: Artificial
<220> FEATURE:
<223> OTHER INFORMATION: Peptide aptamer sequence

<400> SEQUENCE: 80

Ser Val Arg Cys Trp Tyr Val Leu Arg Cys Ser Phe Leu Val Gly Ser
1               5                   10                  15

Gly Ser Ser Val
            20

<210> SEQ ID NO 81
```

```
<211> LENGTH: 20
<212> TYPE: PRT
<213> ORGANISM: Artificial
<220> FEATURE:
<223> OTHER INFORMATION: Peptide aptamer sequence

<400> SEQUENCE: 81

Arg Ser Cys Val Leu Cys Ala Tyr Gly Ser Arg Thr Phe Asn Gly Ser
1               5                   10                  15

Tyr Leu Leu Phe
            20

<210> SEQ ID NO 82
<211> LENGTH: 46
<212> TYPE: PRT
<213> ORGANISM: Artificial
<220> FEATURE:
<223> OTHER INFORMATION: Peptide aptamer sequence

<400> SEQUENCE: 82

Gly Arg Gly Gly Cys Met Leu Cys Asp Val Asp Gly Ser Ser Ala Trp
1               5                   10                  15

Leu His Thr Glu Gly Arg Leu Thr Gly Pro Ile Thr Ser Gln Gln Cys
            20                  25                  30

Leu Ser Phe Gln Tyr Leu Gly Asn Gly Glu Phe Ile Asp Gly
        35                  40                  45

<210> SEQ ID NO 83
<211> LENGTH: 20
<212> TYPE: PRT
<213> ORGANISM: Artificial
<220> FEATURE:
<223> OTHER INFORMATION: Peptide aptamer sequence

<400> SEQUENCE: 83

Thr Leu Glu Thr Leu Asp Met Gly Asn Pro Leu Tyr Thr Cys Val Leu
1               5                   10                  15

Met Asp Trp Met
            20

<210> SEQ ID NO 84
<211> LENGTH: 42
<212> TYPE: PRT
<213> ORGANISM: Artificial
<220> FEATURE:
<223> OTHER INFORMATION: Peptide aptamer sequence

<400> SEQUENCE: 84

Leu Val Met Gly Trp Arg Ser Glu Val Ser Ser Leu Gln Lys Thr
1               5                   10                  15

Gly Thr Gly Gly Pro Thr Leu Arg Lys Cys Gln Leu Cys Arg Gly
            20                  25                  30

Ser Arg Tyr Thr Leu Lys Tyr Tyr Pro Cys
        35                  40

<210> SEQ ID NO 85
<211> LENGTH: 13
<212> TYPE: PRT
<213> ORGANISM: Artificial
<220> FEATURE:
<223> OTHER INFORMATION: Peptide aptamer sequence

<400> SEQUENCE: 85

Arg Pro Gly Cys Pro Phe Cys Thr Ser Trp Arg Cys Gly
```

```
<210> SEQ ID NO 86
<211> LENGTH: 20
<212> TYPE: PRT
<213> ORGANISM: Artificial
<220> FEATURE:
<223> OTHER INFORMATION: Peptide aptamer sequence

<400> SEQUENCE: 86

Phe Cys Pro Glu Cys Gln Met Val Ala Gly Ala Glu Asp Gly Asp Ala
1               5                   10                  15

Ile Asp Leu Gln
            20

<210> SEQ ID NO 87
<211> LENGTH: 20
<212> TYPE: PRT
<213> ORGANISM: Artificial
<220> FEATURE:
<223> OTHER INFORMATION: Peptide aptamer sequence

<400> SEQUENCE: 87

Arg Arg Cys Met Leu Cys Thr Ser Asp Lys Pro Gly Gly Asp Gln Gly
1               5                   10                  15

Ala Leu Asn Met
            20

<210> SEQ ID NO 88
<211> LENGTH: 19
<212> TYPE: PRT
<213> ORGANISM: Artificial
<220> FEATURE:
<223> OTHER INFORMATION: Peptide aptamer sequence

<400> SEQUENCE: 88

Leu Trp Gly Gly Gly Thr Ala Trp Asp Phe Phe Val Trp Gly Glu Asp
1               5                   10                  15

Ser Ala Cys

<210> SEQ ID NO 89
<211> LENGTH: 20
<212> TYPE: PRT
<213> ORGANISM: Artificial
<220> FEATURE:
<223> OTHER INFORMATION: Peptide aptamer sequence

<400> SEQUENCE: 89

Gly Met Ser Gly Arg Ile Pro Glu Pro Asp Asp Trp Val Val Leu Phe
1               5                   10                  15

Ile Thr Gly Cys
            20

<210> SEQ ID NO 90
<211> LENGTH: 20
<212> TYPE: PRT
<213> ORGANISM: Artificial
<220> FEATURE:
<223> OTHER INFORMATION: Peptide aptamer sequence

<400> SEQUENCE: 90

Gly Gly Thr Asn Ala Leu Leu Gln Lys Val Phe Phe Gly Glu Val Gly
1               5                   10                  15

Val Ala Ser Met
```

```
<210> SEQ ID NO 91
<211> LENGTH: 20
<212> TYPE: PRT
<213> ORGANISM: Artificial
<220> FEATURE:
<223> OTHER INFORMATION: Peptide aptamer sequence

<400> SEQUENCE: 91

Glu Cys Cys Leu Phe Pro Ile Phe Ala Met Ala Asp Ser Phe Pro Cys
1               5                   10                  15

Pro Ser Pro Val
            20

<210> SEQ ID NO 92
<211> LENGTH: 20
<212> TYPE: PRT
<213> ORGANISM: Artificial
<220> FEATURE:
<223> OTHER INFORMATION: Peptide aptamer sequence

<400> SEQUENCE: 92

Met Leu Glu Gly Pro Leu Asp Gln Gly Leu Met Met Gly Thr Cys Cys
1               5                   10                  15

Trp Glu Cys Ser
            20

<210> SEQ ID NO 93
<211> LENGTH: 20
<212> TYPE: PRT
<213> ORGANISM: Artificial
<220> FEATURE:
<223> OTHER INFORMATION: Peptide aptamer sequence

<400> SEQUENCE: 93

Thr Pro Ser Val Thr Trp Leu Ala Glu Trp Cys Ser Cys Val Phe Cys
1               5                   10                  15

Arg Asp Ala Ser
            20

<210> SEQ ID NO 94
<211> LENGTH: 17
<212> TYPE: PRT
<213> ORGANISM: Artificial
<220> FEATURE:
<223> OTHER INFORMATION: Peptide aptamer sequence

<400> SEQUENCE: 94

Ser Trp Trp Trp Ala Asn Asn Ser Leu Cys Arg Glu Trp Glu Phe Ala
1               5                   10                  15

Cys

<210> SEQ ID NO 95
<211> LENGTH: 20
<212> TYPE: PRT
<213> ORGANISM: Artificial
<220> FEATURE:
<223> OTHER INFORMATION: Peptide aptamer sequence

<400> SEQUENCE: 95

Trp Asn Met Leu Ala Phe Gly Gly Ala Leu Val Ala Ser Gly Leu Leu
1               5                   10                  15

Arg Gly Trp Glu
```

20

<210> SEQ ID NO 96
<211> LENGTH: 20
<212> TYPE: PRT
<213> ORGANISM: Artificial
<220> FEATURE:
<223> OTHER INFORMATION: Peptide aptamer sequence

<400> SEQUENCE: 96

Asp Lys Cys Asp Asp Val Glu Pro Phe Leu Trp Trp Gly Gln Gln Cys
1               5                   10                  15

Phe Phe Asp Val
            20

<210> SEQ ID NO 97
<211> LENGTH: 20
<212> TYPE: PRT
<213> ORGANISM: Artificial
<220> FEATURE:
<223> OTHER INFORMATION: Peptide aptamer sequence

<400> SEQUENCE: 97

Gly Ser Pro Ser Arg Ile Ser Tyr Thr Cys Leu Ser Pro Asp Val Thr
1               5                   10                  15

Leu Leu Phe Leu
            20

<210> SEQ ID NO 98
<211> LENGTH: 20
<212> TYPE: PRT
<213> ORGANISM: Artificial
<220> FEATURE:
<223> OTHER INFORMATION: Peptide aptamer sequence

<400> SEQUENCE: 98

Met Gly Ile Glu Ala Cys Ser Ile Thr Glu Cys Thr Ser Gln His Cys
1               5                   10                  15

Asn Glu Val Ala
            20

<210> SEQ ID NO 99
<211> LENGTH: 20
<212> TYPE: PRT
<213> ORGANISM: Artificial
<220> FEATURE:
<223> OTHER INFORMATION: Peptide aptamer sequence

<400> SEQUENCE: 99

Cys Leu Asp Asn Leu Cys Trp Glu Leu Gly Gly Gly Phe Pro Val Ile
1               5                   10                  15

Leu Ile His Cys
            20

<210> SEQ ID NO 100
<211> LENGTH: 20
<212> TYPE: PRT
<213> ORGANISM: Artificial
<220> FEATURE:
<223> OTHER INFORMATION: Peptide aptamer sequence

<400> SEQUENCE: 100

His Val His Gly Ser Cys Pro Ser Met Gly Trp Ser Ser Asn Ser Trp
1               5                   10                  15

Cys Ser Val Phe
            20

<210> SEQ ID NO 101
<211> LENGTH: 20
<212> TYPE: PRT
<213> ORGANISM: Artificial
<220> FEATURE:
<223> OTHER INFORMATION: Peptide aptamer sequence

<400> SEQUENCE: 101

Pro Leu Glu Leu Glu Phe Ala Val Cys Gly Cys Ser Trp Leu Val Ala
1               5                   10                  15

Leu Asp Trp Ser
            20

<210> SEQ ID NO 102
<211> LENGTH: 20
<212> TYPE: PRT
<213> ORGANISM: Artificial
<220> FEATURE:
<223> OTHER INFORMATION: Peptide aptamer sequence

<400> SEQUENCE: 102

Ala Trp Asp Ser Glu Ser Leu Ala Thr Trp Ala Ser Val Met Pro Trp
1               5                   10                  15

Pro Tyr Pro Thr
            20

<210> SEQ ID NO 103
<211> LENGTH: 20
<212> TYPE: PRT
<213> ORGANISM: Artificial
<220> FEATURE:
<223> OTHER INFORMATION: Peptide aptamer sequence

<400> SEQUENCE: 103

Thr Gly Cys His Tyr Lys Gly Ala Arg Cys Cys Arg Leu Thr Trp Asp
1               5                   10                  15

Val Leu Ile Leu
            20

<210> SEQ ID NO 104
<211> LENGTH: 18
<212> TYPE: PRT
<213> ORGANISM: Artificial
<220> FEATURE:
<223> OTHER INFORMATION: Peptide aptamer sequence

<400> SEQUENCE: 104

Pro Leu Ser Gly Arg Gln Gly Val His Leu Tyr Phe Leu Leu Leu Met
1               5                   10                  15

Pro Ala

<210> SEQ ID NO 105
<211> LENGTH: 20
<212> TYPE: PRT
<213> ORGANISM: Artificial
<220> FEATURE:
<223> OTHER INFORMATION: Peptide aptamer sequence

<400> SEQUENCE: 105

Phe Ala Val Glu Tyr Gly Ser Gln Gly Trp Gly Leu Trp Tyr Cys Val
1               5                   10                  15

Trp Leu Asp Leu
            20

<210> SEQ ID NO 106
<211> LENGTH: 20
<212> TYPE: PRT
<213> ORGANISM: Artificial
<220> FEATURE:
<223> OTHER INFORMATION: Peptide aptamer sequence

<400> SEQUENCE: 106

Phe Gln Ser Arg Met Gly Gly Gly Ser Gly Val Val Asn Ala Lys Leu
1               5                   10                  15

Trp Ala Lys Glu
            20

<210> SEQ ID NO 107
<211> LENGTH: 20
<212> TYPE: PRT
<213> ORGANISM: Artificial
<220> FEATURE:
<223> OTHER INFORMATION: Peptide aptamer sequence

<400> SEQUENCE: 107

Val Ala Ser Arg Asp Ser Gly Ala Trp Arg Glu Leu His Ser Phe Leu
1               5                   10                  15

Asn Phe Ala Ser
            20

<210> SEQ ID NO 108
<211> LENGTH: 20
<212> TYPE: PRT
<213> ORGANISM: Artificial
<220> FEATURE:
<223> OTHER INFORMATION: Peptide aptamer sequence

<400> SEQUENCE: 108

Tyr Tyr Met Ala Leu Leu Tyr Ser Gln Cys Pro Thr Val Val Leu Phe
1               5                   10                  15

Arg Met Thr Thr
            20

<210> SEQ ID NO 109
<211> LENGTH: 20
<212> TYPE: PRT
<213> ORGANISM: Artificial
<220> FEATURE:
<223> OTHER INFORMATION: Peptide aptamer sequence

<400> SEQUENCE: 109

Asp Phe Val Cys Leu Cys Leu Phe Ala Cys Thr Ser Asp Leu Ser Ala
1               5                   10                  15

Phe Arg Val Cys
            20

<210> SEQ ID NO 110
<211> LENGTH: 19
<212> TYPE: PRT
<213> ORGANISM: Artificial
<220> FEATURE:
<223> OTHER INFORMATION: Peptide aptamer sequence

<400> SEQUENCE: 110

Thr Ala Phe Arg Trp Asp Met Phe Trp Met His Thr Ser Gly Thr Trp
1               5                   10                  15

Arg Lys Pro

<210> SEQ ID NO 111
<211> LENGTH: 20
<212> TYPE: PRT
<213> ORGANISM: Artificial
<220> FEATURE:
<223> OTHER INFORMATION: Peptide aptamer sequence

<400> SEQUENCE: 111

Phe Ala Ser Gly Ser Gly Glu Pro Val Gly Leu Gly Leu Gly Ser Pro
1               5                   10                  15

Leu Glu Lys Leu
            20

<210> SEQ ID NO 112
<211> LENGTH: 19
<212> TYPE: PRT
<213> ORGANISM: Artificial
<220> FEATURE:
<223> OTHER INFORMATION: Peptide aptamer sequence

<400> SEQUENCE: 112

Val Tyr Asp Ser Ala Leu Cys Leu Val Val Gly Arg Cys Gly Leu Ile
1               5                   10                  15

Arg Cys Arg

<210> SEQ ID NO 113
<211> LENGTH: 6
<212> TYPE: PRT
<213> ORGANISM: Artificial
<220> FEATURE:
<223> OTHER INFORMATION: Peptide aptamer sequence

<400> SEQUENCE: 113

Leu Val Trp Ala Ser Met
1               5

<210> SEQ ID NO 114
<211> LENGTH: 20
<212> TYPE: PRT
<213> ORGANISM: Artificial
<220> FEATURE:
<223> OTHER INFORMATION: Peptide aptamer sequence

<400> SEQUENCE: 114

Leu His Glu Ser Cys Trp Gly Trp Ala Gly Asp Ser Ser Pro Gln Gly
1               5                   10                  15

Val Leu Ala Gly
            20

<210> SEQ ID NO 115
<211> LENGTH: 20
<212> TYPE: PRT
<213> ORGANISM: Artificial
<220> FEATURE:
<223> OTHER INFORMATION: Peptide aptamer sequence

<400> SEQUENCE: 115

Glu Leu Leu Val Ala His Leu Ile Thr Pro Trp Thr Ser Met Gly Arg
1               5                   10                  15

Thr Gln Ala Leu
            20

```
<210> SEQ ID NO 116
<211> LENGTH: 42
<212> TYPE: PRT
<213> ORGANISM: Artificial
<220> FEATURE:
<223> OTHER INFORMATION: Peptide aptamer sequence

<400> SEQUENCE: 116

Thr Asn Glu Leu Pro Leu Thr Ile Val Thr Asp Asp Val Ser Gln Leu
1               5                   10                  15

Val Ile Ser Arg Gly Pro Ala Arg His Leu Tyr Glu Leu Met Pro Glu
            20                  25                  30

Met Leu Val Leu Arg Ser Ala Arg Leu Thr
        35                  40

<210> SEQ ID NO 117
<211> LENGTH: 20
<212> TYPE: PRT
<213> ORGANISM: Artificial
<220> FEATURE:
<223> OTHER INFORMATION: Peptide aptamer sequence

<400> SEQUENCE: 117

Asp Glu Gln Glu Ser Val Cys Arg Ser Cys Lys Cys Arg Tyr Val Asp
1               5                   10                  15

Asn Trp Leu Glu
            20

<210> SEQ ID NO 118
<211> LENGTH: 20
<212> TYPE: PRT
<213> ORGANISM: Artificial
<220> FEATURE:
<223> OTHER INFORMATION: Peptide aptamer sequence

<400> SEQUENCE: 118

Val Gly Gly Met Pro Pro Leu Pro Trp Tyr Glu Pro Val Gly Leu Val
1               5                   10                  15

Trp Ser Cys Met
            20

<210> SEQ ID NO 119
<211> LENGTH: 20
<212> TYPE: PRT
<213> ORGANISM: Artificial
<220> FEATURE:
<223> OTHER INFORMATION: Peptide aptamer sequence

<400> SEQUENCE: 119

Gly Lys Leu Thr Asp Thr Arg Ile Ser Val Cys Cys Cys Ile Cys Val
1               5                   10                  15

Ser Val Leu Asp
            20

<210> SEQ ID NO 120
<211> LENGTH: 20
<212> TYPE: PRT
<213> ORGANISM: Artificial
<220> FEATURE:
<223> OTHER INFORMATION: Peptide aptamer sequence

<400> SEQUENCE: 120

His Lys Asp Arg Gly Tyr Ala Asn Leu Met Leu Cys Ser Leu Leu Ala
1               5                   10                  15
```

Cys Phe Glu Pro
          20

<210> SEQ ID NO 121
<211> LENGTH: 42
<212> TYPE: PRT
<213> ORGANISM: Artificial
<220> FEATURE:
<223> OTHER INFORMATION: Peptide aptamer sequence

<400> SEQUENCE: 121

Leu Ala Arg Gln Pro Gly Lys Phe Ile Glu Leu Pro Val Leu Ile Arg
1               5                   10                  15

Phe Ala Thr Ser Gly Pro Leu Leu Gln Ser Asn Ser Ser Gly His
            20                  25                  30

Trp Leu Ser Asp Glu His Trp Thr Arg Arg
        35                  40

<210> SEQ ID NO 122
<211> LENGTH: 20
<212> TYPE: PRT
<213> ORGANISM: Artificial
<220> FEATURE:
<223> OTHER INFORMATION: Peptide aptamer sequence

<400> SEQUENCE: 122

Gly Lys Leu Thr Asp Thr Thr Arg Ile Ser Val Cys Cys Ile Cys Val
1               5                   10                  15

Ser Val Leu Asp
          20

<210> SEQ ID NO 123
<211> LENGTH: 20
<212> TYPE: PRT
<213> ORGANISM: Artificial
<220> FEATURE:
<223> OTHER INFORMATION: Peptide aptamer sequence

<400> SEQUENCE: 123

Met Asp Arg Arg Glu Asp Leu Arg Ser Leu Leu Val Leu Thr Leu Ser
1               5                   10                  15

Asp Ala Arg Gly
          20

<210> SEQ ID NO 124
<211> LENGTH: 20
<212> TYPE: PRT
<213> ORGANISM: Artificial
<220> FEATURE:
<223> OTHER INFORMATION: Peptide aptamer sequence

<400> SEQUENCE: 124

His Lys Asp Arg Gly Tyr Ala Asn Leu Met Leu Cys Ser Leu Leu Ala
1               5                   10                  15

Cys Phe Glu Pro
          20

<210> SEQ ID NO 125
<211> LENGTH: 20
<212> TYPE: PRT
<213> ORGANISM: Artificial
<220> FEATURE:
<223> OTHER INFORMATION: Peptide aptamer sequence

```
<400> SEQUENCE: 125

Gly Met Leu Trp Thr Trp Leu Cys Asp Ser Pro Gln Ser Phe Val Ala
1               5                   10                  15

Pro Arg Gly Val
            20

<210> SEQ ID NO 126
<211> LENGTH: 19
<212> TYPE: PRT
<213> ORGANISM: Artificial
<220> FEATURE:
<223> OTHER INFORMATION: Peptide aptamer sequence

<400> SEQUENCE: 126

Pro Leu Leu Leu Leu Ala Ala Asp Ser Val Glu Leu Gln Arg Val Leu
1               5                   10                  15

Ala Arg Arg

<210> SEQ ID NO 127
<211> LENGTH: 20
<212> TYPE: PRT
<213> ORGANISM: Artificial
<220> FEATURE:
<223> OTHER INFORMATION: Peptide aptamer sequence

<400> SEQUENCE: 127

Ala Met Thr Tyr Arg Ala Ala Trp Ser Pro Pro Pro Trp Gly Val Leu
1               5                   10                  15

Gly Ile Trp His
            20

<210> SEQ ID NO 128
<211> LENGTH: 20
<212> TYPE: PRT
<213> ORGANISM: Artificial
<220> FEATURE:
<223> OTHER INFORMATION: Peptide aptamer sequence

<400> SEQUENCE: 128

Gly Met Leu Trp Thr Trp Leu Cys Asp Ser Pro Gln Ser Phe Val Ala
1               5                   10                  15

Pro Arg Gly Val
            20

<210> SEQ ID NO 129
<211> LENGTH: 20
<212> TYPE: PRT
<213> ORGANISM: Artificial
<220> FEATURE:
<223> OTHER INFORMATION: Peptide aptamer sequence

<400> SEQUENCE: 129

Ala Leu Lys Asp Glu Pro Phe Cys Asp Leu Pro Met Val Leu Val Ser
1               5                   10                  15

Trp Trp Arg Gly
            20

<210> SEQ ID NO 130
<211> LENGTH: 20
<212> TYPE: PRT
<213> ORGANISM: Artificial
<220> FEATURE:
<223> OTHER INFORMATION: Peptide aptamer sequence
```

```
<400> SEQUENCE: 130

Pro Val Cys Arg Val Gly Arg Gly Leu Leu Val Gln Ala Lys Leu Val
1               5                   10                  15

Arg Ala Gln Ser
            20

<210> SEQ ID NO 131
<211> LENGTH: 20
<212> TYPE: PRT
<213> ORGANISM: Artificial
<220> FEATURE:
<223> OTHER INFORMATION: Peptide aptamer sequence

<400> SEQUENCE: 131

Glu Val Val Glu Thr Ala Glu Val Tyr Trp Ser Cys Gly Asp Trp Ser
1               5                   10                  15

Cys Glu Gly Trp
            20

<210> SEQ ID NO 132
<211> LENGTH: 20
<212> TYPE: PRT
<213> ORGANISM: Artificial
<220> FEATURE:
<223> OTHER INFORMATION: Peptide aptamer sequence

<400> SEQUENCE: 132

Ser Phe Val Val Gln Ser Phe Leu Gly Gly Lys Ser Ile Phe Asn Gly
1               5                   10                  15

Pro Phe Ala Asp
            20

<210> SEQ ID NO 133
<211> LENGTH: 20
<212> TYPE: PRT
<213> ORGANISM: Artificial
<220> FEATURE:
<223> OTHER INFORMATION: Peptide aptamer sequence

<400> SEQUENCE: 133

Asp Leu Glu Trp Asp Gly Asn Ala Tyr Ser Gly Cys Cys His Cys Ala
1               5                   10                  15

Phe Ser Ile Arg
            20

<210> SEQ ID NO 134
<211> LENGTH: 20
<212> TYPE: PRT
<213> ORGANISM: Artificial
<220> FEATURE:
<223> OTHER INFORMATION: Peptide aptamer sequence

<400> SEQUENCE: 134

Leu Gly Ala Pro Leu Leu Arg Cys Met Val His His Ala Met Met Val
1               5                   10                  15

Gly Glu Gly Tyr
            20

<210> SEQ ID NO 135
<211> LENGTH: 24
<212> TYPE: PRT
<213> ORGANISM: Artificial
<220> FEATURE:
<223> OTHER INFORMATION: Peptide aptamer sequence
```

<400> SEQUENCE: 135

Gln Ser Val Arg Lys Met Pro Met Phe Trp Pro Leu Ala Gly Glu Val
1               5                   10                  15

Trp Cys Arg Pro Leu Gly Phe Arg
            20

<210> SEQ ID NO 136
<211> LENGTH: 20
<212> TYPE: PRT
<213> ORGANISM: Artificial
<220> FEATURE:
<223> OTHER INFORMATION: Peptide aptamer sequence

<400> SEQUENCE: 136

Phe Gly Val Ile Val Thr Asn Ala Ala Ser Glu Phe Thr Thr Arg Val
1               5                   10                  15

Asp Asp Ser Cys
            20

<210> SEQ ID NO 137
<211> LENGTH: 20
<212> TYPE: PRT
<213> ORGANISM: Artificial
<220> FEATURE:
<223> OTHER INFORMATION: Peptide aptamer sequence

<400> SEQUENCE: 137

Arg Pro Trp Ser Ser Asp Thr Ser Val Trp Trp Asp Gly Leu Phe Gly
1               5                   10                  15

Met Asn Tyr Ser
            20

<210> SEQ ID NO 138
<211> LENGTH: 20
<212> TYPE: PRT
<213> ORGANISM: Artificial
<220> FEATURE:
<223> OTHER INFORMATION: Peptide aptamer sequence

<400> SEQUENCE: 138

Pro Asn Cys Glu Ile Cys Tyr Val Ala Arg Arg Leu Val Leu Ser Met
1               5                   10                  15

Glu Ala Cys Ser
            20

<210> SEQ ID NO 139
<211> LENGTH: 20
<212> TYPE: PRT
<213> ORGANISM: Artificial
<220> FEATURE:
<223> OTHER INFORMATION: Peptide aptamer sequence

<400> SEQUENCE: 139

Pro Asn Cys Glu Ile Cys Tyr Val Ala Arg Arg Leu Val Leu Ser Met
1               5                   10                  15

Glu Ala Cys Ser
            20

<210> SEQ ID NO 140
<211> LENGTH: 20
<212> TYPE: PRT
<213> ORGANISM: Artificial
<220> FEATURE:

```
<223> OTHER INFORMATION: Peptide aptamer sequence

<400> SEQUENCE: 140

Arg Leu Thr Val Leu Glu Ala Ala Val Val Leu Trp Gly Trp Ser Leu
1               5                   10                  15

Phe Gln Val Pro
            20

<210> SEQ ID NO 141
<211> LENGTH: 20
<212> TYPE: PRT
<213> ORGANISM: Artificial
<220> FEATURE:
<223> OTHER INFORMATION: Peptide aptamer sequence

<400> SEQUENCE: 141

Glu Gly Leu Pro Ile Asp Leu Leu Thr Asn Trp His Leu Thr Cys Trp
1               5                   10                  15

Ile Ala Leu Gly
            20

<210> SEQ ID NO 142
<211> LENGTH: 42
<212> TYPE: PRT
<213> ORGANISM: Artificial
<220> FEATURE:
<223> OTHER INFORMATION: Peptide aptamer sequence

<400> SEQUENCE: 142

Ser Phe Met Met Arg Leu Leu Arg Thr Gly Glu Met Gln Phe Gln Ala
1               5                   10                  15

Asp Cys Val Gly Gly Pro Ile Pro Leu Lys Ser Pro Arg Ala Leu Ser
            20                  25                  30

Leu Tyr Asn Trp Gly Leu Leu Leu Trp Val
        35                  40

<210> SEQ ID NO 143
<211> LENGTH: 20
<212> TYPE: PRT
<213> ORGANISM: Artificial
<220> FEATURE:
<223> OTHER INFORMATION: Peptide aptamer sequence

<400> SEQUENCE: 143

Gly Val Asn Leu Leu Gln Arg Cys Trp Gly Gly Pro Val His Ile Phe
1               5                   10                  15

Ser Tyr Leu Met
            20

<210> SEQ ID NO 144
<211> LENGTH: 20
<212> TYPE: PRT
<213> ORGANISM: Artificial
<220> FEATURE:
<223> OTHER INFORMATION: Peptide aptamer sequence

<400> SEQUENCE: 144

Cys Ala Met Cys Leu Asp Val Phe Gly Trp Ser Ala Ser His Trp Gly
1               5                   10                  15

Gly Phe Thr Val
            20

<210> SEQ ID NO 145
```

<211> LENGTH: 20
<212> TYPE: PRT
<213> ORGANISM: Artificial
<220> FEATURE:
<223> OTHER INFORMATION: Peptide aptamer sequence

<400> SEQUENCE: 145

Val Asp Ser Ile Asp Lys Gly Glu Ala Leu Val Ser Leu Trp Gly Trp
1               5                   10                  15

His Val Gln Ile
            20

<210> SEQ ID NO 146
<211> LENGTH: 20
<212> TYPE: PRT
<213> ORGANISM: Artificial
<220> FEATURE:
<223> OTHER INFORMATION: Peptide aptamer sequence

<400> SEQUENCE: 146

Pro Pro Trp Thr Lys Arg Pro Leu Thr Ser Gly Gly Val Arg Gly Glu
1               5                   10                  15

Leu Trp Val Trp
            20

<210> SEQ ID NO 147
<211> LENGTH: 20
<212> TYPE: PRT
<213> ORGANISM: Artificial
<220> FEATURE:
<223> OTHER INFORMATION: Peptide aptamer sequence

<400> SEQUENCE: 147

Cys Leu Met His Met Arg Phe Pro Leu Gly Gly Thr Trp Arg Met Asn
1               5                   10                  15

Leu Arg Ala Glu
            20

<210> SEQ ID NO 148
<211> LENGTH: 20
<212> TYPE: PRT
<213> ORGANISM: Artificial
<220> FEATURE:
<223> OTHER INFORMATION: Peptide aptamer sequence

<400> SEQUENCE: 148

Leu Val Arg Trp Ser Tyr Thr Cys Ser Val Leu Val Gly Leu Arg Asp
1               5                   10                  15

Ser Leu Asp Ser
            20

<210> SEQ ID NO 149
<211> LENGTH: 20
<212> TYPE: PRT
<213> ORGANISM: Artificial
<220> FEATURE:
<223> OTHER INFORMATION: Peptide aptamer sequence

<400> SEQUENCE: 149

Leu Val Thr Ala Leu Ile Met Ser Glu Ser Ile Val Arg Met Asn Pro
1               5                   10                  15

Met Tyr Leu Thr
            20

```
<210> SEQ ID NO 150
<211> LENGTH: 20
<212> TYPE: PRT
<213> ORGANISM: Artificial
<220> FEATURE:
<223> OTHER INFORMATION: Peptide aptamer sequence

<400> SEQUENCE: 150

Glu Val Glu Arg Ser Arg Met Leu Phe Asn Tyr Gly Gly Met Val Ala
1               5                   10                  15

Ser Arg Val Ala
            20

<210> SEQ ID NO 151
<211> LENGTH: 20
<212> TYPE: PRT
<213> ORGANISM: Artificial
<220> FEATURE:
<223> OTHER INFORMATION: Peptide aptamer sequence

<400> SEQUENCE: 151

Pro Trp Leu Ser Val Asp Val Thr Ala Leu Ile Val Asp Phe Leu Gln
1               5                   10                  15

Asp Phe Ser Ala
            20

<210> SEQ ID NO 152
<211> LENGTH: 20
<212> TYPE: PRT
<213> ORGANISM: Artificial
<220> FEATURE:
<223> OTHER INFORMATION: Peptide aptamer sequence

<400> SEQUENCE: 152

Ile Ser Ser Tyr Leu Trp Trp Ser Glu Tyr Cys Arg Pro Gly Ser Ala
1               5                   10                  15

Met Gly Asp Val
            20

<210> SEQ ID NO 153
<211> LENGTH: 20
<212> TYPE: PRT
<213> ORGANISM: Artificial
<220> FEATURE:
<223> OTHER INFORMATION: Peptide aptamer sequence

<400> SEQUENCE: 153

Val Ile Val Asp Phe Leu Ser Thr Gly Val Ser Thr Gly Glu Val Arg
1               5                   10                  15

Gly Gly Ile Val
            20

<210> SEQ ID NO 154
<211> LENGTH: 20
<212> TYPE: PRT
<213> ORGANISM: Artificial
<220> FEATURE:
<223> OTHER INFORMATION: Peptide aptamer sequence

<400> SEQUENCE: 154

Phe Asn Ala Arg Ala Leu Ala Cys Lys Cys Asp Arg Gly Ile Leu Ile
1               5                   10                  15

Leu Ser Gln Pro
            20
```

<210> SEQ ID NO 155
<211> LENGTH: 20
<212> TYPE: PRT
<213> ORGANISM: Artificial
<220> FEATURE:
<223> OTHER INFORMATION: Peptide aptamer sequence

<400> SEQUENCE: 155

Glu Gly Gly Glu Asp Ser Ala Trp Asp Trp Gly Ser Ser Gly Gly Ile
1               5                   10                  15

Trp Cys Trp Phe
            20

<210> SEQ ID NO 156
<211> LENGTH: 20
<212> TYPE: PRT
<213> ORGANISM: Artificial
<220> FEATURE:
<223> OTHER INFORMATION: Peptide aptamer sequence

<400> SEQUENCE: 156

Leu Leu Tyr Pro Ser Leu Thr Leu Thr Leu Trp Arg Trp Leu Phe Ala
1               5                   10                  15

Asp Glu Gly Cys
            20

<210> SEQ ID NO 157
<211> LENGTH: 20
<212> TYPE: PRT
<213> ORGANISM: Artificial
<220> FEATURE:
<223> OTHER INFORMATION: Peptide aptamer sequence

<400> SEQUENCE: 157

Cys Asp Val Met Glu Trp Arg Met Met Gly Leu Gly Leu Ser Lys Trp
1               5                   10                  15

Leu Arg Gly Arg
            20

<210> SEQ ID NO 158
<211> LENGTH: 20
<212> TYPE: PRT
<213> ORGANISM: Artificial
<220> FEATURE:
<223> OTHER INFORMATION: Peptide aptamer sequence

<400> SEQUENCE: 158

Asp Leu Glu Trp Asp Gly Asn Ala Tyr Ser Gly Cys Cys His Cys Ala
1               5                   10                  15

Gly Ser Ile Arg
            20

<210> SEQ ID NO 159
<211> LENGTH: 20
<212> TYPE: PRT
<213> ORGANISM: Artificial
<220> FEATURE:
<223> OTHER INFORMATION: Peptide aptamer sequence

<400> SEQUENCE: 159

Ile Tyr Asp Tyr Thr Trp Ala Glu Glu Gln Gly Tyr Val Trp Arg Pro
1               5                   10                  15

Ala Gly Gly Ala
            20

```
<210> SEQ ID NO 160
<211> LENGTH: 20
<212> TYPE: PRT
<213> ORGANISM: Artificial
<220> FEATURE:
<223> OTHER INFORMATION: Peptide aptamer sequence

<400> SEQUENCE: 160

Gln Met Asn Ala Ala Pro Pro Ala Arg Ser Cys Ala Asp Thr Trp Ser
1               5                   10                  15

Leu Leu Leu Phe
            20

<210> SEQ ID NO 161
<211> LENGTH: 20
<212> TYPE: PRT
<213> ORGANISM: Artificial
<220> FEATURE:
<223> OTHER INFORMATION: Peptide aptamer sequence

<400> SEQUENCE: 161

Arg Val Trp Thr Phe Phe Val Arg Glu Ala Ala Leu Glu Leu Pro Ser
1               5                   10                  15

Arg Asp Thr Leu
            20

<210> SEQ ID NO 162
<211> LENGTH: 20
<212> TYPE: PRT
<213> ORGANISM: Artificial
<220> FEATURE:
<223> OTHER INFORMATION: Peptide aptamer sequence

<400> SEQUENCE: 162

Val Tyr Tyr His Lys Glu Cys Ala Leu Asp Ser Tyr Val Arg Thr Cys
1               5                   10                  15

Trp Val Ser Gly
            20

<210> SEQ ID NO 163
<211> LENGTH: 20
<212> TYPE: PRT
<213> ORGANISM: Artificial
<220> FEATURE:
<223> OTHER INFORMATION: Peptide aptamer sequence

<400> SEQUENCE: 163

Phe Asn Ala Arg Ala Leu Ala Cys Lys Cys Asp Arg Arg Ile Leu Ile
1               5                   10                  15

Leu Ser Gln Pro
            20

<210> SEQ ID NO 164
<211> LENGTH: 20
<212> TYPE: PRT
<213> ORGANISM: Artificial
<220> FEATURE:
<223> OTHER INFORMATION: Peptide aptamer sequence

<400> SEQUENCE: 164

Thr Leu His Thr Asn Arg Phe Cys Phe Arg Trp Val Pro Ala Leu Asp
1               5                   10                  15

Ser Val Thr Thr
```

```
                        20

<210> SEQ ID NO 165
<211> LENGTH: 20
<212> TYPE: PRT
<213> ORGANISM: Artificial
<220> FEATURE:
<223> OTHER INFORMATION: Peptide aptamer sequence

<400> SEQUENCE: 165

Leu Asn Pro Trp Glu Gly Glu Trp Thr Arg Trp Asp Val Phe Arg Val
1               5                   10                  15

Leu Gly Glu Phe
            20

<210> SEQ ID NO 166
<211> LENGTH: 20
<212> TYPE: PRT
<213> ORGANISM: Artificial
<220> FEATURE:
<223> OTHER INFORMATION: Peptide aptamer sequence

<400> SEQUENCE: 166

Gln Met Phe Trp Phe Thr Asp Ser Glu Gly Lys Pro Gly Phe Cys Thr
1               5                   10                  15

Phe Tyr Gly Phe
            20

<210> SEQ ID NO 167
<211> LENGTH: 20
<212> TYPE: PRT
<213> ORGANISM: Artificial
<220> FEATURE:
<223> OTHER INFORMATION: Peptide aptamer sequence

<400> SEQUENCE: 167

Pro Ser Ala Tyr Glu Ala Val Glu Thr Leu Asp Met Ser Glu Val Lys
1               5                   10                  15

Gly Leu Gly Gln
            20

<210> SEQ ID NO 168
<211> LENGTH: 20
<212> TYPE: PRT
<213> ORGANISM: Artificial
<220> FEATURE:
<223> OTHER INFORMATION: Peptide aptamer sequence

<400> SEQUENCE: 168

Leu Ala Arg Cys Leu Cys Glu Ile Val Gly Ser Cys Ile Ser Tyr Ser
1               5                   10                  15

Asn Leu Pro Ile
            20

<210> SEQ ID NO 169
<211> LENGTH: 20
<212> TYPE: PRT
<213> ORGANISM: Artificial
<220> FEATURE:
<223> OTHER INFORMATION: Peptide aptamer sequence

<400> SEQUENCE: 169

Ser Gly Tyr Pro Lys Met Val Trp Gly Glu Gly Pro Met Leu Leu Asp
1               5                   10                  15
```

```
Trp Lys Phe Val
            20

<210> SEQ ID NO 170
<211> LENGTH: 20
<212> TYPE: PRT
<213> ORGANISM: Artificial
<220> FEATURE:
<223> OTHER INFORMATION: Peptide aptamer sequence

<400> SEQUENCE: 170

Ser Phe Ala Thr Ala Asn Ser Glu Gln Val Leu Arg Asp Met Leu Leu
1               5                   10                  15

Leu Ala Ser His
            20

<210> SEQ ID NO 171
<211> LENGTH: 20
<212> TYPE: PRT
<213> ORGANISM: Artificial
<220> FEATURE:
<223> OTHER INFORMATION: Peptide aptamer sequence

<400> SEQUENCE: 171

Val Gly Pro Leu Ile Val Gly Pro Pro Gly Met Glu Met Thr Ala Asn
1               5                   10                  15

Ser Trp Ser Cys
            20

<210> SEQ ID NO 172
<211> LENGTH: 20
<212> TYPE: PRT
<213> ORGANISM: Artificial
<220> FEATURE:
<223> OTHER INFORMATION: Peptide aptamer sequence

<400> SEQUENCE: 172

Cys Glu Asp Met Arg Glu Ala Lys Val Cys Arg Thr Leu Leu Ala His
1               5                   10                  15

Ser Phe Leu Pro
            20

<210> SEQ ID NO 173
<211> LENGTH: 20
<212> TYPE: PRT
<213> ORGANISM: Artificial
<220> FEATURE:
<223> OTHER INFORMATION: Peptide aptamer sequence

<400> SEQUENCE: 173

Arg Pro Trp Ser Ser Asp Thr Ser Val Trp Trp Asp Gly Leu Phe Gly
1               5                   10                  15

Met Asn Tyr Ser
            20

<210> SEQ ID NO 174
<211> LENGTH: 20
<212> TYPE: PRT
<213> ORGANISM: Artificial
<220> FEATURE:
<223> OTHER INFORMATION: Peptide aptamer sequence

<400> SEQUENCE: 174

Asp Leu Arg Leu Pro Val Tyr Ser Glu Trp Val Arg Val Tyr Ser Ser
1               5                   10                  15
```

Asp Ala Trp Met
        20

<210> SEQ ID NO 175
<211> LENGTH: 41
<212> TYPE: PRT
<213> ORGANISM: Artificial
<220> FEATURE:
<223> OTHER INFORMATION: Peptide aptamer sequence

<400> SEQUENCE: 175

Gly Arg Phe Gly Gln Gly Gln Cys Tyr Gln Val Ala Asp Ser Thr Tyr
1               5                   10                  15

Trp Thr Phe Gly Pro Gly Gly Pro Arg Lys Cys Glu Arg Glu Pro Ala
            20                  25                  30

Gly Trp Ser Asp Thr Gly Trp Val Cys
        35                  40

<210> SEQ ID NO 176
<211> LENGTH: 20
<212> TYPE: PRT
<213> ORGANISM: Artificial
<220> FEATURE:
<223> OTHER INFORMATION: Peptide aptamer sequence

<400> SEQUENCE: 176

Trp Cys Ser Met Cys Ser Val Leu Arg Ala Phe Asn Cys Pro Tyr Phe
1               5                   10                  15

Cys Pro Trp Leu
        20

<210> SEQ ID NO 177
<211> LENGTH: 20
<212> TYPE: PRT
<213> ORGANISM: Artificial
<220> FEATURE:
<223> OTHER INFORMATION: Peptide aptamer sequence

<400> SEQUENCE: 177

Pro Trp Ile Phe Asp Arg Ser Val Val Cys Glu Glu Arg Glu Ala Pro
1               5                   10                  15

Arg Arg His Leu
        20

<210> SEQ ID NO 178
<211> LENGTH: 20
<212> TYPE: PRT
<213> ORGANISM: Artificial
<220> FEATURE:
<223> OTHER INFORMATION: Peptide aptamer sequence

<400> SEQUENCE: 178

Thr Ser Trp Arg His Arg Met Pro Thr Gly Thr Asp Arg Cys Cys Phe
1               5                   10                  15

Leu Val Gln Leu
        20

<210> SEQ ID NO 179
<211> LENGTH: 20
<212> TYPE: PRT
<213> ORGANISM: Artificial
<220> FEATURE:
<223> OTHER INFORMATION: Peptide aptamer sequence -continued

<400> SEQUENCE: 179

Arg Pro Trp Ser Ser Asp Thr Ser Val Trp Trp Asp Gly Leu Phe Gly
1               5                   10                  15

Met Asn Tyr Ser
            20

<210> SEQ ID NO 180
<211> LENGTH: 20
<212> TYPE: PRT
<213> ORGANISM: Artificial
<220> FEATURE:
<223> OTHER INFORMATION: Peptide aptamer sequence

<400> SEQUENCE: 180

Arg Pro Trp Ser Ser Asp Thr Ser Val Trp Trp Asp Gly Leu Phe Gly
1               5                   10                  15

Met Asn Tyr Ser
            20

<210> SEQ ID NO 181
<211> LENGTH: 20
<212> TYPE: PRT
<213> ORGANISM: Artificial
<220> FEATURE:
<223> OTHER INFORMATION: Peptide aptamer sequence

<400> SEQUENCE: 181

Leu Val Thr Ala Leu Ile Met Ser Glu Ser Ile Val Arg Met Asn Pro
1               5                   10                  15

Met Tyr Leu Thr
            20

<210> SEQ ID NO 182
<211> LENGTH: 20
<212> TYPE: PRT
<213> ORGANISM: Artificial
<220> FEATURE:
<223> OTHER INFORMATION: Peptide aptamer sequence

<400> SEQUENCE: 182

Leu Leu Ala Cys Ser Val Tyr Trp Leu Trp Gln Arg Pro Cys Asp Gly
1               5                   10                  15

Cys Leu Phe Met
            20

<210> SEQ ID NO 183
<211> LENGTH: 20
<212> TYPE: PRT
<213> ORGANISM: Artificial
<220> FEATURE:
<223> OTHER INFORMATION: Peptide aptamer sequence

<400> SEQUENCE: 183

Gly Val Asn Asn Gly Gly Thr Asn Asp Pro Glu Gly Val Ser Glu Ala
1               5                   10                  15

Ser Trp Ile Pro
            20

<210> SEQ ID NO 184
<211> LENGTH: 20
<212> TYPE: PRT
<213> ORGANISM: Artificial
<220> FEATURE:
<223> OTHER INFORMATION: Peptide aptamer sequence -continued

<400> SEQUENCE: 184

Leu Leu Ala Cys Ser Val Tyr Trp Leu Trp Gln Arg Pro Cys Asp Gly
1               5                   10                  15

Cys Leu Phe Met
            20

<210> SEQ ID NO 185
<211> LENGTH: 20
<212> TYPE: PRT
<213> ORGANISM: Artificial
<220> FEATURE:
<223> OTHER INFORMATION: Peptide aptamer sequence

<400> SEQUENCE: 185

Gly Ile Val Ser Lys Gln Gly Ala Asp Glu Gly Met Leu Glu Ile Phe
1               5                   10                  15

Ala Ser Ser Trp
            20

<210> SEQ ID NO 186
<211> LENGTH: 20
<212> TYPE: PRT
<213> ORGANISM: Artificial
<220> FEATURE:
<223> OTHER INFORMATION: Peptide aptamer sequence

<400> SEQUENCE: 186

Thr Ile Asp Gln Arg Met Val Ser Leu Gly Ala Ile Trp Trp Ser Tyr
1               5                   10                  15

Pro Arg Cys Trp
            20

<210> SEQ ID NO 187
<211> LENGTH: 20
<212> TYPE: PRT
<213> ORGANISM: Artificial
<220> FEATURE:
<223> OTHER INFORMATION: Peptide aptamer sequence

<400> SEQUENCE: 187

Pro Pro Trp Thr Lys Arg Pro Leu Thr Ser Gly Gly Val Arg Gly Glu
1               5                   10                  15

Leu Trp Val Trp
            20

<210> SEQ ID NO 188
<211> LENGTH: 20
<212> TYPE: PRT
<213> ORGANISM: Artificial
<220> FEATURE:
<223> OTHER INFORMATION: Peptide aptamer sequence

<400> SEQUENCE: 188

Arg Val Asp Ser Leu Gly Ile Lys Leu Asp Lys Ser Thr Leu Val Thr
1               5                   10                  15

Val His Val Val
            20

<210> SEQ ID NO 189
<211> LENGTH: 20
<212> TYPE: PRT
<213> ORGANISM: Artificial
<220> FEATURE:

<223> OTHER INFORMATION: Peptide aptamer sequence

<400> SEQUENCE: 189

Thr Glu Ala Cys Gln Val Val Leu Leu Gly Lys Arg Ser Leu Leu Pro
1               5                   10                  15
Val Val Ala Gly
            20

<210> SEQ ID NO 190
<211> LENGTH: 20
<212> TYPE: PRT
<213> ORGANISM: Artificial
<220> FEATURE:
<223> OTHER INFORMATION: Peptide aptamer sequence

<400> SEQUENCE: 190

Ala Gln Arg Ser Cys Trp Glu Arg Leu Trp Thr Gly Gln Trp Arg Arg
1               5                   10                  15
Leu Pro Leu Met
            20

<210> SEQ ID NO 191
<211> LENGTH: 20
<212> TYPE: PRT
<213> ORGANISM: Artificial
<220> FEATURE:
<223> OTHER INFORMATION: Peptide aptamer sequence

<400> SEQUENCE: 191

Ala Gln Arg Ser Cys Trp Glu Arg Leu Trp Thr Gly Gln Trp Arg Arg
1               5                   10                  15
Ser Ala Ser Asp
            20

<210> SEQ ID NO 192
<211> LENGTH: 20
<212> TYPE: PRT
<213> ORGANISM: Artificial
<220> FEATURE:
<223> OTHER INFORMATION: Peptide aptamer sequence

<400> SEQUENCE: 192

Val Ser Trp Ser Ala Ala Gly Arg Gly Tyr Val Phe Met Tyr Arg Trp
1               5                   10                  15
Ser Pro Arg Cys
            20

<210> SEQ ID NO 193
<211> LENGTH: 20
<212> TYPE: PRT
<213> ORGANISM: Artificial
<220> FEATURE:
<223> OTHER INFORMATION: Peptide aptamer sequence

<400> SEQUENCE: 193

Phe Gly Val Ile Val Thr Asn Ala Ala Ser Glu Phe Thr Thr Arg Gly
1               5                   10                  15
Tyr Asp Ser Cys
            20

<210> SEQ ID NO 194
<211> LENGTH: 20
<212> TYPE: PRT
<213> ORGANISM: Artificial

<220> FEATURE:
<223> OTHER INFORMATION: Peptide aptamer sequence

<400> SEQUENCE: 194

Ser Phe Ser Ser Leu Phe Leu Ala Trp Leu Met Gln Thr Gly Gln Glu
1               5                   10                  15

Ala Gly Thr Val
            20

<210> SEQ ID NO 195
<211> LENGTH: 20
<212> TYPE: PRT
<213> ORGANISM: Artificial
<220> FEATURE:
<223> OTHER INFORMATION: Peptide aptamer sequence

<400> SEQUENCE: 195

Ser Arg Ser Asp Leu Trp Val Ser Trp Cys Arg Asn Leu Leu Asp Gly
1               5                   10                  15

Gln Ser Trp Ser
            20

<210> SEQ ID NO 196
<211> LENGTH: 20
<212> TYPE: PRT
<213> ORGANISM: Artificial
<220> FEATURE:
<223> OTHER INFORMATION: Peptide aptamer sequence

<400> SEQUENCE: 196

His Pro Tyr Leu Ile Thr Asp Ile Ile Ser Met Tyr Arg Ser Pro Trp
1               5                   10                  15

Ser Val Pro Ala
            20

<210> SEQ ID NO 197
<211> LENGTH: 20
<212> TYPE: PRT
<213> ORGANISM: Artificial
<220> FEATURE:
<223> OTHER INFORMATION: Peptide aptamer sequence

<400> SEQUENCE: 197

Arg Asp Ala Leu Thr Asn Ile Gly Arg Ser Ile Cys Ala Leu Leu Leu
1               5                   10                  15

Val Leu Cys Lys
            20

<210> SEQ ID NO 198
<211> LENGTH: 20
<212> TYPE: PRT
<213> ORGANISM: Artificial
<220> FEATURE:
<223> OTHER INFORMATION: Peptide aptamer sequence

<400> SEQUENCE: 198

Trp Gly Tyr Phe Gly Ser Phe Val Gly Gly Val Phe Asp Val Trp Phe
1               5                   10                  15

Ser Gly Val Ala
            20

<210> SEQ ID NO 199
<211> LENGTH: 20
<212> TYPE: PRT

<213> ORGANISM: Artificial
<220> FEATURE:
<223> OTHER INFORMATION: Peptide aptamer sequence

<400> SEQUENCE: 199

Ser Arg Ser Asp Leu Trp Val Ser Trp Cys Arg Asn Leu Leu Asp Gly
1               5                   10                  15

Gln Ser Trp Ser
            20

<210> SEQ ID NO 200
<211> LENGTH: 20
<212> TYPE: PRT
<213> ORGANISM: Artificial
<220> FEATURE:
<223> OTHER INFORMATION: Peptide aptamer sequence

<400> SEQUENCE: 200

Arg Asn Gly Arg Asn Ile Cys Val Leu Ser Val Cys Ser Arg Phe Ser
1               5                   10                  15

His Phe Asn Pro
            20

<210> SEQ ID NO 201
<211> LENGTH: 20
<212> TYPE: PRT
<213> ORGANISM: Artificial
<220> FEATURE:
<223> OTHER INFORMATION: Peptide aptamer sequence

<400> SEQUENCE: 201

Gly Gly Ser Asp Glu Arg Tyr Phe Trp Tyr Gln Ser Phe Ser Cys
1               5                   10                  15

Ala Tyr Glu Trp
            20

<210> SEQ ID NO 202
<211> LENGTH: 20
<212> TYPE: PRT
<213> ORGANISM: Artificial
<220> FEATURE:
<223> OTHER INFORMATION: Peptide aptamer sequence

<400> SEQUENCE: 202

Gly Val Leu Phe Thr Phe Lys Lys Tyr Pro Gln Gly Leu Ser Cys Thr
1               5                   10                  15

Thr Ser Tyr Gly
            20

<210> SEQ ID NO 203
<211> LENGTH: 20
<212> TYPE: PRT
<213> ORGANISM: Artificial
<220> FEATURE:
<223> OTHER INFORMATION: Peptide aptamer sequence

<400> SEQUENCE: 203

Leu Leu Ala Cys Ser Val Tyr Trp Leu Trp Gln Arg Pro Cys Asp Gly
1               5                   10                  15

Cys Leu Phe Met
            20

<210> SEQ ID NO 204
<211> LENGTH: 20

```
<212> TYPE: PRT
<213> ORGANISM: Artificial
<220> FEATURE:
<223> OTHER INFORMATION: Peptide aptamer sequence

<400> SEQUENCE: 204

Val Val Gln Asn Val Arg Gly Trp Leu Val Tyr Cys Cys Ala Asp Phe
1               5                   10                  15

His Thr Tyr Val
            20

<210> SEQ ID NO 205
<211> LENGTH: 20
<212> TYPE: PRT
<213> ORGANISM: Artificial
<220> FEATURE:
<223> OTHER INFORMATION: Peptide aptamer sequence

<400> SEQUENCE: 205

Leu Arg Gly Val Ser Pro Trp Leu Gln Ser Phe Val Ser Ile Ala Val
1               5                   10                  15

Gln Ser Cys Lys
            20

<210> SEQ ID NO 206
<211> LENGTH: 20
<212> TYPE: PRT
<213> ORGANISM: Artificial
<220> FEATURE:
<223> OTHER INFORMATION: Peptide aptamer sequence

<400> SEQUENCE: 206

Thr Gly Ser Gly Leu Thr Pro Cys Leu His Cys Arg Val Gln Phe Gln
1               5                   10                  15

Arg Ser Tyr Leu
            20

<210> SEQ ID NO 207
<211> LENGTH: 20
<212> TYPE: PRT
<213> ORGANISM: Artificial
<220> FEATURE:
<223> OTHER INFORMATION: Peptide aptamer sequence

<400> SEQUENCE: 207

Thr Arg Met His Ser Leu Cys Ser Gly Phe Cys Val Ile Cys Met Gly
1               5                   10                  15

Gly Pro Arg Val
            20

<210> SEQ ID NO 208
<211> LENGTH: 20
<212> TYPE: PRT
<213> ORGANISM: Artificial
<220> FEATURE:
<223> OTHER INFORMATION: Peptide aptamer sequence

<400> SEQUENCE: 208

Arg Asn Gly Arg Asn Ile Cys Val Leu Ser Val Cys Ser Arg Phe Ser
1               5                   10                  15

His Phe Asn Pro
            20

<210> SEQ ID NO 209
```

```
<211> LENGTH: 20
<212> TYPE: PRT
<213> ORGANISM: Artificial
<220> FEATURE:
<223> OTHER INFORMATION: Peptide aptamer sequence

<400> SEQUENCE: 209

Met Leu Gly Ile Trp Arg Val Leu His Glu Met Val Val Pro Leu Lys
1               5                   10                  15

Leu Gly Val Asp
            20

<210> SEQ ID NO 210
<211> LENGTH: 20
<212> TYPE: PRT
<213> ORGANISM: Artificial
<220> FEATURE:
<223> OTHER INFORMATION: Peptide aptamer sequence

<400> SEQUENCE: 210

Cys Pro Asp Cys Pro Leu Ser Ser Val Leu Arg Thr Ala Thr Thr Ala
1               5                   10                  15

Phe Phe Gly Gly
            20

<210> SEQ ID NO 211
<211> LENGTH: 20
<212> TYPE: PRT
<213> ORGANISM: Artificial
<220> FEATURE:
<223> OTHER INFORMATION: Peptide aptamer sequence

<400> SEQUENCE: 211

Arg Gly Arg Met Glu Ala Asp Lys Ser Phe Asp Ser Thr Cys Leu Arg
1               5                   10                  15

Cys Gly Cys Ser
            20

<210> SEQ ID NO 212
<211> LENGTH: 22
<212> TYPE: DNA
<213> ORGANISM: Artificial
<220> FEATURE:
<223> OTHER INFORMATION: Replication oligonucleotide

<400> SEQUENCE: 212
gatgtttggc aacctcctct ag                                          22

<210> SEQ ID NO 213
<211> LENGTH: 24
<212> TYPE: DNA
<213> ORGANISM: Artificial
<220> FEATURE:
<223> OTHER INFORMATION: Replication oligonucleotide

<400> SEQUENCE: 213
ggtcgttctt taccgttgca gtac                                        24

<210> SEQ ID NO 214
<211> LENGTH: 31
<212> TYPE: DNA
<213> ORGANISM: Artificial
<220> FEATURE:
<223> OTHER INFORMATION: Cloning oligonucloetide

<400> SEQUENCE: 214
```

-continued tcaatgagct cggtcctacc cttatgatgt g　　　　　　　　　　　　　31

<210> SEQ ID NO 215
<211> LENGTH: 20
<212> TYPE: DNA
<213> ORGANISM: Artificial
<220> FEATURE:
<223> OTHER INFORMATION: Sequencing oligonucloetide

<400> SEQUENCE: 215
ttcacctgac tgacgacagt　　　　　　　　　　　　　　　　20

<210> SEQ ID NO 216
<211> LENGTH: 29
<212> TYPE: DNA
<213> ORGANISM: Artificial
<220> FEATURE:
<223> OTHER INFORMATION: Cloning oligonucleotide

<400> SEQUENCE: 216
atggatccag gcctctggcg aagaagtcc　　　　　　　　　　　　29

<210> SEQ ID NO 217
<211> LENGTH: 24
<212> TYPE: DNA
<213> ORGANISM: Artificial
<220> FEATURE:
<223> OTHER INFORMATION: Sequencing oligonucloetide

<400> SEQUENCE: 217
tcatttcatt tggagaggac acgc　　　　　　　　　　　　　24

<210> SEQ ID NO 218
<211> LENGTH: 24
<212> TYPE: DNA
<213> ORGANISM: Artificial
<220> FEATURE:
<223> OTHER INFORMATION: Sequencing oligonucloetide

<400> SEQUENCE: 218
ccaatgccat aatactcgaa ctca　　　　　　　　　　　　　24

<210> SEQ ID NO 219
<211> LENGTH: 27
<212> TYPE: DNA
<213> ORGANISM: Artificial
<220> FEATURE:
<223> OTHER INFORMATION: Cloning oligoncleotide

<400> SEQUENCE: 219
tacagcggtc cgtgcaaaat gatcgcc　　　　　　　　　　　　27

<210> SEQ ID NO 220
<211> LENGTH: 22
<212> TYPE: DNA
<213> ORGANISM: Artificial
<220> FEATURE:
<223> OTHER INFORMATION: Cloning oligoncleotide

<400> SEQUENCE: 220
cggaccgcac cactctgccc ag　　　　　　　　　　　　　　22

<210> SEQ ID NO 221
<211> LENGTH: 28
<212> TYPE: DNA

```
<213> ORGANISM: Artificial
<220> FEATURE:
<223> OTHER INFORMATION: Cloning oligoncleotide

<400> SEQUENCE: 221
gatctgaatt cgcgatctag agagctcg                                          28

<210> SEQ ID NO 222
<211> LENGTH: 28
<212> TYPE: DNA
<213> ORGANISM: Artificial
<220> FEATURE:
<223> OTHER INFORMATION: Cloning oligoncleotide

<400> SEQUENCE: 222
gatccgagct ctctagatcg cgaattca                                          28

<210> SEQ ID NO 223
<211> LENGTH: 38
<212> TYPE: DNA
<213> ORGANISM: Artificial
<220> FEATURE:
<223> OTHER INFORMATION: Cloning oligoncleotide

<400> SEQUENCE: 223
aattcggacg tcgctccgtc gatactatgt tatacgcc                               38

<210> SEQ ID NO 224
<211> LENGTH: 36
<212> TYPE: DNA
<213> ORGANISM: Artificial
<220> FEATURE:
<223> OTHER INFORMATION: Cloning oligoncleotide

<400> SEQUENCE: 224
atgacccggg gacgctcagt ggaacgaaaa ctcacg                                 36

<210> SEQ ID NO 225
<211> LENGTH: 24
<212> TYPE: DNA
<213> ORGANISM: Artificial
<220> FEATURE:
<223> OTHER INFORMATION: Replication oligonucleotide

<400> SEQUENCE: 225
ggcgatagaa ggcgatgcgc tgcg                                              24

<210> SEQ ID NO 226
<211> LENGTH: 23
<212> TYPE: DNA
<213> ORGANISM: Artificial
<220> FEATURE:
<223> OTHER INFORMATION: Replication oligonucleotide

<400> SEQUENCE: 226
tgcacgcagg ttctccggcc gct                                               23

<210> SEQ ID NO 227
<211> LENGTH: 34
<212> TYPE: DNA
<213> ORGANISM: Artificial
<220> FEATURE:
<223> OTHER INFORMATION: Cloning oligoncleotide

<400> SEQUENCE: 227
aagagctcag tactcctacc cttatgatgt gcca                                   34
```

<210> SEQ ID NO 228
<211> LENGTH: 26
<212> TYPE: DNA
<213> ORGANISM: Artificial
<220> FEATURE:
<223> OTHER INFORMATION: Cloning oligoncleotide

<400> SEQUENCE: 228
ttgagctcct ctggcgaaga agtcca                                      26

<210> SEQ ID NO 229
<211> LENGTH: 60
<212> TYPE: DNA
<213> ORGANISM: Artificial
<220> FEATURE:
<223> OTHER INFORMATION: Cloning oligoncleotide

<400> SEQUENCE: 229
gtccggagct ccctatacta ggttattgga aaattaaggg ccttgtgcaa cccactcgcg  60

<210> SEQ ID NO 230
<211> LENGTH: 60
<212> TYPE: DNA
<213> ORGANISM: Artificial
<220> FEATURE:
<223> OTHER INFORMATION: Cloning oligoncleotide

<400> SEQUENCE: 230
gaccgcgagt gggttgcaca aggcccttaa ttttccaata acctagtata gggagctccg  60

<210> SEQ ID NO 231
<211> LENGTH: 4
<212> TYPE: PRT
<213> ORGANISM: Artificial
<220> FEATURE:
<223> OTHER INFORMATION: RCR motif sequence

<400> SEQUENCE: 231

Phe Leu Thr Tyr
1

<210> SEQ ID NO 232
<211> LENGTH: 5
<212> TYPE: PRT
<213> ORGANISM: Artificial
<220> FEATURE:
<223> OTHER INFORMATION: RCR motif sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be Asp or Glu

<400> SEQUENCE: 232

Tyr Xaa Xaa Lys Xaa
1               5